(12) United States Patent
Ohlmeyer

(10) Patent No.: US 12,398,103 B2
(45) Date of Patent: Aug. 26, 2025

(54) 3-DIARYLMETHYLENES AND USES THEREOF

(71) Applicant: Atux Iskay LLC, Plainsboro, NJ (US)

(72) Inventor: Michael Ohlmeyer, Plainsboro, NJ (US)

(73) Assignee: Atux Iskay LLC, Plainsboro, NJ (US)

( * ) Notice: Subject to any disclaimer, the term of this patent is extended or adjusted under 35 U.S.C. 154(b) by 383 days.

(21) Appl. No.: 17/912,404

(22) PCT Filed: Mar. 19, 2021

(86) PCT No.: PCT/US2021/023234
§ 371 (c)(1),
(2) Date: Sep. 16, 2022

(87) PCT Pub. No.: WO2021/188949
PCT Pub. Date: Sep. 23, 2021

(65) Prior Publication Data
US 2023/0146127 A1    May 11, 2023

Related U.S. Application Data

(60) Provisional application No. 62/992,569, filed on Mar. 20, 2020.

(51) Int. Cl.
| | | |
|---|---|---|
| *C07D 211/96* | (2006.01) |
| *C07D 207/08* | (2006.01) |
| *C07D 207/48* | (2006.01) |
| *C07D 211/18* | (2006.01) |
| *C07D 223/04* | (2006.01) |
| *C07D 241/04* | (2006.01) |
| *C07D 265/30* | (2006.01) |
| *C07D 279/12* | (2006.01) |
| *C07D 417/04* | (2006.01) |

(52) U.S. Cl.
CPC .......... *C07D 211/96* (2013.01); *C07D 207/08* (2013.01); *C07D 207/48* (2013.01); *C07D 211/18* (2013.01); *C07D 223/04* (2013.01); *C07D 241/04* (2013.01); *C07D 265/30* (2013.01); *C07D 279/12* (2013.01); *C07D 417/04* (2013.01)

(58) Field of Classification Search
CPC .................................................... C07D 211/96
See application file for complete search history.

(56) References Cited

U.S. PATENT DOCUMENTS 9,540,358 B2 *   1/2017   Ohlmeyer ................ A61P 1/04

\* cited by examiner

*Primary Examiner* — Golam M Shameem
(74) *Attorney, Agent, or Firm* — K&L Gates LLP; Brian J. Novak; Benjamin D. Heuberger

(57) ABSTRACT

3-Diarylmethylenes are disclosed. The compounds activate PP2A, suppress oncogenic kinase signaling, and negatively regulate MYC and MYCN in cancer. The compounds also induce FOXO transcription factor translocation to the nucleus by modulating PP2A and, as a consequence, exhibit anti-proliferative effects. They are useful in the treatment of a variety of disorders, including as a monotherapy in cancer treatment, or used in combination with other drugs to restore sensitivity to chemotherapy where resistance has developed.

9 Claims, No Drawings

3-DIARYLMETHYLENES AND USES THEREOF

RELATED APPLICATIONS

This application is a national stage entry under 35 USC 371 of international patent application no. PCT/US2021/023234, filed Mar. 19, 2021, which claims priority of U.S. provisional patent application No. 62/992,569, filed Mar. 20, 2020, the entire content of each of which is incorporated herein by reference.

STATEMENT OF GOVERNMENT SUPPORT

This invention was made with government support under W81XWH-20-1-0494 awarded by the Defense Health Agency, Medical Research and Development Branch, and under R44 AG071040 and R44 CA268329 awarded by the National Institutes of Health. The government has certain rights in the invention.

FIELD OF THE INVENTION

The invention relates to the use of small molecule modulators of PP2A, comprising 3-diarylmethyl cycloamine urea analogs to treat diseases such as cancer, inflammatory and autoimmune conditions, and neurodegenerative diseases.

BACKGROUND

The FOXO (Forkhead transcription factors, Class O) proteins are a group of transcription factors involved in control of a variety of physiological, metabolic and developmental pathways. They are downstream effectors in a number of signaling pathways including insulin and growth factor signaling; they are also regulated by oxidative stress and nutrient deprivation. Cellular processes affected by FOXO activity include cell cycle control, differentiation, proliferation and apoptosis. Disregulation of FOXO mediated processes has been implicated in a number of pathologies including tumorigenesis, inflammation, diabetes and neurodegenerative conditions amongst others. Activity of FOXO transcription factors are controlled in part by their sub-cellular localization, in particular their localization to the nucleus from the cytosol, and their subsequent transcriptional activation.

Four FOXO proteins designated FOXO1, FOXO3a, FOXO4 and FOXO6 are present in human cells and their activity is controlled by a variety of mechanisms including stability (proteolytic cleavage), sub-cellular localization and transcriptional activation. Activity of the first three members of the family is controlled by cytosolic-nuclear translocation.

FOXO1 regulates expression of a number of genes that play critical roles in cell cycle and apoptosis. A pivotal regulatory mechanism of FOXO is reversible phosphorylation, catalyzed by kinases and phosphatases. Phosphorylation of FOXO1 is associated with 14-3-3 binding and cytosolic localization, whereas dephosphorylated FOXO1 translocates to the nucleus and is transcriptionally active. FOXO3 is regulated in an analogous manner.

Protein phosphatase 2A is one of the four major serine threonine phosphatases and is implicated in the negative control of cell growth and division. Protein phosphatase 2A holoenzymes are heterotrimeric proteins composed of a structural subunit A, a catalytic subunit C, and a regulatory subunit B. The PP2A heterotrimeric protein phosphatase is a ubiquitous and conserved phosphatase with broad substrate specificity and diverse cellular functions. Among the targets of PP2A are proteins of oncogenic signaling cascades, such as Raf, MEK, and AKT.

PP2A interacts directly with FOXO1 and dephosphorylates FOXO1. Inhibition of PP2A phosphatases rescues FOXO1-mediated cell death by regulating the level of the pro-apoptotic protein BIM. In addition, PP2A directly regulates FOXO3a subcellular localization and transcriptional activation. Without wishing to be held to any particular theory, it may be that the compounds described herein promote apoptosis by acting on FOXO transcription factors via activation of PP2A.

Myc proteins (c-myc, Mycn and Mycl) target proliferative and apoptotic pathways vital for progression in cancer and it is overexpressed and deregulated in many human cancers. The control of Myc abundance through protein degradation has attracted considerable interest and Ser-62 phosphorylation by a number of kinases has been shown to stabilize the protein. PP2A is responsible for Ser-62 dephosphorylation which primes the protein for ubiquitylation and degradation, thus PP2A functions as a negative regulator of Myc.

Prostate cancer is the second leading cause of cancer death in men in America, behind lung cancer. According to the American Cancer Society, approximately 1 man in 36 will die of prostate cancer. Male hormones, specifically testosterone, fuel the growth of prostate cancer. By reducing the amount and activity of testosterone, the growth of advanced prostate cancer is slowed. Endocrine therapy, known as androgen ablation, is the first line of treatment for metastatic prostate cancer. Androgen deprivation therapy for metastatic prostate cancer results in tumor regression and symptomatic improvement in the majority of patients. However, metastatic prostate cancer inevitably progresses despite castrate levels of serum testosterone. Several new therapies have been approved for patients with castration-resistant prostate cancer (CRPC); however, none are curative and tumors ultimately develop resistance. To combat CRPC new approaches and novel therapies are required.

Breast cancer can affect both men and women. Breast cancer is the most prevalent cancer in women, after skin cancers, with about 1 in every 8 women expected to develop invasive breast cancer at some point. One subset of breast cancer expresses the androgen receptor (AR), which has been implicated as a therapeutic target in that subset. About 10-20% of breast cancers—more than one out of every 10—are found to be triple-negative. "Triple negative breast cancer" refers to a breast cancer that does not contain estrogen receptors, progesterone receptors, or human epidermal growth factor receptor 2 (HER2). This means that the growth of the cancer is not supported by the hormones estrogen and progesterone, nor by the presence of too many HER2 receptors. Therefore, triple-negative breast cancer does not respond to hormonal therapy (such as tamoxifen or aromatase inhibitors) or therapies that target HER2 receptors, such as Herceptin (chemical name: trastuzumab). While these tumors are often treatable, the chemotherapy is not targeted, and response durations are short. For doctors and researchers, there is intense interest in finding new medications that can treat breast cancer.

The compounds described herein, which are based on 3-diarylmethyl piperidine scaffold, exhibit anti-proliferative effects and are useful as monotherapy in cancer treatment. Additionally, they can be used in combination with other drugs to restore sensitivity to chemotherapy where resistance has developed.

SUMMARY OF THE INVENTION

A genus of 3-diarylmethyl cycloamine derivatives and related compounds has now been found that induce FOXO1 and FOXO3 transcription factor translocation to the nucleus by modulating PP2A activity. The compounds also deactivate pro-growth and pro-survival kinases such as phospo-ERK and phospho-AKT by promoting their deposphorylation by PP2A. The compounds described herein exhibit anti-proliferative effects, and are useful in the treatment of a variety of disorders, including as a monotherapy in cancer treatment, or used in combination with other drugs to restore sensitivity to chemotherapy where resistance has developed.

In a first aspect the invention relates to compounds of formula (I):

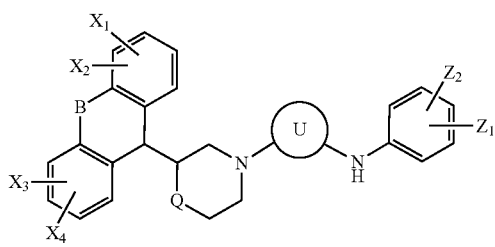

or a pharmaceutically acceptable salt thereof.

In a second aspect, the invention relates to pharmaceutical compositions comprising the compounds described herein.

In a third aspect, the invention relates to methods and uses of the above-described compounds in medicine, particularly for the treatment of a disease chosen from (a) cancer; (b) diabetes; (c) autoimmune disease; (d) age onset proteotoxic disease (particularly neurodegenerative disease); (e) mood disorder; (f) acne vulgaris; (g) solid organ transplant rejection (graft vs. host disease); (h) pulmonary disease (such as COPD or IPF); (i) cardiac hypertrophy and heart failure; j) viral or parasitic infection; and (k) inflammatory conditions (such as asthma). These methods include administering to a patient a therapeutically effective amount of a compound described herein.

In a fourth aspect, the invention relates to a method for restoring sensitivity to one or more chemotherapeutic agents in the treatment of cancer. The method includes administering an effective amount of a compound described herein.

In a fifth aspect, the invention relates to a method for treating a disease or disorder in a patient where the disease or disorder involves the dysregulation of PP2A influenced signaling cascades such as the PI3K-AKT, MAP kinase and mTOR pathways. These methods include administering to a patient a therapeutically effective amount of a compound described herein.

In a sixth aspect, the invention relates to a method for treating a disease or disorder in a patient where the disease or disorder involves the dysregulation of a Myc dependent signaling pathway. These methods include administering to a patient a therapeutically effective amount of a compound described herein.

In a seventh aspect, the invention relates to a method for treating a metabolic disease or disorder in a patient where the disease or disorder involves the dysregulation of the mTOR-PP2A signaling axis. The method includes administering a therapeutically effective amount of a compound described herein.

In another aspect, provided herein are compounds of the following formula:

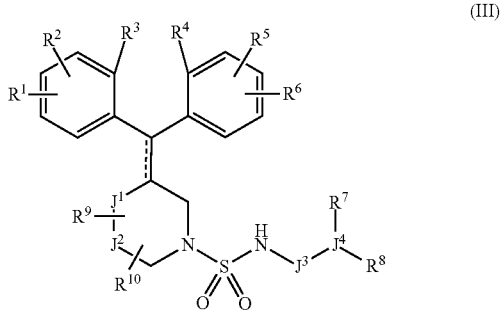

or a pharmaceutically acceptable salt thereof.

In another aspect, provided herein are compounds of the following formula:

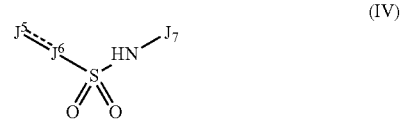

or a pharmaceutically acceptable salt thereof.

DETAILED DESCRIPTION

In one aspect, provided herein are compounds of formula (I):

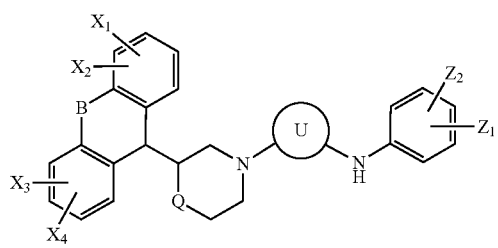

or a pharmaceutically acceptable salt thereof,
wherein:
B is absent or is selected from a direct bond, —$CH_2CH_2$—, —CH=CH—, O or S;
Q is selected from —$(CH_2)_n$— with n=0, 1 or 2, —O—, $NR^5$, —S— or —$SO_2$—;
U is a group selected from:

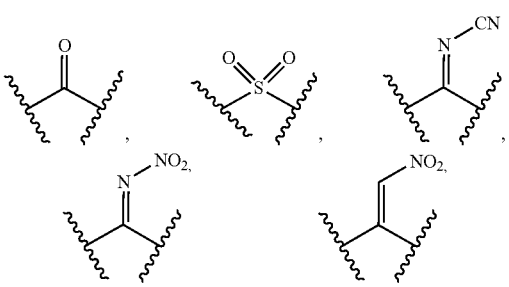

-continued

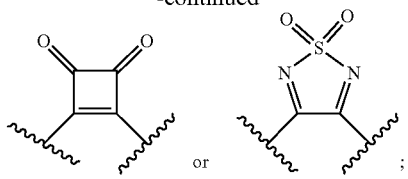
or

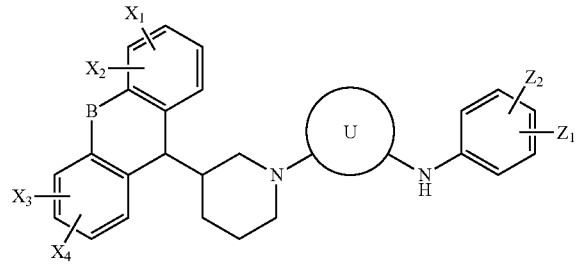
;

$X_1$, $X_2$, $X_3$ and $X_4$ are independently selected in each instance from hydrogen, halogen, nitro, cyano, $(C_1$-$C_6)$ alkyl optionally substituted with —OH, $(C_1$-$C_6)$haloalkyl, $(C_1$-$C_6)$haloalkoxy, $(C_1$-$C_6)$haloalkylthio, —$NR^1R^2$, —$OR^1$, —$C(O)R^1$, —$OC(O)R^1$, —$C(O)NR^1R^2$, —$C(O)OR^1$, —$SR^1$, —$SO_2R^1$, or —$SO_2NR^1R^2$;

$Z_1$ and $Z_2$ are independently selected in each instance from hydrogen, halogen, nitro, cyano, azido, $(C_1$-$C_6)$ alkyl, $(C_1$-$C_6)$haloalkyl, $(C_1$-$C_6)$haloalkoxy, $(C_1$-$C_6)$haloalkylthio, —$NR^1R^2$, —$NR^1C(O)R^2$, —$NR^1C(O)OR^3$, —$OR^1$, —$C(O)R^1$, —$OC(O)R^1$, —$C(O)NR^1R^2$, —$C(O)OR^1$, —$SR^1$, —$SO_2R^1$, or —$SO_2NR^1R^2$;

$R^1$, $R^2$ and $R^3$ are independently selected from lower alkyl groups and $R^1$ and $R^2$ may be joined to form a ring; and $R^5$ is selected from optionally substituted lower alkyl, lower cycloalkyl, or acyl.

In some embodiments, provided herein are compounds of formula IIa:

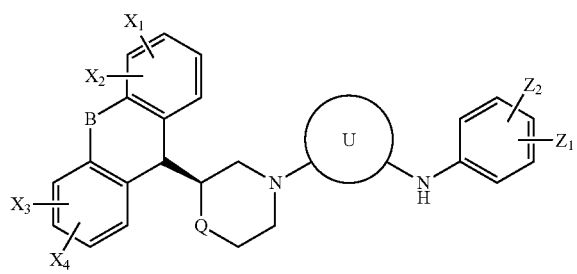

(IIa)

or a pharmaceutically acceptable salt thereof.

In some embodiments, provided herein are compounds of formula IIb:

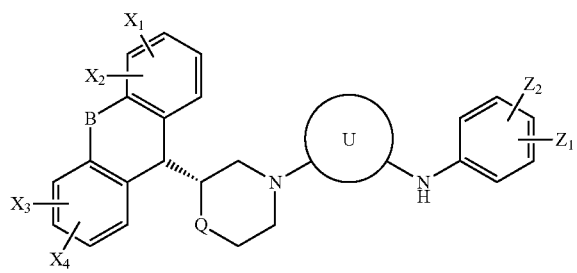

(IIb)

or a pharmaceutically acceptable salt thereof.

In some embodiments described herein, the compound may be of formula I, IIa, IIb, IIc, IId, IIe, or IIf.

In some embodiments Q is —$(CH_2)_n$— with n=0.
In some embodiments Q is —$(CH_2)_n$— with n=2.

In some embodiments Q is S or $SO_2$.
In some embodiments Q is —$(CH_2)_n$— with n=1.

In some embodiments, provided herein are compounds of formula IIc:

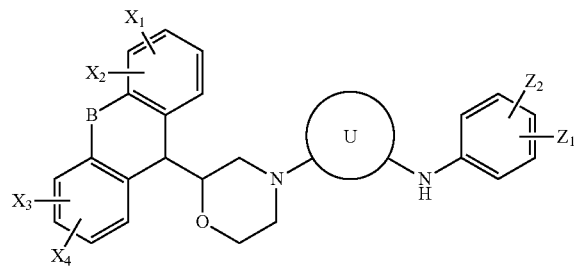

(IIc)

or a pharmaceutically acceptable salt thereof.

In some embodiments Q is —O—.

In some embodiments, provided herein are compounds of formula IId.

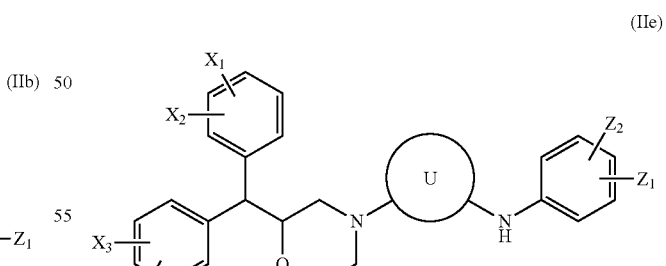

(IId)

or a pharmaceutically acceptable salt thereof.

In some embodiments, B is absent.

In some embodiments, provided herein are compounds of formula IIe:

(IIe)

or a pharmaceutically acceptable salt thereof.

In other embodiments, B is a direct bond to give a fluorenyl compound.

In still other embodiments, B is —$CH_2CH_2$—.

In some embodiments, provided herein are compounds of formula IIf:

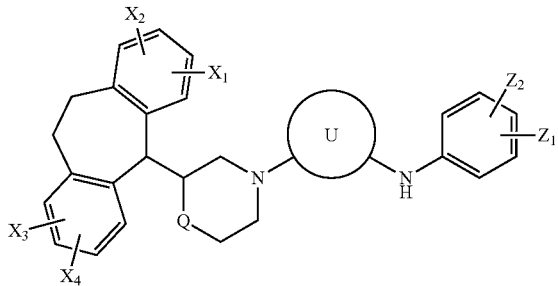

(IIf)

or a pharmaceutically acceptable salt thereof.

In some embodiments, $X^1$, $X^2$, $X^3$, and $X^4$ are independently selected in each instance from hydrogen, halogen, nitro, cyano, ($C_1$-$C_6$)alkyl optionally substituted with —OH, ($C_1$-$C_6$)haloalkyl, ($C_1$-$C_6$)haloalkoxy, ($C_1$-$C_6$)haloalkylthio, —$NR^1R^2$, —$OR^1$, —$C(O)R^1$, —$OC(O)R^1$, —$C(O)NR^1R^2$, —$C(O)OR^1$, —$SR^1$, —$SO_2R^1$, and —$SO_2NR^1R^2$. In other embodiments, $X^2$ and $X^4$ are each hydrogen. In still other embodiments, $X^2$ and $X^4$ are each hydrogen, and $X^1$ and $X^3$ are each chosen independently from —H, —F, —Cl, —$CF_3$, —$C(CH_3)_2OH$, or —$C(O)NMe_2$. In further embodiments, all of $X^1$, $X^2$, $X^3$ and $X^4$ are each hydrogen. In yet other embodiments, at least one of $X^1$, $X^2$, $X^3$ and $X^4$ is located at a carbon two positions away from a bridgehead carbon.

In some embodiments, $Z^1$ and $Z^2$ are independently selected in each instance from hydrogen, halogen, nitro, cyano, azido, ($C_1$-$C_6$)alkyl, ($C_1$-$C_6$)haloalkyl, ($C_1$-$C_6$)haloalkoxy, ($C_1$-$C_6$)haloalkylthio, —$NR^1R^2$, —$NR^1C(O)R^2$, —$NR^1C(O)OR^6$, —$OR^1$, —$C(O)R^1$, —$OC(O)R^1$, —$C(O)NR^1R^2$, —$C(O)OR^1$, —$SR^1$, —$SO_2R^1$, and —$SO_2NR^1R^2$. In other embodiments, $Z^1$ is H. In still other embodiments, $Z^2$ is chosen from hydrogen, halogen, and ($C_1$-$C_6$)haloalkoxy. In yet other embodiments, $Z^2$ is chosen from hydrogen, F, Cl, and $OCF_3$. In further embodiments, $Z^2$ is in the para position.

In some embodiments, Q is —S—.

In some embodiments, Q is —$SO_2$—.

In some embodiments, U is

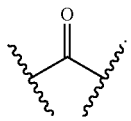

In some embodiments, U is

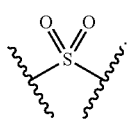

In some embodiments, U is

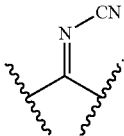

In some embodiments, U is

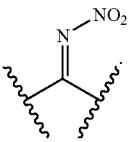

In some embodiments, U is

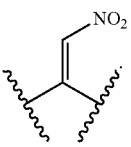

In some embodiments, U is

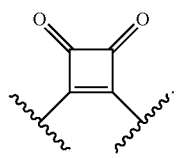

In some embodiments, U is

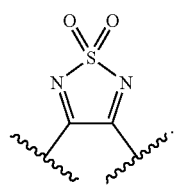

In some embodiments, $X^1$, $X^2$, $X^3$, and $X^4$ are independently selected in each instance from hydrogen, halogen, nitro, cyano, ($C_1$-$C_6$)alkyl optionally substituted with —OH, ($C_1$-$C_6$)haloalkyl, ($C_1$-$C_6$)haloalkoxy, ($C_1$-$C_6$)haloalkylthio, —$NR^1R^2$, —$OR^1$, —$C(O)R^1$, —$OC(O)R^1$, —$C(O)NR^1R^2$, —$C(O)OR^1$, —$SR^1$, —$SO_2R^1$, and —$SO_2NR^1R^2$.

In some embodiments, $X^2$ and $X^4$ are each hydrogen.

In some embodiments, $X^1$ and $X^3$ are each chosen independently from hydrogen, halogen, nitro, cyano, ($C_1$-$C_6$) alkyl optionally substituted with —OH, ($C_1$-$C_6$)haloalkyl, ($C_1$-$C_6$)haloalkoxy, ($C_1$-$C_6$)haloalkylthio, —$NR^1R^2$, —$OR^1$, —$C(O)R^1$, —$OC(O)R^1$, —$C(O)NR^1R^2$, —$C(O)OR^1$, —$SR^1$, —$SO_2R^1$, and —$SO_2NR^1R^2$.

In some embodiments, $X^1$ and $X^3$ are each chosen independently from —H, —F, —Cl, —$CF_3$, —OMe, or —$OCF_3$.

In some embodiments, $X^1$, $X^2$, $X^3$ and $X^4$ are each hydrogen.

In some embodiments, at least one of $X^1$, $X^2$, $X^3$ and $X^4$ is located at a carbon two positions away from a bridgehead carbon.

In some embodiments, $Z^1$ and $Z^2$ are independently selected in each instance from hydrogen, halogen, nitro, cyano, azido, $(C_1-C_6)$alkyl, $(C_1-C_6)$haloalkyl, $(C_1-C_6)$haloalkoxy, $(C_1-C_6)$haloalkylthio, —$NR^1R^2$, —$NR^1C(O)R^2$, —$NR^1C(O)OR^6$, —$OR^1$, —$C(O)R^1$, —$OC(O)R^1$, —$C(O)NR^1R^2$, —$C(O)OR^1$, —$SR^1$, —$SO_2R^1$, and —$SO_2NR^1R^2$.

In some embodiments, $Z^1$ and $Z^2$ are independently selected in each instance from hydrogen, halogen, halo($C_1$-$C_6$)alkyl, $(C_1-C_6)$alkoxy, and halo($C_1$-$C_6$)alkoxy.

In some embodiments, $Z^1$ is hydrogen.

In some embodiments, $Z^2$ is chosen from hydrogen, halogen, and $(C_1-C_6)$haloalkoxy.

In some embodiments, $Z^2$ is chosen from hydrogen, F, Cl, $CF_3$, and trifluoromethoxy.

In some embodiments, $Z^2$ is trifluoromethoxy.

In some embodiments, one of $Z^1$ and $Z^2$ is para to the aniline NH.

In some embodiments, $Z^1$ is hydrogen $Z^2$ is para to the aniline NH.

In some embodiments:
B is absent or —$CH_2CH_2$—;
U is selected from or

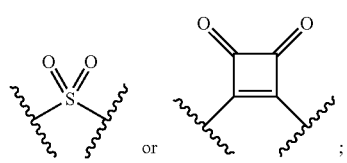 [SMILES: *S(*)(=O)=O ; *c1c(*)c(=O)c1=O]

Q is selected from —$(CH_2)_n$—, with n=1 or O;
$X^2$ and $X^4$ are each hydrogen, and $X^1$ and $X^3$ are each chosen independently from —H, —F, —Cl, —$CF_3$, —$C(CH_3)_2OH$, —$C(O)NMe_2$;
$R^1$ and $R^2$ are independently selected in each instance from the group consisting of hydrogen and $(C_1-C_6)$ alkyl;
$Z^1$ is hydrogen; and
$Z^2$ is selected in each instance from hydrogen, halogen, and $(C_1-C_6)$haloalkoxy.

In some embodiments, provided herein are compounds of formula (I):

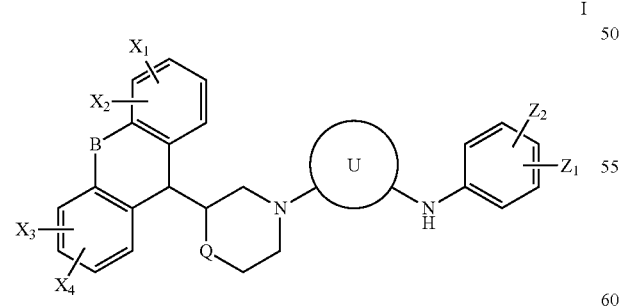

or a pharmaceutically acceptable salt thereof,
wherein:
B is absent or is selected from a direct bond, O, S, —$CH_2CH_2$—, or —CH=CH—;
Q is selected from —$(CH_2)_n$— with n=0, 1 or 2, —O—, —S—, —$SO_2$—, or $NR^5$;

U is a group selected from:

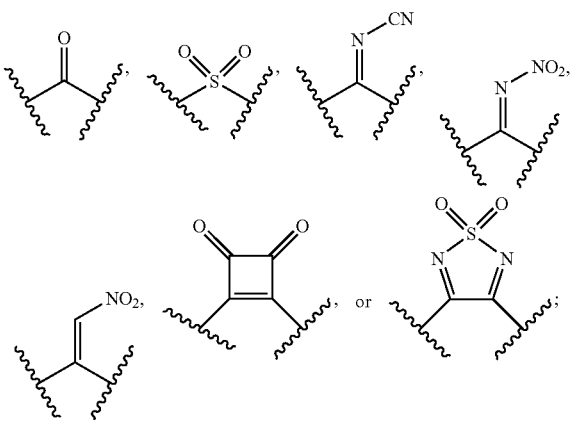

$X^1$, $X^2$, $X^3$, and $X^4$ are independently selected in each instance from hydrogen, halogen, nitro, cyano, $(C_1-C_6)$ alkyl optionally substituted with —OH, $(C_1-C_6)$haloalkyl, $(C_1-C_6)$haloalkoxy, $(C_1-C_6)$haloalkylthio, —$NR^1R^2$, —$OR^1$, —$C(O)R^1$, —$OC(O)R^1$, —$C(O)NR^1R^2$, —$C(O)OR^1$, —$SR^1$, —$SO_2R^1$, or —$SO_2NR^1R^2$;
$R^1$ and $R^2$ are independently selected in each instance from hydrogen or $(C_1-C_6)$alkyl;
$Z^1$ and $Z^2$ are independently selected in each instance from hydrogen, halogen, nitro, cyano, azido, $(C_1-C_6)$ alkyl, $(C_1-C_6)$haloalkyl, $(C_1-C_6)$haloalkoxy, $(C_1-C_6)$ haloalkylthio, —$NR^3R^4$, —$NR^3C(O)R^4$, —$NR^3C(O)OR^5$, —$OR^3$, —$C(O)R^3$, —$OC(O)R^3$, —$C(O)NR^3R^4$, —$C(O)OR^3$, —$SR^3$, —$SO_2R^3$, or —$SO_2NR^3R^4$;
$R^3$ and $R^4$ are independently selected from lower alkyl groups or $R^3$ and $R^4$ may be joined to form a ring; and
$R^5$ is selected from optionally substituted lower alkyl, lower cycloalkyl, or acyl.

In some embodiments, provided herein are compounds of the following formula:

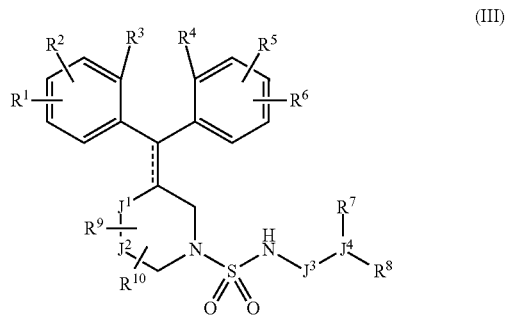

or a pharmaceutically acceptable salt thereof,
wherein
==== is a single or a double bond;
$R^1$, $R^2$, $R^5$, and $R^6$ are each, independently, H, halogen, $NO_2$, $C_{1-3}$ alkyl, $C_{1-3}$ haloalkyl, O—($C_{1-3}$ alkyl), or O—($C_{1-3}$ haloalkyl);
$R^3$ and $R^4$ are each, independently, H, halogen, $NO_2$, $C_{1-3}$ alkyl, $C_{1-3}$ haloalkyl, O—($C_{1-3}$ alkyl), or O—($C_{1-3}$ haloalkyl), or $R^3$ and $R^4$ are covalently linked together to form $C_{1-3}$ alkylene;

R[7] and R[8], are each, independently, H, halogen, NO$_2$, C$_{1-3}$ alkyl, C$_{1-3}$ haloalkyl, O—(C$_{1-3}$ alkyl), O—(C$_{1-3}$ haloalkyl), or N(H)C(O)O(C$_{1-6}$ alkyl), or R[7] and R[8] are covalently linked together to form O(C$_1$-3 alkylene)O or O(C$_1$-3 haloalkylene)O;

R[9] and R[10], are each, independently, H, OH, halogen, C$_{1-3}$ alkyl, C$_{1-3}$ haloalkyl, O—(C$_{1-3}$ alkyl), O—(C$_{1-3}$ haloalkyl), C$_{1-3}$ alkylene-OH, or C$_{1-3}$ alkylene-O—C$_{1-3}$ alkyl;

J[1] is CH$_2$, NH, S, or O;

J[2] is a bond or C$_{1-3}$ alkylene;

J[3] is a bond or C$_{1-3}$ alkylene; and

J[4] is C$_{6-12}$ aryl or C$_{2-9}$ heteroaryl, each heteroatom independently selected from N, O, or S.

In some embodiments, the compounds provided herein have the following formula:

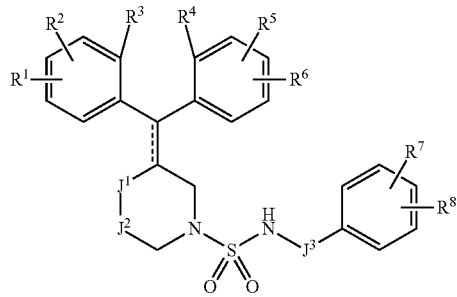

(IIIa)

or a pharmaceutically acceptable salt thereof.

In some embodiments, the compounds provided herein have the following formula:

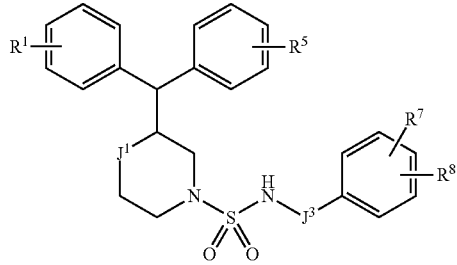

(IIIb)

or a pharmaceutically acceptable salt thereof
wherein
R[1] and R[5] are, independently, H or F.

In some embodiments, the compounds provided herein have the following formula:

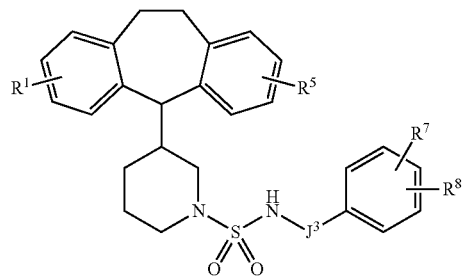

(IIIc)

or a pharmaceutically acceptable salt thereof
wherein
R[1] and R[5] are, independently, H or F.

In some embodiments, the compounds provided herein have the following formula:

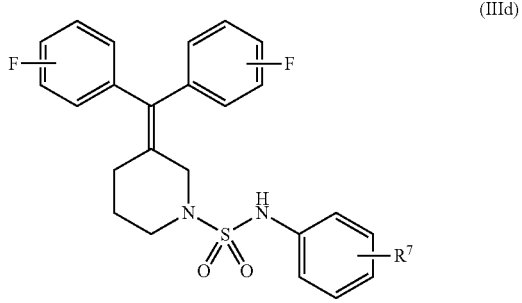

(IIId)

or a pharmaceutically acceptable salt thereof.

In some embodiments, the compounds provided herein have the following formula:

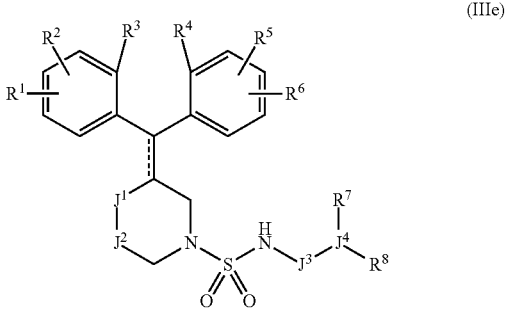

(IIIe)

or a pharmaceutically acceptable salt thereof.

In some embodiments, the compounds provided herein have the following formula:

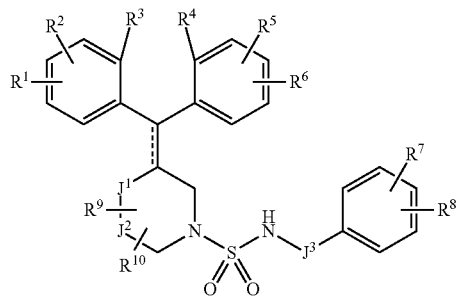

(IIIf)

or a pharmaceutically acceptable salt thereof.

In some embodiments, the compounds provided herein have the following formula:

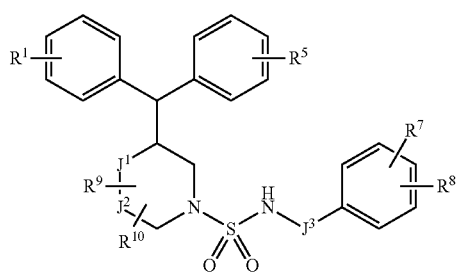

(IIIg)

or a pharmaceutically acceptable salt thereof
wherein
$R^1$ and $R^5$ are, independently, H or F.

In some embodiments, the compounds provided herein have the following formula:

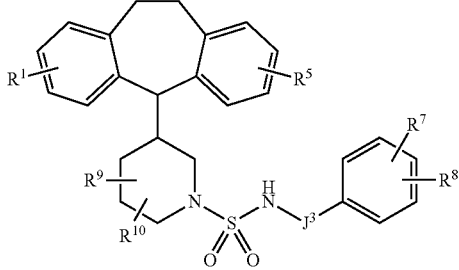

(IIIh)

or a pharmaceutically acceptable salt thereof
wherein
$R^1$ and $R^5$ are, independently, H or F.

In some embodiments, the compounds provided herein have the following formula:

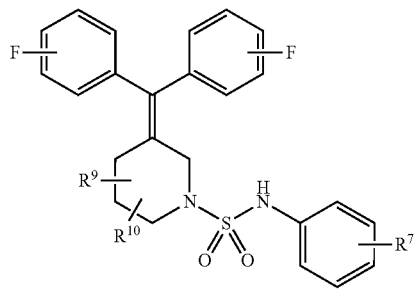

(IIIi)

or a pharmaceutically acceptable salt thereof.

In some embodiments, provided herein are compounds of the following formula:

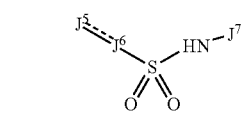

(IV)

or a pharmaceutically acceptable salt thereof,

==== is a single or a double bond;

$J^5$ is

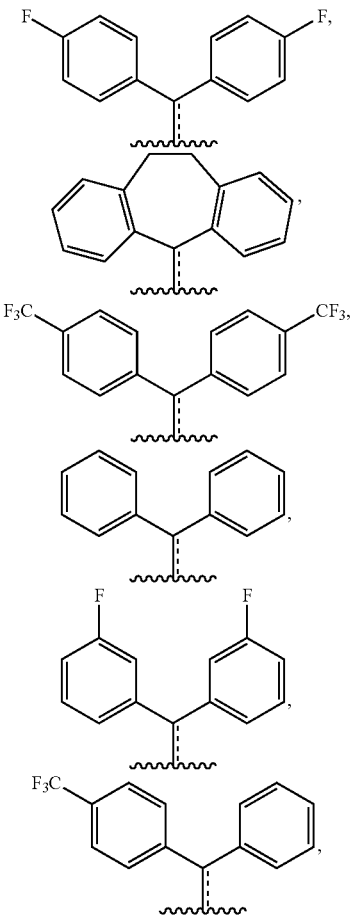

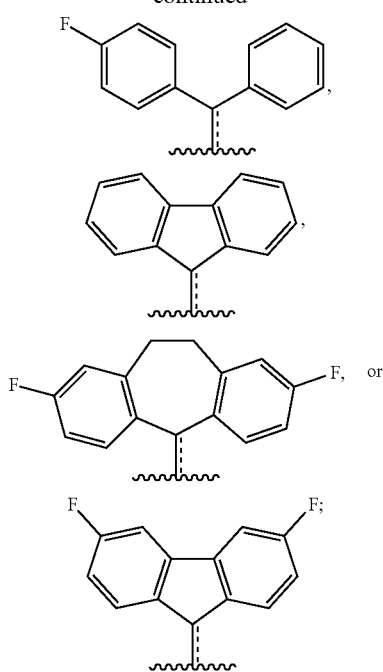
J⁶ is
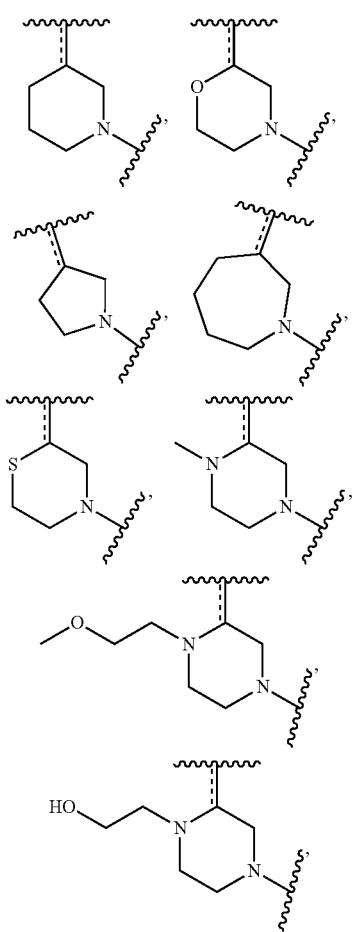
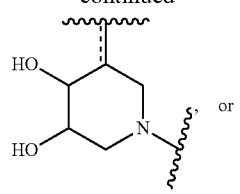
J⁷ is
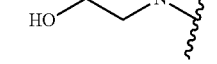
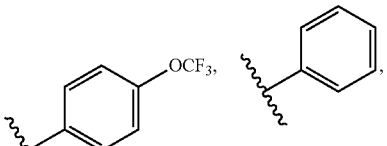
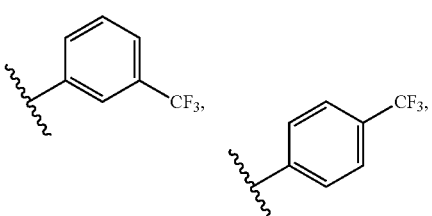
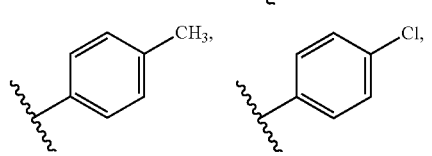
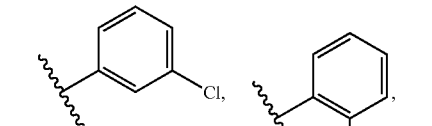
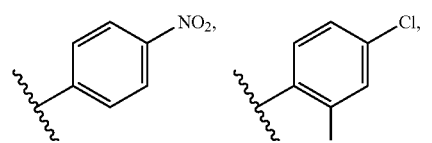
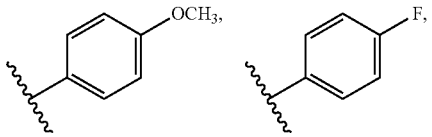

-continued

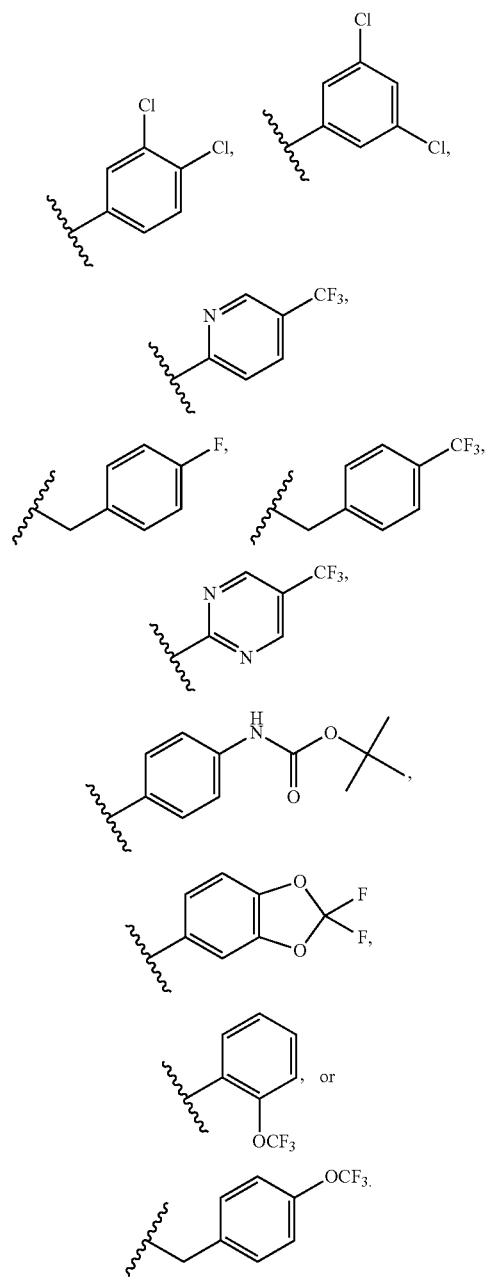

In some embodiments of the formulae provided herein, ==== is a single bond.

In some embodiments of the formulae provided herein, ==== is a single bond, and $J^6$ is

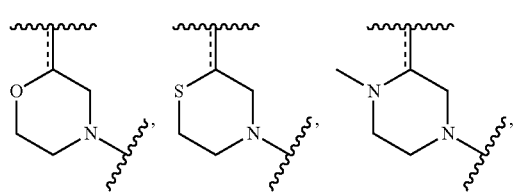

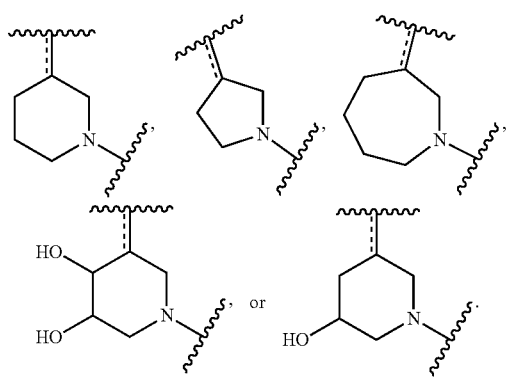

In some embodiments of the formulae provided herein, $J^6$ is

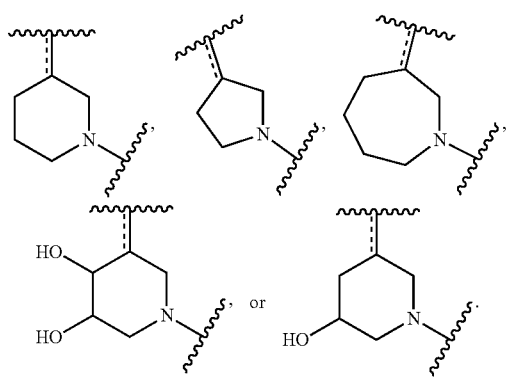

In some embodiments of the formulae provided herein, ==== is a double bond, and $J^1$ is $CH_2$.

In some embodiments of the formulae provided herein, ==== is a single bond, and $J^1$ is $CH_2$.

In some embodiments of the formulae provided herein, ==== is a single bond, and $J^1$ is NH, S, or O. In some embodiments, $J^1$ is NH or O.

In some embodiments of the formulae provided herein, $J^3$ is a bond or $CH_2$.

In some embodiments, $J^2$ is $CH_2$.

In some embodiments, $J^1$ is $CH_2$. In some embodiments, $J^1$ is NH. In some embodiments, $J^1$ is O.

In some embodiments, $R^1$ and $R^5$ are each, independently, H, halogen, $NO_2$, $C_{1-3}$ alkyl, $C_{1-3}$ haloalkyl, O—($C_{1-3}$ alkyl), or O—($C_{1-3}$ haloalkyl), and $R^2$ and $R^6$ are H.

In some embodiments, $R^1$ and $R^5$ are each, independently, H, halogen, $CF_3$, or $CH_3$, and $R^2$ and $R^6$ are H.

In some embodiments, $R^3$ and $R^4$ are H, or $R^3$ and $R^4$ are covalently linked together to form $C_{1-3}$ alkylene.

In some embodiments, $R^7$ is F, Cl, $CF_3$, $OCF_3$, or $NO_2$, and $R^8$ is H.

In some embodiments, $R^9$ and $R^{10}$, are each, independently, H, OH, $C_{1-3}$ alkyl, O—($C_{1-3}$ alkyl), $C_{1-3}$ alkylene-OH, or $C_{1-3}$ alkylene-O—$C_{1-3}$ alkyl.

In some embodiments, $R^9$ and $R^{10}$, are each, independently, H, OH, $CH_3$, $CH_2CH_2$—OH, or $CH_2CH_2$—O—$CH_3$. In some embodiments, $R^9$ and $R^{10}$, are each, independently, OH, $CH_3$, $CH_2CH_2$—OH, or $CH_2CH_2$—O—$CH_3$. In some embodiments, $R^9$ is H, OH, $CH_3$, $CH_2CH_2$—OH, or $CH_2CH_2$—O—$CH_3$, and $R^{10}$ is H. In some embodiments, $R^9$ and $R^{10}$, are each, independently, H or OH.

In some embodiments, $R^7$ and $R^8$, are each, independently, H, F, Cl, $CF_3$, $OCF_3$, or $NO_2$.

In some embodiments:

$R^1$, $R^2$, $R^5$, and $R^6$ are each, independently, H or F; and $R^3$ and $R^4$ are H, or $R^3$ and $R^4$ are covalently linked together to form $CH_2CH_2$.

In some embodiments:

$R^1$, $R^2$, $R^5$, and $R^6$ are each, independently, H or F;

$R^3$ and $R^4$ are H, or $R^3$ and $R^4$ are covalently linked together to form $CH_2CH_2$;

$R^7$ and $R^8$, are each, independently, H, F, Cl, $CF_3$, $OCF_3$, $NO_2$, $N(H)C(O)O(C_4$ alkyl), or $R^7$ and $R^8$ are covalently linked together to form $OC(F_2)O$;

$J^1$ is $CH_2$, or O;

$J^2$ is a bond or $CH_2$; and $J^3$ is a bond or $CH_2$.

In some embodiments of the formulae provided herein, halogen or halo is F or Cl.

In some embodiments, haloalkyl or haloalkylene is fluoroalkyl or fluoroalkylene, respectively, where more than one fluorine may be included. In some embodiments, one, two or three fluorines are included.

In some embodiments, $C_{1-3}$ alkyl is methyl or ethyl.

In some embodiments, $C_{1-3}$ alkylene is methylene or ethylene.

In some embodiments, $C_{6-12}$ aryl is phenyl or naphthyl. In some embodiments, aryl is biphenyl.

In some embodiments, $C_{2-9}$ heteroaryl is pyridyl or pyrimidinyl.

In some embodiments of the compounds provided herein, the compound is a compound of Table 1 or a pharmaceutically acceptable salt thereof. In some embodiments of the compounds provided herein, the compound is a compound of Table 2 or a pharmaceutically acceptable salt thereof.

Also provided herein are compositions comprising a compound provided herein.

Also provided herein are pharmaceutical compositions comprising a pharmaceutically acceptable carrier and a compound provided herein.

The compounds described herein contain asymmetric centers and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representations:

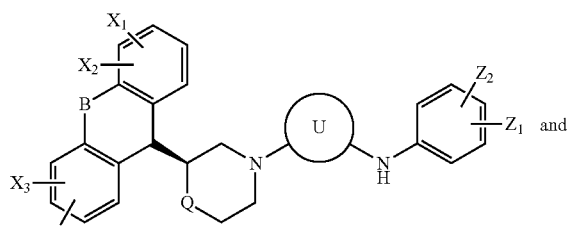

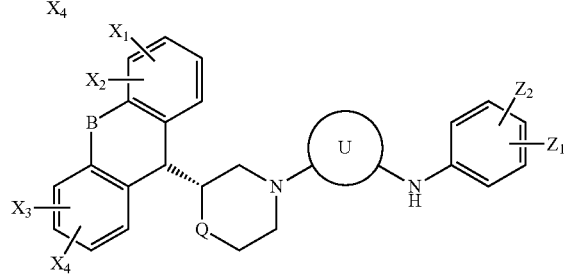

indicate each single enantiomer of known absolute stereochemistry, i.e., each of the two structures is a substantially pure single enantiomer. For the purpose of the present disclosure, a "pure" or "substantially pure" enantiomer is intended to mean that the enantiomer is at least 95% of the configuration shown and 5% or less of other enantiomers. The graphic representation:

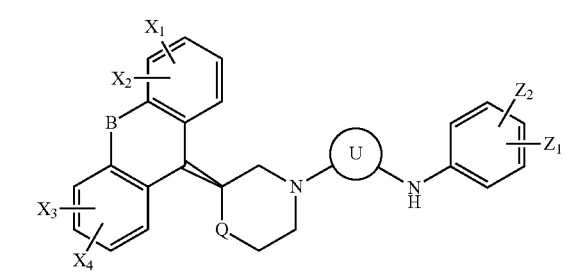

indicates a single enantiomer of unknown absolute stereochemistry, i.e., it could be either of the two structures shown above, as a substantially pure single enantiomer. And, finally, the structure:

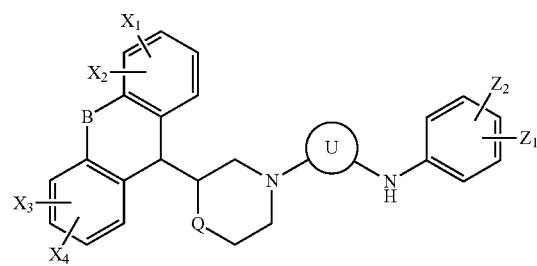

conveys no information regarding stereochemistry. This structure could be a single enantiomer or a mixture of enantiomers, including a racemic micture.

In any of these possibilities, compounds can be single enantiomers of formula IIa or formula IIb or a mixture of the two. If a mixture, the mixture will most commonly be racemic, but it need not be. Substantially pure single enantiomers of biologically active compounds such as those described herein often exhibit advantages over their racemic mixture.

All the members of the genus described above exhibit biological activity in screens that are predictive of utility. However, it may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genus I that are not in the public's possession.

Also provided herein is a pharmaceutical composition comprising a compound disclosed above, or a pharmaceutically acceptable salt form thereof, and a pharmaceutically acceptable carrier or diluent.

While it may be possible for the compounds of formula I to be administered as the raw chemical, it is preferable to present them as a pharmaceutical composition. According to a further aspect, the present invention provides a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

Formulations of the compounds and compositions described herein may be administered by a variety of methods: oral (including, but not limited to, capsules, cachets, tablets, powder, granules, solutions, suspensions, emulsions, tablets, or sublingual tablets), buccal, by inhalation (by using, for instance, an inhaler, a nebulizer, an aerosol, a gas, etc.), nasal, topical (including, but not limited to, lotions, creams, ointments, patches (i.e., transdermal), gels, liniments, pastes), ophthalmic, to the ear, rectal (for instance, by using a suppository or an enema), vaginal, or parenteral, depending on the severity and type of the disease being treated. In some embodiments, the compositions are administered orally or intravenously. The formulations include those suitable for oral, parenteral (including subcutaneous, intradermal, intramuscular, intracranial, intravenous and intraarticular), rectal, vaginal, nasal (inhalation), and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}H$, $^{3}H$, $^{13}C$, $^{4}C$ $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating cancer in a patient, the method comprising administering to the patient a therapeutically effective amount of a compound of formula I. In some embodiments, the cancer is characterized by dysregulation of the PI3K-AKT-FOXO signaling pathway. For example, the cancer can be selected from the group consisting of: ovarian, pancreatic, renal cell, breast, prostate, lung, hepatocellular carcinoma, glioma, leukemia, lymphoma, colorectal cancers, and sarcomas.

In some embodiments, the method further comprises administering one or more additional cancer chemotherapeutic agents. In some embodiments, the one or more additional cancer chemotherapeutic agents are EGFR inhibitors.

In some embodiments, the cancer is chemotherapy resistant cancer. In some embodiments, the method further comprises administering one or more cancer chemotherapeutic agents. In some embodiments, the one or more cancer chemotherapeutic agents are EGFR inhibitors.

In some embodiments, administration of a compound of formula I can restore sensitivity to one or more chemotherapeutic agents in a patient wherein the patient has developed a resistance to the one or more chemotherapeutic agents. More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

The compounds described herein can also be administered in combination with existing methods of treating cancers, for example by chemotherapy, irradiation, or surgery. Thus, there is further provided a method of treating cancer comprising administering an effective amount of a compound according to formula I to a patient, wherein a therapeutically effective amount of one or more additional cancer chemotherapeutic agents are administered to the patient.

Also provided herein is a method for treating diabetes in a patient, the method comprising administering to the patient a therapeutically effective amount of a compound of formula I.

Further provided herein is a method for treating an autoimmune disease in a patient, the method comprising administering to the patient a therapeutically effective amount of a compound of formula I. The autoimmune disease can be, for example, inflammatory bowel disease (IBD). Immune responses are constantly and tightly regulated and one important cellular component in maintaining self tolerance (i.e., prevention of autoimmunity) and tolerance of benign commensal gut flora are regulatory T cells (Treg). Treg can be subdivided into multiple phenotypes, but the most common are CD4+CD25+ T cells that express the transcription factor Foxp3. Foxp3 is a direct transcriptional target of FOXO proteins, particularly FOXO1 and FOXO3. Thus activation of FOXO proteins in naïve T-cells promotes and directs differentiation to maintain a population of Treg cells.

Acute immune mediated rejection and chronic immune mediated rejection are key obstacles to successful solid organ transplantation. It is believed that these forms of rejection can be prevented/overcome by amplifying Treg number and or function. Similarly, a common and morbid complication of allogeneic hematopoietic cell transplants (Allo-HCT) used to treat various malignant and non-malignant conditions, is graft versus host disease, in which the transplanted immune cells from the donor damage multiple organs in the recipient (most notably skin, gut, and liver). Increasing experimental and clinical data indicate that Tregs can be harnessed to prevent and or treat this disease process.

Thus compounds of the present invention are useful in treatment of autoimmune and related diseases, by activating FOXO proteins and inducing T cell differentiation to Tregs. Compounds may be administered therapeutically to subjects directly, or alternatively, T cells may be collected from a subject and differentiated ex vivo to Tregs as described by Taylor et al. [*Blood* 99, 3493-3499 (2002)].

Aspects of the invention include methods for treatment of autoimmune disease characterized by deficiency in Treg function comprising administering a therapeutically useful amount of compound of formula I. The method can also include extraction of naïve T-cells from a patient, differentiation of T-cells to Tregs ex vivo by treatment with a compound of formula I, optionally supplemented with an HDACi, followed by administration of Tregs to patient with optional separation of compound of formula I from Tregs prior to their administration. As stated above, autoimmune diseases that can be so treated include IBD, solid organ transplant rejection, and GvHD in allo-HCT.

In some embodiments, the compounds can be administered to a patient to treat an autoimmune disorder, for example, Addison's disease, Amyotrophic Lateral Sclerosis, celiac disease, Crohn's disease, diabetes, eosinophilic fasciitis, Guillain-Barre syndrome (GBS), Graves' disease, Lupus erythematosus, Miller-Fisher syndrome, psoriasis, rheumatoid arthritis, ulcerative colitis, and vasculitis. In some embodiments, the compound provided herein can be used for treating a disease or disorder in a patient wherein the disease or disorder involves excessive or unregulated cellular proliferation, the method comprising administering to the patient a therapeutically effective amount of a compound of formula I. Also provided herein is a method for treating a disease or disorder in a patient where the disease or disorder involves the dysregulation of the PI3K-AKT-FOXO signaling pathway, the method comprising administering to the patient a therapeutically effective amount of a compound of formula I.

Further provided herein is a method for treating a disease in a patient wherein the disease is characterized by proteotoxicity, including age onset proteotoxicity leading to neurodegeneration, the method comprising administering to the patient a therapeutically effective amount of a compound of formula I. Hyperphosphorylated Tau has been implicated as the pathogenic protein in several neurodegenerative diseases and furthermore PP2A has been shown to be an important phosphatase in reversing aberrant phosphorylation of Tau; see for example Ludovic Martin et al., Tau protein phosphatases in Alzheimer's disease: The leading role of PP2A in Ageing Research Reviews 12 (2013) 39-49; Miguel Medina and Jesus Avila, Further understanding of tau phosphorylation: implications for therapy in Expert Rev. Neurotherapy, 15(1), 115-112 (2015) and Michael Voronkov et al., Phosphoprotein phosphatase 2A: a novel druggable target for Alzheimer's disease in Future Med Chem. 2011 May, 3(7) 821-833. Hyperphosphorylated alpha-Synuclein is a second exemplar of a toxic protein, and again PP2A has been shown to reverse its aberrantly phosphorylated state; see for example Kang-Woo Lee et al., Enhanced Phosphatase Activity Attenuates alpha-Synucleinopathy in a Mouse Model in Neurobiology of Disease, May 11, 2011, 31(19) 6963-6971. In some embodiments, the disease is selected from the group consisting of. Alzheimer's disease, Parkinson's disease, Huntington's disease, amyotrophic lateral sclerosis, frontotemporal dementia, progressive supranuclear palsy, corticobasal degeneration and Pick's disease.

A second feature of Alzheimer's disease is deposition of amyloid plaques and phosphorylation of Amyloid Precursor Protein (APP) at threonine-668 in the cytoplasmic domain of APP is involved in it's processing to generate toxic amyloid-beta (see T. Zhang et al, Int. J. Mol. Sci. 2020, 21, 209). Activation of PP2A by treatment with compounds of the present invention decreases threonine-668 phosphorylation and suppresses pathological amyloidogenesis contributing to the development of Alzheimer's disease.

The compounds provided herein may further be used in a method for treating a mood disorder in a patient by administering to the patient a therapeutically effective amount of a compound of formula I. In some embodiments, the mood disorder is stress-induced depression.

Also provided herein is a method for treating acne vulgaris in a patient by administering to the patient a therapeutically effective amount of a compound of formula I.

Further provided herein is a method for treating pulmonary disease such as COPD. Protein phosphatase 2A (PP2A) is a primary serine-threonine phosphatase that modulates inflammatory responses in asthma and COPD. PP2A has shown to be dysregulated in mouse models of COPD, and inhibiting PP2A activity exacerbated inflammatory responses in the lung. Conversely, increasing PP2A activity via PP2A protein transfection down regulated cytokine expression and prevented the induction of proteases following cigarette smoke extract (CSE) treatment. Thus, increasing PP2A activity by treatment with compounds of the present invention may ameliorate or reverse the pathology underlying lung diseases such as COPD.

Idiopathic Pulmonary Fibrosis is a fatal lung disease in which there is progressive and irreversible scaring of the lung associated with changes to alveolar epithelial cells and aberrant fibroblast proliferation and activation. The underlying causative agent in IPF is usually unknown (hence idiopathic) and the prognosis after diagnosis is dismal with a median survival time of three years. IPF is characterized by a continuous expansion of the fibroblast population and excessive deposition of collagen in the alveolar wall leading to scarred, non-functional airspaces progressive hypoxia and death by asphyxiation. In normal lung tissue fibroblasts interact with the extracellular matix(ECM) and signaling via integrins activates PP2A and this suppresses fibroblast growth and proliferation. In IPF fibroblasts this signaling is defective and PP2A activation is muted; in these aberrant cells, uncontrolled fibroblast proliferation and collagen secretion occurs. Diminished PP2A signaling in PP2A fibroblasts has several consequences: 1. Excessive phosphorylation of the transcription factor FOXO3a, which leads to exit of phospho-FOXO3a from the nucleus to the cytoplasm where it is sequestered by 14-3-3 proteins. PP2A is known to be the phosphatase responsible for dephosphorylating cytoplasmic FOXO3a and promoting it's nuclear translocation. Activated, phospho-Akt is a major kinase responsible for phosphorylation of FOXO3a and PP2A is the phosphatase responsible for dephosphorylating and deactivating Akt. Thus PP2A activation promotes FOXO3a activity in two ways, by suppressing the activity of a major kinase, Akt, that inactivates it, and second by dephosphorylating cytoplasmic phospho-FOXO3a directly to cause nuclear translocation. Deficient nuclear FOXO3 protects IPF fibroblasts from polymerized collagen matrix induced apoptosis, therefore PP2A activation will suppress growth of, and will induce apoptosis of IPF fibroblasts. 2. Low PP2A activity in IPF fibroblasts results in HDAC4 hyperphosphorylation and decreases it's nuclear localization, thus the histones of it's target genes remain acetylated and transcriptionally active which drives excessive collagen secretion from IPF fibroblasts. Thus PP2A activation, by promoting HDAC4 nuclear translocation, will suppress excessive the excessive collagen secretion characteristic of IPF and other systemic fibrotic diseases. 3. Activated phosph-ERK is a direct target of PP2A, which it dephosphorylates and deactivates. In scleroderma fibroblasts TGFb reduces PP2A activity and promotes ERK signaling and excessive collagen production. Activation of PP2A will suppress this signaling pathway from TGFb, a known and important pro-fibrotic cytokine. It is reasonable to conjecture that a similar pathway is operative in lung fibroblasts in IPF, thus PP2A activation should be useful there also. 4. PP2A negatively regulates Wnt/b-catenin signaling. Wnt3a induces lung epithelial cell proliferation, fibroblast activation and collagen synthesis in IPF. PP2A activation will suppress these processes and thus exert a therapeutic benefit in lung fibrosis and IPF. In summary, PP2A is involved in several major signaling pathways implicated in the pathogenesis of lung fibrosis and IPF and in all the cases cited above PP2A activation is likely to exert a beneficial therapeutic effect. This implies that a well tolerated, effective, small molecule PP2A activator would constitute a novel therapeutic for lung fibrosis.

Impaired PP2A/AKT signaling has been observed in cellular models of idiopathic pulmonary hypertension, where it causes obstructive hyperproliferation and apoptosis resistance of distal pulmonary artery smooth muscle cells. Increasing PP2A activity may reverse this, thus, treatment with compounds of the present invention may be an effective treatment for pulmonary hypertension.

Further provided herein is a method for treating cardiac hypertrophy in a patient by administering to the patient a therapeutically effective amount of a compound of formula I. In some embodiments, the cardiac hypertrophy is associated with a disease selected from hypertension, myocardial infarction, heart failure, and valvular heart disease. Cardiac physiology and hypertrophy are regulated by the phosphorylation status of many proteins, including receptors and ion channels, which is partly controlled by a PP2A-alpha4 intracellular signalling axis. Studies indicate that the type 2A protein phosphatases are differentially regulated in both the healthy and hypertrophied myocardium. The data suggest that pressure overload-induced hypertrophy is associated with (1) altered expression of type 2A protein phosphatases and their regulatory subunits and (2) an increase in expression of their non-catalytic inhibitor protein alpha4. Thus, treatment with compounds of the present invention may ameliorate cardiac hypertrophy. Also, significant reduction in endosomal PP2A activity has been observed in heart failure samples versus controls, suggesting that inhibited resensitization of beta-adrenergic receptors occurs in human heart failure. These studies suggest that resensitization of beta adrenergic receptors is inhibited in human heart failure and targeting the PP2A inhibitor SET to derepress and activate PP2A may provide preservation of receptor function and beneficial cardiac remodeling. Thus, treatment with compounds of the present invention may have a beneficial effect in heart failure.

Further provided herein is a method for treating a parasitic infection in a patient by administering to the patient a therapeutically effective amount of a compound of formula I. Examples of parasites that may cause parasitic infections to be treated include, but are not limited to, *Plasmodium* and *Theileria*.

Further provided herein is a method for treating inflammatory conditions. Reduced PP2A activity occurs in animal models of allergic airway disease and patients with severe asthma. Treatment with small molecule activators of PP2A such as fingolimod (FTY720) or 2-amino-4-(4-(heptyloxy) phenyl)-2-methylbutan-1-ol (AAL(S)) inhibited the development of inflammation, airway hyperreactivity in mouse models of allergic airway disease. Thus, compounds of the present invention may be useful in the treatment of asthma. Dephosphorylation of tristetraprolin (TTP) functions as an "off-switch" in inflammatory responses, and its activity can be promoted by compounds that stimulate PP2A activity. Therapeutic efficacy of protein phosphatase 2A (PP2A)-activating drugs, to target tristetraprolin (TTP), in models of rheumatoid arthritis has been demonstrated in vitro and in vivo. Thus, treatment with compounds of the present invention may be useful in chronic inflammatory conditions such as rheumatoid arthritis.

PP2A enzymes are involved in the regulation of cell transcription, cell cycle, and viral transformation. Many viruses, including cytomegalovirus, parainfluenza, DNA tumor viruses, and HIV-1, utilize different approaches to exploit PPA2 in order to modify, control, or inactivate cellular activities of the host [Garcia et al., Microbes and Infection, 2, 2000, 401-407]. Therefore, the compounds provided herein may further be used in a method for treating a viral infection in a patient by administering to the patient a therapeutically effective amount of a compound of formula I. Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

Serine/Threonine phosphatases, including PP2A, are involved in modulation of synaptic plasticity (D. G. Winder and J. D. Sweatt, Nature Reviews Neuroscience, vol 2, July 2001, pages 461-474). Persistently decreased PP2A activity is associated with maintenance of Long Term Potentiation (LTP) of synapses, thus treatment PP2A activators such as those described here may reverse synaptic LTP. Psychostimulant drugs of abuse such as cocaine and methamphetamine are associated with deleterious synaptic LTP (L. Mao et al, Neuron 67, Sep. 9, 2010 and A. Stipanovich et al, Nature vol 453, 2008, pages 879-884), which may underlie the pathology of addiction and relapse therefore PP2A activators described here may be useful as treatments for psychostimulant abuse.

Abnormalities in synaptic structure and signaling are linked to autistic spectrum disorder, see for example, Y Chen et al., CTTNBP2, but not CTTNBP2NL, regulates dendritic spinogenesis and synaptic distribution of the striatin-PP2A complex, Molecular Biology of the Cell, 23, Nov. 15, 2012, 4383-4392. PP2A has been shown to be important in normal development of dendritic spines, and treatment with compounds of the present invention may ameliorate or reverse autistic spectrum disorder.

Further provided herein is a method for treating a disease or disorder in which the disease or disorder involves the dysregulation of the mTOR-PP2A signaling axis. Mammalian target of rapamycin (mTOR) is a serine/threonineprotein kinase that regulates cell growth, proliferation, and survival: mTOR is frequently activated in human cancers and is a commonly sought anticancer therapeutic target. PP2A is a key element in mTOR-AKT signaling during nutritional deprivation, and it has important implications in cell cycle progression and quiescence. Dysregulation of cellular metabolism is a feature of cancer, with nutrient transport defects, nutrient sensing defects, dysregulated autophagy and constitutive anabolism being common in tumors; aberrant activation of mTOR is implicated in all of these processes and PP2A activation has been demonstrated to modulate them in vivo. PP2A has been shown to be involved in regulatory feedback loops with mTOR, and PP2A activators of the present invention would be expected to affect these processes directly by interacting with mTOR complexes, or indirectly by counterbalancing mTOR's effects by dephosphorylating its targets. Perturbation of the mTOR signaling cascade appears to be a common pathophysiological feature of human neurological disorders, including mental retardation syndromes and autism spectrum disorders, and neurodegenerative conditions such as Alzhiemer's disease. Activation of PP2A has been shown to be effective in animal models of neurodegenerative disease by modulating the PP2A mTOR axis; thus, molecules of the present invention will be useful in treatment of these conditions. PP2A activators of the present invention are likely to be useful in the treatment of diseases in which mTOR signaling is dysregulated; these include cancer, diabetes and neurodegenerative conditions. Compounds of the present invention may also promote innate immunity to infection and promote healthy aging.

Provided herein are methods of treating a disease in a subject in need thereof, the disease chosen from:
(a) cancer; (b) diabetes; (c) autoimmune disease, such as rheumatoid arthritis or multiple sclerosis; (d) age onset proteotoxic disease, particularly neurodegenerative disease; (e) mood disorder; (f) acne vulgaris; (g) solid organ transplant rejection (graft vs. host disease); (h) pulmonary disease, such as COPD or pulmonary fibrosis; (i) cardiac hypertrophy and heart failure; (j) viral or parasitic infection; and (k) inflammatory conditions, such as asthma;
the method comprising administering to the subject a therapeutically effective amount of a compound, composition, or pharmaceutical composition provided herein.

In some embodiments, said cancer is selected from the group consisting of: ovarian, endometrial, pancreatic, renal cell, breast, prostate, lung, hepatocellular carcinoma, glioma, leukemia, lymphoma, colorectal cancers, and sarcomas.

In some embodiments, said cancer is chemotherapy resistant cancer.

In some embodiments, the method further comprises administering one or more additional cancer chemotherapeutic agents.

In some embodiments, the age onset proteotoxic disease is a neurodegenerative disease.

In some embodiments, the neurodegenerative disease is Alzheimer's disease, Parkinson's disease, Huntington's disease, or amyotrophic lateral sclerosis.

In some embodiments, the disease is a pulmonary disease.

In some embodiments, the pulmonary disease is COPD, asthma or pulmonary fibrosis.

In some embodiments, the disease is an inflammatory or autoimmune disease.

In some embodiments, the inflammatory or autoimmune disease is multiple sclerosis.

Also provided herein are methods for restoring sensitivity to one or more chemotherapeutic agents in the treatment of cancer in a subject in need thereof, the method comprising administering an effective amount of a compound, composition, or pharmaceutical composition provided herein.

Also provided herein are methods for treating a disease or disorder in a subject in need thereof where the disease or disorder involves the dysregulation of the PI3K-AKT-FOXO signaling pathway, the method comprising administering to the subject a therapeutically effective amount of a compound, composition, or pharmaceutical composition provided herein.

Also provided herein are methods for treating a disease or disorder in a subject in need thereof where the disease or disorder involves the dysregulation of a Myc dependent signaling pathway, the method comprising administering to the subject a therapeutically effective amount of a compound, composition, or pharmaceutical composition provided herein.

Also provided herein are methods for treating a metabolic or neurological disease or disorder in a subject in need thereof wherein the disease or disorder involves the dysregulation of the mTOR-PP2A signaling axis, the method comprising administering to the subject a therapeutically effective amount of a compound, composition, or pharmaceutical composition provided herein.

Also provided herein are methods of inhibiting proliferation of a cell, comprising contacting the cell with an effective amount of a compound, composition, or pharmaceutical composition provided herein. In some embodiments, the inhibition is in vitro inhibition. In some embodiments, the inhibition is in vivo inhibition in a subject in need thereof.

Abbreviations and Definitions

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the Journal of Organic Chemistry. The list, which is typically presented in a table entitled "Standard List of Abbreviations" is incorporated herein by reference. In the event that there is a plurality of definitions for terms cited herein, those in this section prevail unless otherwise stated.

The following abbreviations and terms have the indicated meanings throughout:
Ac=acetyl
Aq=aqueous
Boc=t-butyloxy carbonyl
Bu=butyl
c-=cyclo
cat=catalyst
Cbz=carboxybenzyl
DBA=dibenzylideneacetone
DCM=dichloromethane=methylene chloride=$CH_2Cl_2$
DMF=N,N-dimethylformamide
eq. or equiv.=equivalent(s)
Et=ethyl
GC=gas chromatography
h=hour(s)
KHMDS=Potassiurm bis(urmethylsilyl)amide
Lg=leaving group
Ln=chiral ligands
mCPBA=meta-Chloroperoxybenzoic acid
Me=methyl
mesyl=methanesulfonyl
min.=minute(s)
Ms=mesylate
NMO or NMMO=N-methylmorpholine oxide
Pg=protecting group Ph=phenyl
RT=room temperature
sat'd or sat.=saturated
t- or tert=tertiary
Tf=triflate
TFA=trifluoroacetic acid
THF=tetrahydrofuran
tosyl=p-toluenesulfonyl Throughout this specification the terms and substituents retain their definitions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or composition that "comprises", "has", "includes" or "contains" one or more steps or elements possesses those one or more steps or elements, but is not limited to possessing only those one or more steps or elements. Likewise, a step of a method or an element of a composition that "comprises", "has", "includes" or "contains" one or more features possesses those one or more features, but is not limited to possessing only those one or more features. The terms "comprising" and "including" or grammatical variants thereof are to be taken as specifying the stated features, integers, steps or components but do not preclude the addition of one or more additional features, integers, steps, components or groups thereof. For example, "X includes a, b and c" means that X includes, but is not limited to, a, b and c. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

Unless otherwise specified, the phrase "such as" is intended to be open-ended. For example, "X can be a halogen, such as fluorine or chlorine" means that X can be, but is not limited to, fluorine or chlorine.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

The terms "subject" or "subject in need thereof" or "patient" are used interchangeably herein. These terms refer to a patient who has been diagnosed with the underlying disorder to be treated. The subject may currently be experiencing symptoms associated with the disorder or may have experienced symptoms in the past. Additionally, a "subject in need thereof" may be a patient at risk of developing a particular disease, or to a patient reporting one or more of the physiological systems of a disease, even though a diagnosis of this disease may not have been made. As a non-limiting example, a "subject in need thereof", for purposes of this application, may include a male who is currently diagnosed with prostate cancer or was diagnosed with prostate cancer in the past, regardless of current symptomatology.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

As used herein, the terms "treatment" or "treating" are used interchangeably. These terms refer to an approach for obtaining beneficial or desired results including, but not limited to, therapeutic benefit. Therapeutic benefit includes eradication or amelioration of the underlying disorder being treated; it also includes the eradication or amelioration of one or more of the symptoms associated with the underlying disorder such that an improvement is observed in the patient, notwithstanding that the patient may still be afflicted with the underlying disorder.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "modulate" with respect to a FOXO transcription factor protein refers to activation of the FOXO transcription factor protein and its biological activities associated with the FOXO pathway. Modulation of FOXO transcription factor proteins includes up-regulation (i.e., agonizing, activation or stimulation). The mode of action of a FOXO modulator can be direct, e.g., through binding to the FOXO transcription factor protein as a ligand. The modulation can also be indirect, e.g., through binding to and/or modifying another molecule which otherwise binds to and activates the FOXO transcription factor protein.

"Hydrocarbon" (e.g., ($C_1$-$C_8$)hydrocarbon) includes alkyl, cycloalkyl, polycycloalkyl, alkenyl, alkynyl, aryl and combinations thereof. Examples include benzyl, phenethyl, cyclohexylmethyl, adamantyl, norbornyl, and naphthylethyl. Hydrocarbyl (or hydrocarbon) refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

The terms "haloalkyl," "haloalkoxy," or "haloalkylthio" mean alkyl, alkoxy, or alkylthio, respectively, substituted with one or more halogen atoms.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl. Examples of heteroaryls include imidazole, pyridine, indole, thiophene, benzopyranone, thiazole, furan, benzimidazole, quinoline, isoquinoline, quinoxaline, pyrimidine, pyrazine, tetrazole and pyrazole. In some embodiments, examples of heteroaryls include imidazole, pyridine, thiophene, thiazole, furan, pyrimidine, pyrazine, tetrazole and pyrazole.

As used herein, the term "optionally substituted" may be used interchangeably with "unsubstituted or substituted". The term "substituted" refers to the replacement of one or more hydrogen atoms in a specified group with a specified radical. "Oxo" may also be included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine.

TABLE 1

Examples

| Example No. | Structure | Synthesis scheme |
|---|---|---|
| 1a | ![structure] | SCHEME C1 |

TABLE 1-continued

Examples

| Example No. | Structure | Synthesis scheme |
|---|---|---|
| 1b | bis(4-fluorophenyl)methyl piperidine (3S) sulfonamide N-(4-OCF₃-phenyl) | SCHEME C1 |
| 1c | bis(4-fluorophenyl)methyl piperidine (3R) sulfonamide N-(4-OCF₃-phenyl) | SCHEME C1 |
| 2 | bis(4-fluorophenyl)methyl piperidine sulfonamide N-phenyl | SCHEME C1 |
| 3 | bis(4-fluorophenyl)methyl piperidine sulfonamide N-(3-CF₃-phenyl) | SCHEME C1 |
| 4 | bis(4-fluorophenyl)methyl piperidine sulfonamide N-(4-CF₃-phenyl) | SCHEME C1 |

TABLE 1-continued

| Example No. | Structure | Synthesis scheme |
|---|---|---|
| 5 | 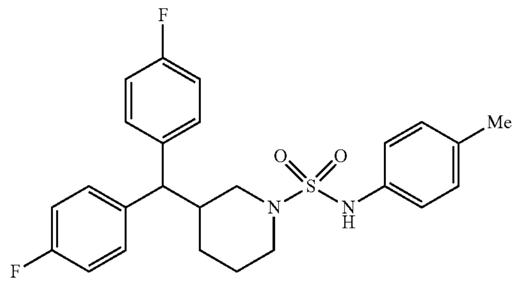 [SMILES: Cc1ccc(NS(=O)(=O)N2CCCC(C(c3ccc(F)cc3)c3ccc(F)cc3)C2)cc1] | SCHEME C1 |
| 6 | 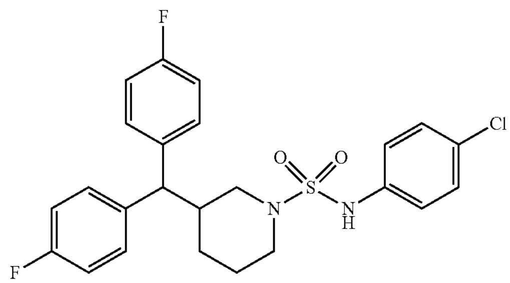 [SMILES: O=S(=O)(Nc1ccc(Cl)cc1)N1CCCC(C(c2ccc(F)cc2)c2ccc(F)cc2)C1] | SCHEME C1 |
| 7 | 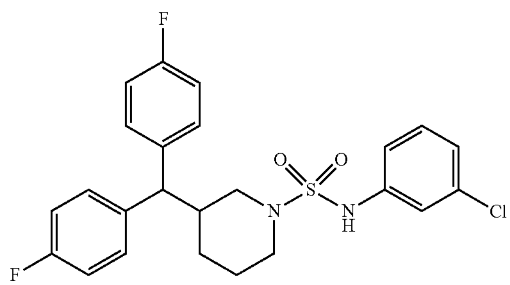 [SMILES: O=S(=O)(Nc1cccc(Cl)c1)N1CCCC(C(c2ccc(F)cc2)c2ccc(F)cc2)C1] | SCHEME C1 |
| 8 | 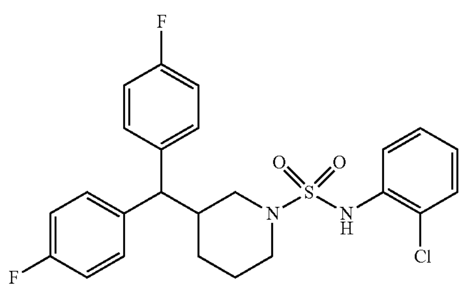 [SMILES: O=S(=O)(Nc1ccccc1Cl)N1CCCC(C(c2ccc(F)cc2)c2ccc(F)cc2)C1] | SCHEME C1 |
| 9 | 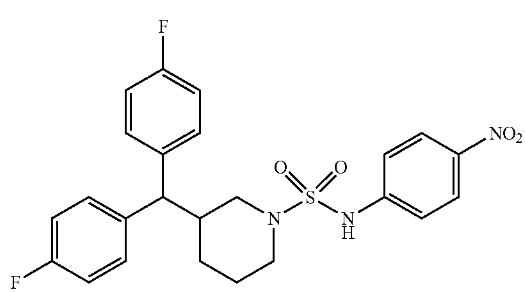 [SMILES: O=[N+]([O-])c1ccc(NS(=O)(=O)N2CCCC(C(c3ccc(F)cc3)c3ccc(F)cc3)C2)cc1] | SCHEME C1 |

TABLE 1-continued

| Example No. | Structure | Synthesis scheme |
|---|---|---|
| 10 | 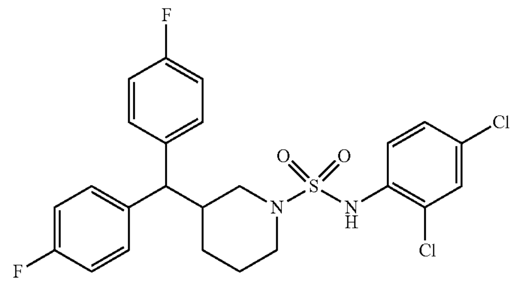 [SMILES: O=S(=O)(Nc1ccc(Cl)cc1Cl)N1CCCC(C(c2ccc(F)cc2)c2ccc(F)cc2)C1] | SCHEME C1 |
| 11 | 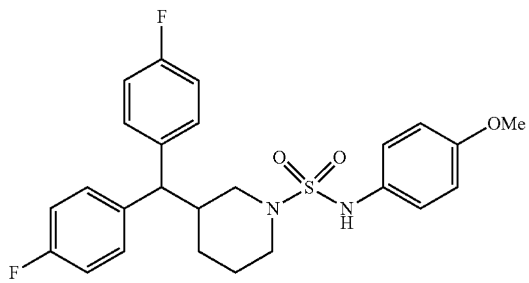 [SMILES: COc1ccc(NS(=O)(=O)N2CCCC(C(c3ccc(F)cc3)c3ccc(F)cc3)C2)cc1] | SCHEME C1 |
| 12 | 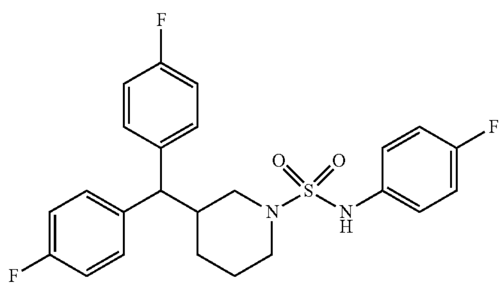 [SMILES: O=S(=O)(Nc1ccc(F)cc1)N1CCCC(C(c2ccc(F)cc2)c2ccc(F)cc2)C1] | SCHEME C1 |
| 13 | 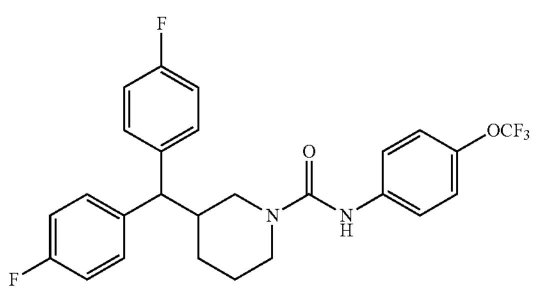 [SMILES: O=C(Nc1ccc(OC(F)(F)F)cc1)N1CCCC(C(c2ccc(F)cc2)c2ccc(F)cc2)C1] | SCHEME C2 |
| 14 | 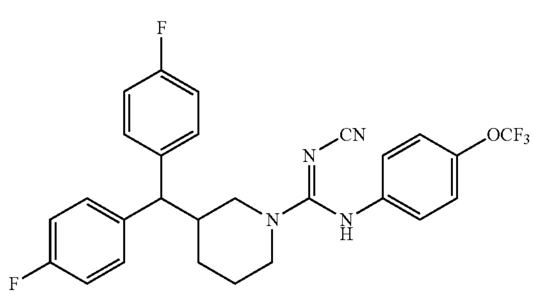 [SMILES: N#C/N=C(\Nc1ccc(OC(F)(F)F)cc1)N1CCCC(C(c2ccc(F)cc2)c2ccc(F)cc2)C1] | SCHEME C3 |

TABLE 1-continued

| Example No. | Structure | Synthesis scheme |
|---|---|---|
| 15 | 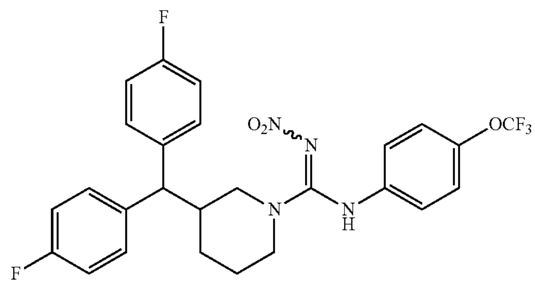 [SMILES: O=[N+]([O-])N=C(Nc1ccc(OC(F)(F)F)cc1)N1CCCC(C(c2ccc(F)cc2)c2ccc(F)cc2)C1] | SCHEME C3 |
| 16 | 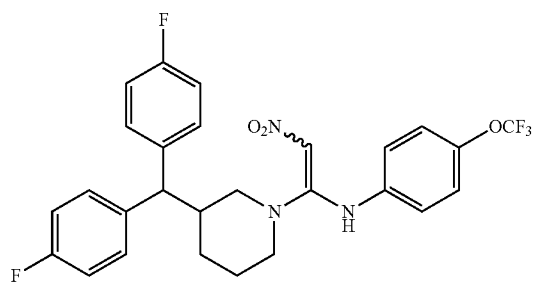 [SMILES: O=[N+]([O-])C=C(Nc1ccc(OC(F)(F)F)cc1)N1CCCC(C(c2ccc(F)cc2)c2ccc(F)cc2)C1] | SCHEME C3 |
| 17 | 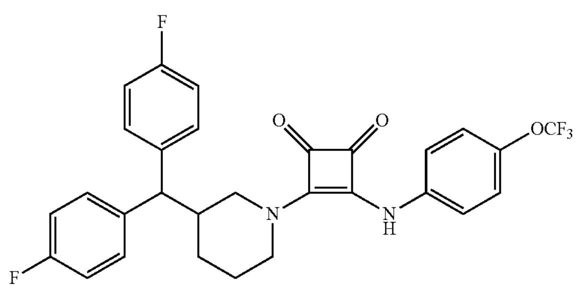 [SMILES: O=c1c(Nc2ccc(OC(F)(F)F)cc2)c(N2CCCC(C(c3ccc(F)cc3)c3ccc(F)cc3)C2)c1=O] | SCHEME C4 |
| 18 | 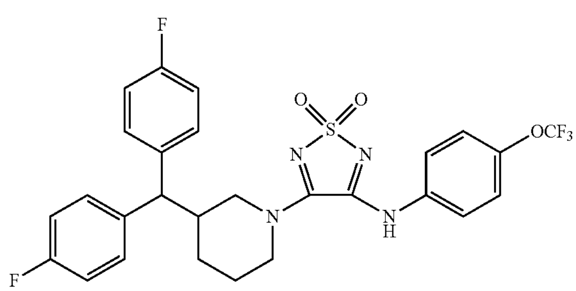 [SMILES: O=S1(=O)N=C(Nc2ccc(OC(F)(F)F)cc2)C(N2CCCC(C(c3ccc(F)cc3)c3ccc(F)cc3)C2)=N1] | SCHEME C4 |
| 19 | 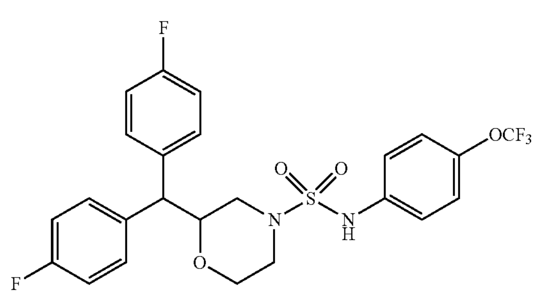 [SMILES: O=S(=O)(Nc1ccc(OC(F)(F)F)cc1)N1CCOC(C(c2ccc(F)cc2)c2ccc(F)cc2)C1] | SCHEME C5 |

TABLE 1-continued
| Example No. | Structure | Synthesis scheme |
|---|---|---|
| 20 | 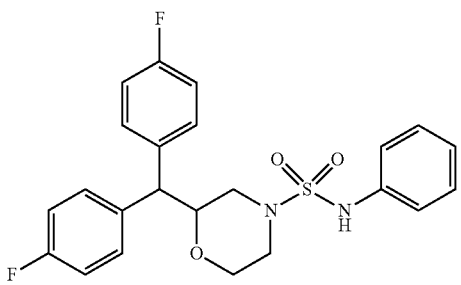 [SMILES: O=S(=O)(Nc1ccccc1)N1CCOC(C(c2ccc(F)cc2)c2ccc(F)cc2)C1] | SCHEME C5 |
| 21 | 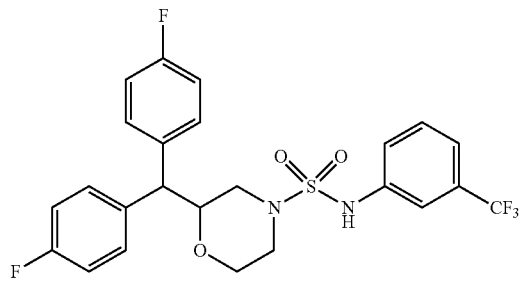 [SMILES: O=S(=O)(Nc1cccc(C(F)(F)F)c1)N1CCOC(C(c2ccc(F)cc2)c2ccc(F)cc2)C1] | SCHEME C5 |
| 22 | 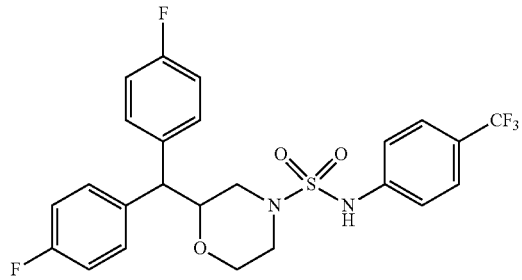 [SMILES: O=S(=O)(Nc1ccc(C(F)(F)F)cc1)N1CCOC(C(c2ccc(F)cc2)c2ccc(F)cc2)C1] | SCHEME C5 |
| 23 | 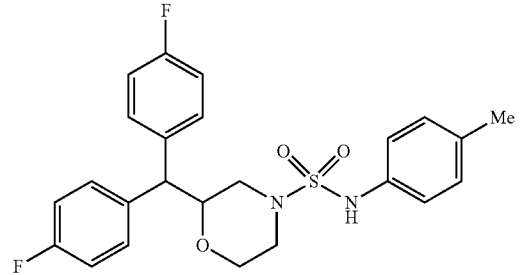 | SCHEME C5 |
| 24 | 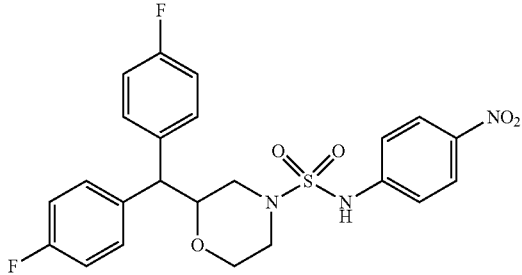 | SCHEME C5 |

TABLE 1-continued

| Example No. | Structure | Synthesis scheme |
|---|---|---|
| 25 | 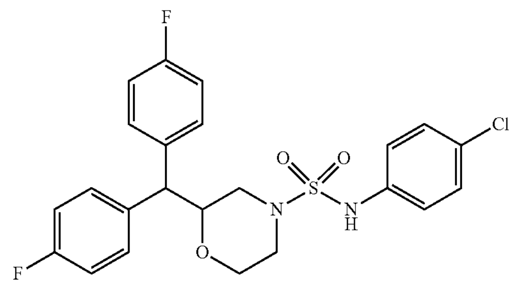 [SMILES: O=S(=O)(Nc1ccc(Cl)cc1)N1CCOC(C(c2ccc(F)cc2)c2ccc(F)cc2)C1] | SCHEME C5 |
| 26 | 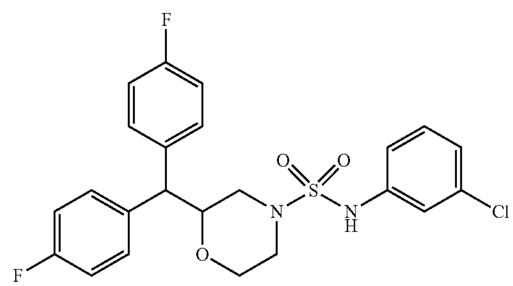 [SMILES: O=S(=O)(Nc1cccc(Cl)c1)N1CCOC(C(c2ccc(F)cc2)c2ccc(F)cc2)C1] | SCHEME C5 |
| 27 | 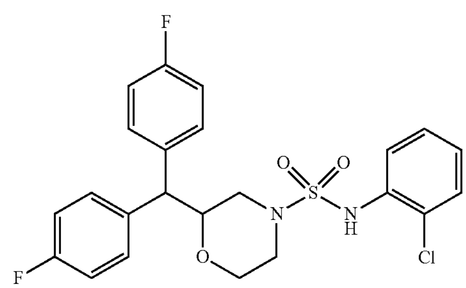 [SMILES: O=S(=O)(Nc1ccccc1Cl)N1CCOC(C(c2ccc(F)cc2)c2ccc(F)cc2)C1] | SCHEME C5 |
| 28 | 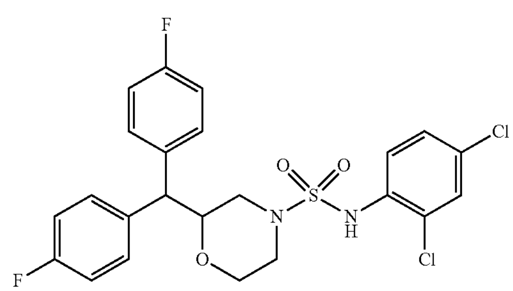 [SMILES: O=S(=O)(Nc1ccc(Cl)cc1Cl)N1CCOC(C(c2ccc(F)cc2)c2ccc(F)cc2)C1] | SCHEME C5 |
| 29 | 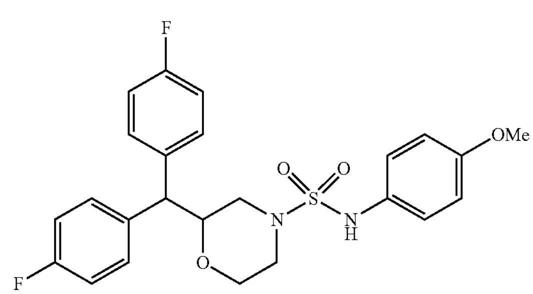 [SMILES: COc1ccc(NS(=O)(=O)N2CCOC(C(c3ccc(F)cc3)c3ccc(F)cc3)C2)cc1] | SCHEME C5 |

TABLE 1-continued

| Example No. | Structure | Synthesis scheme |
|---|---|---|
| 30 | 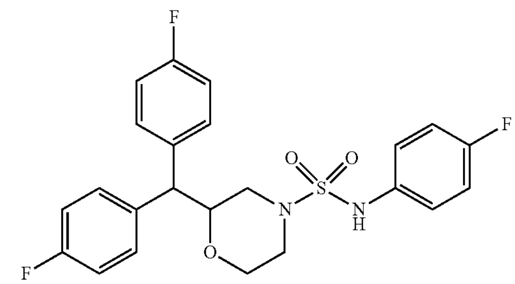 [SMILES: O=S(=O)(Nc1ccc(F)cc1)N1CCOC(C(c2ccc(F)cc2)c2ccc(F)cc2)C1] | SCHEME C5 |
| 31 | 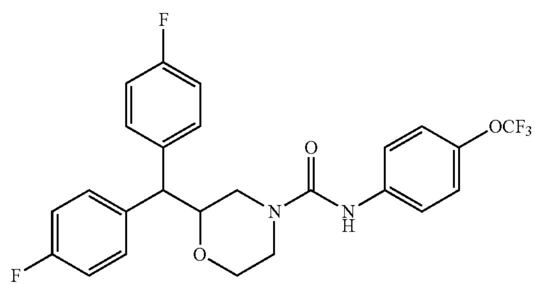 [SMILES: O=C(Nc1ccc(OC(F)(F)F)cc1)N1CCOC(C(c2ccc(F)cc2)c2ccc(F)cc2)C1] | Method of SCHEME C2 |
| 32 | 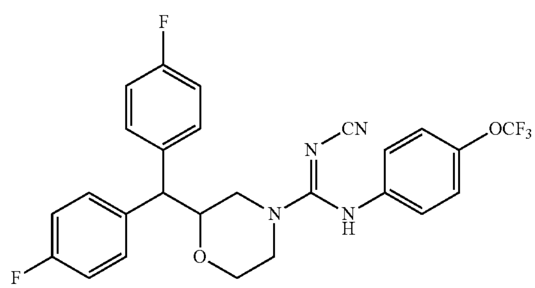 [SMILES: N#C/N=C(\Nc1ccc(OC(F)(F)F)cc1)N1CCOC(C(c2ccc(F)cc2)c2ccc(F)cc2)C1] | Method of SCHEME C3 |
| 33 | 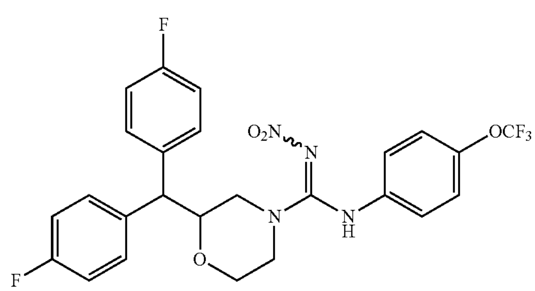 [SMILES: O=[N+]([O-])N=C(Nc1ccc(OC(F)(F)F)cc1)N1CCOC(C(c2ccc(F)cc2)c2ccc(F)cc2)C1] | Method of SCHEME C3 |
| 34 | 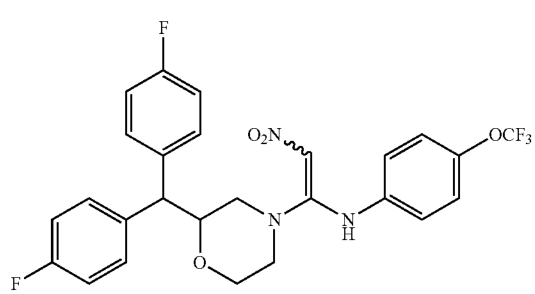 [SMILES: O=[N+]([O-])C=C(Nc1ccc(OC(F)(F)F)cc1)N1CCOC(C(c2ccc(F)cc2)c2ccc(F)cc2)C1] | Method of SCHEME C3 |

TABLE 1-continued

Examples

| Example No. | Structure | Synthesis scheme |
|---|---|---|
| 35 | 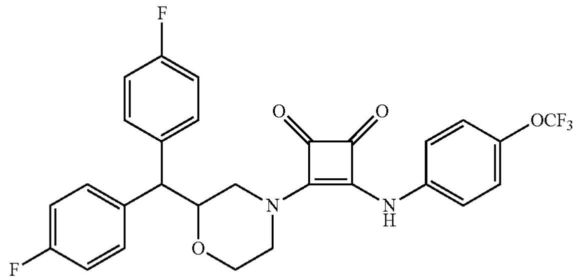 [SMILES: O=c1c(Nc2ccc(OC(F)(F)F)cc2)c(N2CCOC(C(c3ccc(F)cc3)c3ccc(F)cc3)C2)c1=O] | Method of SCHEME C3 |
| 36 | 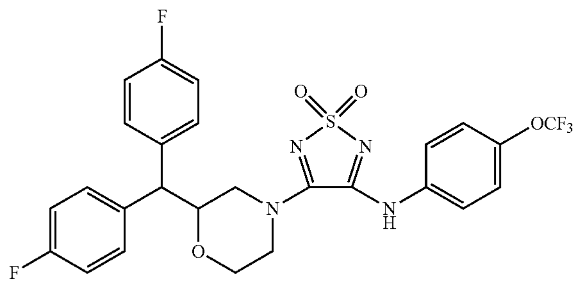 [SMILES: O=S1(=O)N=C(Nc2ccc(OC(F)(F)F)cc2)C(N2CCOC(C(c3ccc(F)cc3)c3ccc(F)cc3)C2)=N1] | Method of SCHEME C4 |
| 37 | 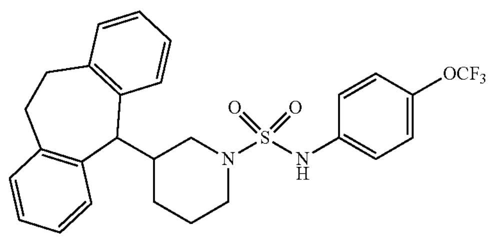 [SMILES: O=S(=O)(Nc1ccc(OC(F)(F)F)cc1)N1CCCC(C2c3ccccc3CCc3ccccc32)C1] | Method of SCHEME C4 |
| 38 | 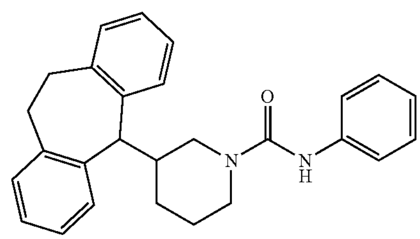 [SMILES: O=C(Nc1ccccc1)N1CCCC(C2c3ccccc3CCc3ccccc32)C1] | SCHEME D1 |
| 39 | 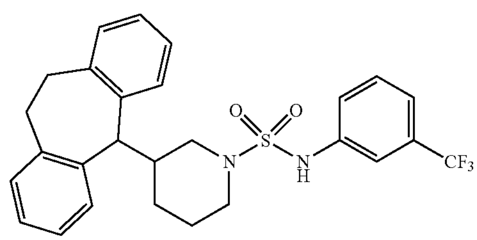 [SMILES: O=S(=O)(Nc1cccc(C(F)(F)F)c1)N1CCCC(C2c3ccccc3CCc3ccccc32)C1] | SCHEME D1 |
| 40 | 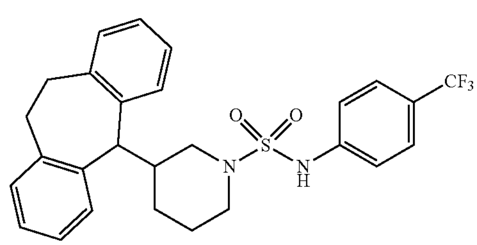 [SMILES: O=S(=O)(Nc1ccc(C(F)(F)F)cc1)N1CCCC(C2c3ccccc3CCc3ccccc32)C1] | SCHEME D1 |

TABLE 1-continued

| Example No. | Structure | Synthesis scheme |
|---|---|---|
| 41 | 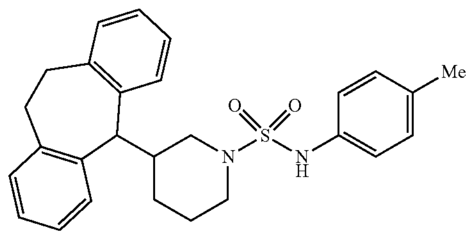 [SMILES: Cc1ccc(NS(=O)(=O)N2CCCC(C3c4ccccc4CCc4ccccc43)C2)cc1] | SCHEME D1 |
| 42 | 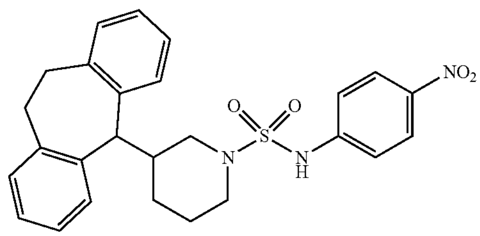 [SMILES: O=[N+]([O-])c1ccc(NS(=O)(=O)N2CCCC(C3c4ccccc4CCc4ccccc43)C2)cc1] | SCHEME D1 |
| 43 | 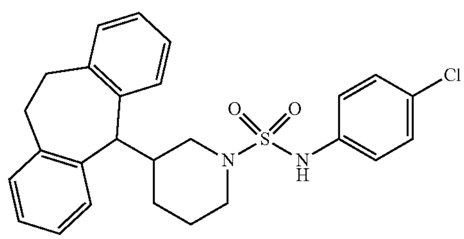 [SMILES: O=S(=O)(Nc1ccc(Cl)cc1)N1CCCC(C2c3ccccc3CCc3ccccc32)C1] | SCHEME D1 |
| 44 | 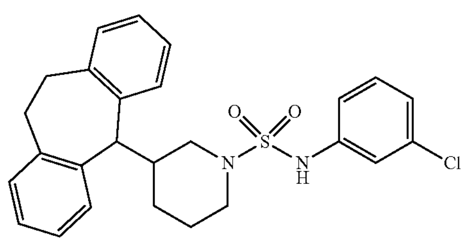 [SMILES: O=S(=O)(Nc1cccc(Cl)c1)N1CCCC(C2c3ccccc3CCc3ccccc32)C1] | SCHEME D1 |
| 45 | 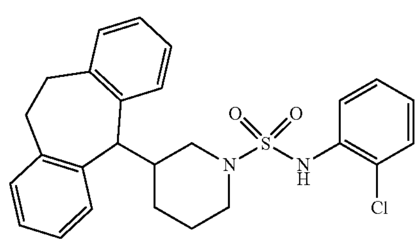 [SMILES: O=S(=O)(Nc1ccccc1Cl)N1CCCC(C2c3ccccc3CCc3ccccc32)C1] | SCHEME D1 |
| 46 | 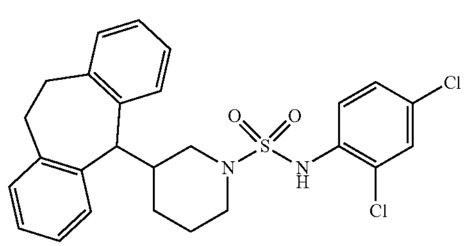 [SMILES: O=S(=O)(Nc1ccc(Cl)cc1Cl)N1CCCC(C2c3ccccc3CCc3ccccc32)C1] | SCHEME D1 |

TABLE 1-continued

Examples

| Example No. | Structure | Synthesis scheme |
|---|---|---|
| 47 | 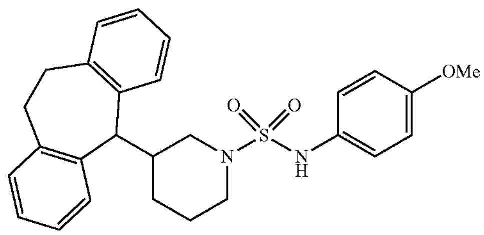 [SMILES: COc1ccc(NS(=O)(=O)N2CCCC(C3c4ccccc4CCc4ccccc43)C2)cc1] | SCHEME D1 |
| 48 | 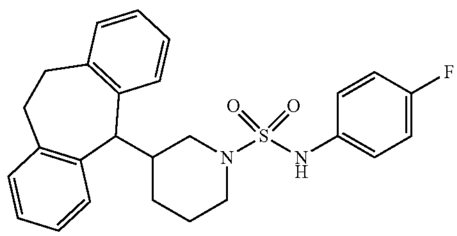 [SMILES: O=S(=O)(Nc1ccc(F)cc1)N1CCCC(C2c3ccccc3CCc3ccccc32)C1] | SCHEME D1 |
| 49 | 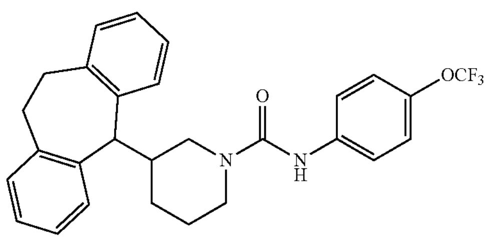 [SMILES: O=C(Nc1ccc(OC(F)(F)F)cc1)N1CCCC(C2c3ccccc3CCc3ccccc32)C1] | See methods of SCHEME C2 |
| 50 | 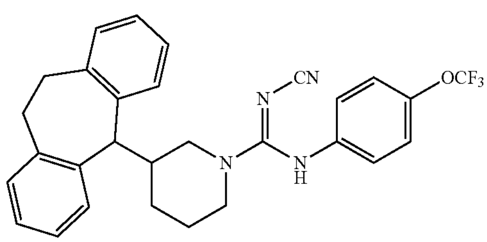 [SMILES: N#C/N=C(\Nc1ccc(OC(F)(F)F)cc1)N1CCCC(C2c3ccccc3CCc3ccccc32)C1] | See methods of SCHEME C3 |
| 51 | 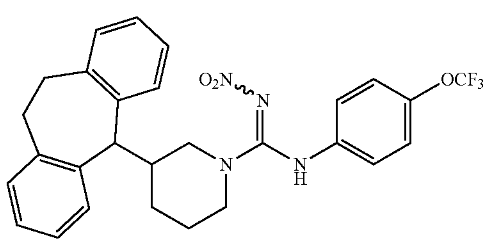 [SMILES: O=[N+]([O-])N=C(Nc1ccc(OC(F)(F)F)cc1)N1CCCC(C2c3ccccc3CCc3ccccc32)C1] | See methods of SCHEME C3 |
| 52 | 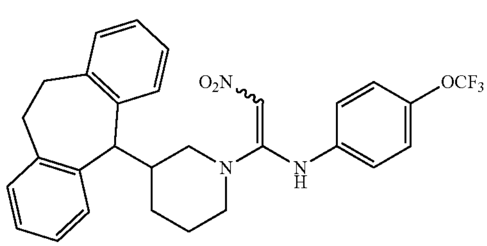 [SMILES: O=[N+]([O-])C=C(Nc1ccc(OC(F)(F)F)cc1)N1CCCC(C2c3ccccc3CCc3ccccc32)C1] | See methods of SCHEME C3 |

TABLE 1-continued

Examples

| Example No. | Structure | Synthesis scheme |
|---|---|---|
| 53 | 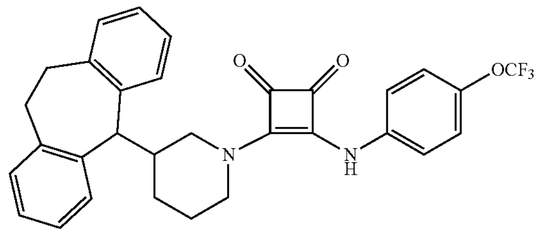 [SMILES: O=c1c(Nc2ccc(OC(F)(F)F)cc2)c(N2CCCC(C3c4ccccc4CCc4ccccc43)C2)c1=O] | See methods of SCHEME C4 |
| 54 | 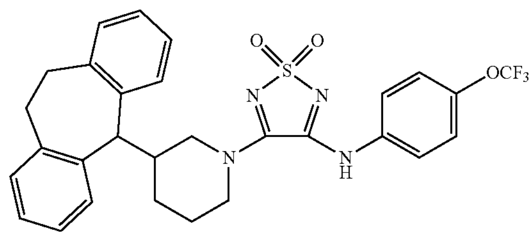 [SMILES: O=S1(=O)N=C(Nc2ccc(OC(F)(F)F)cc2)C(N2CCCC(C3c4ccccc4CCc4ccccc43)C2)=N1] | See methods of SCHEME C3 |
| 55 | 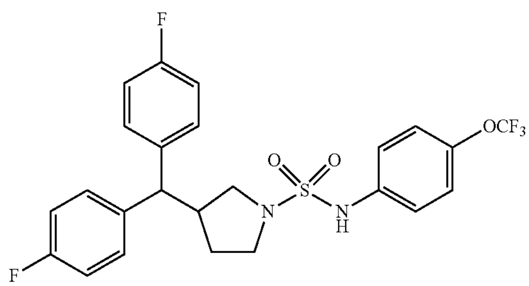 [SMILES: O=S(=O)(Nc1ccc(OC(F)(F)F)cc1)N1CCC(C(c2ccc(F)cc2)c2ccc(F)cc2)C1] | SCHEME C6 |
| 56 | 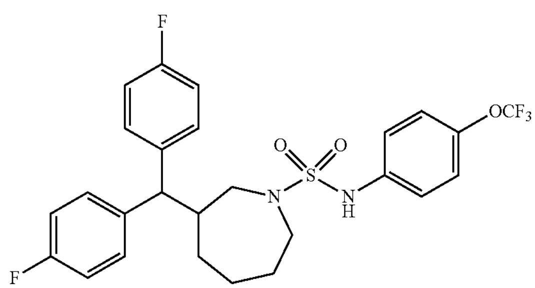 [SMILES: O=S(=O)(Nc1ccc(OC(F)(F)F)cc1)N1CCCCC(C(c2ccc(F)cc2)c2ccc(F)cc2)C1] | SCHEME C6 |
| 57 | 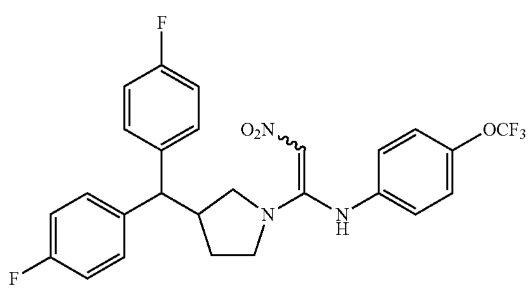 [SMILES: O=[N+]([O-])C=C(Nc1ccc(OC(F)(F)F)cc1)N1CCC(C(c2ccc(F)cc2)c2ccc(F)cc2)C1] | See methods of SCHEME C3 |

TABLE 1-continued

Examples

| Example No. | Structure | Synthesis scheme |
|---|---|---|
| 58 | 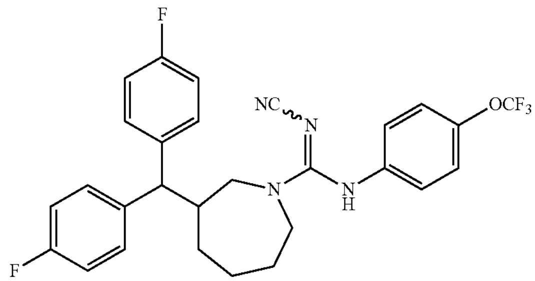 [SMILES: N#CN=C(Nc1ccc(OC(F)(F)F)cc1)N1CCCCC(C(c2ccc(F)cc2)c2ccc(F)cc2)C1] | See methods of SCHEME C3 |
| 59 | 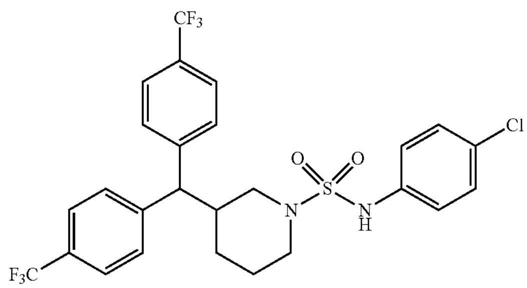 [SMILES: O=S(=O)(Nc1ccc(Cl)cc1)N1CCCC(C(c2ccc(C(F)(F)F)cc2)c2ccc(C(F)(F)F)cc2)C1] | See Methods of SCHEME C1 |
| 60 | 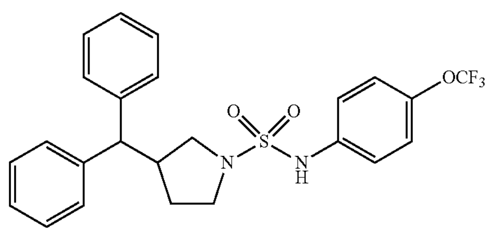 [SMILES: O=S(=O)(Nc1ccc(OC(F)(F)F)cc1)N1CCC(C(c2ccccc2)c2ccccc2)C1] | See methods of SCHEME C6 |
| 61 | 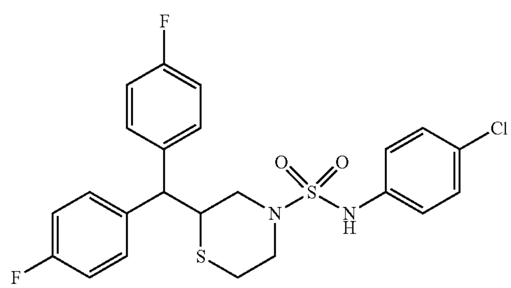 | See methods of SCHEME C5 |
| 63 | | SCHEME B3 nd methods of SCHEME C5 |
| 63 | | See SCHEME B4 and methods of SCHEME C1 |

TABLE 1-continued

| Example No. | Structure | Synthesis scheme |
|---|---|---|
| 64 | 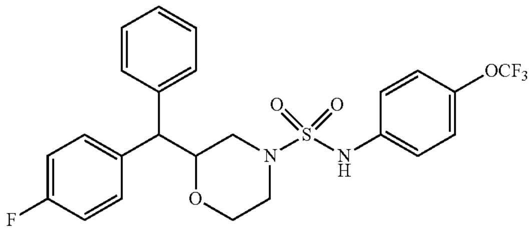 [SMILES: O=S(=O)(Nc1ccc(OC(F)(F)F)cc1)N1CCOC(C(c2ccccc2)c2ccc(F)cc2)C1] | SCHEME C7 |
| 65 | 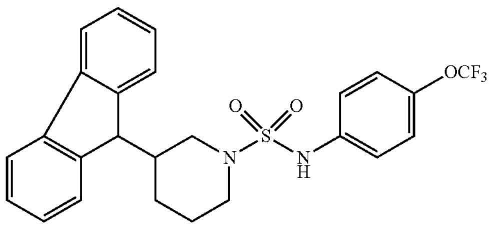 [SMILES: O=S(=O)(Nc1ccc(OC(F)(F)F)cc1)N1CCCC(C2c3ccccc3-c3ccccc32)C1] | SCHEME D2 |
| 66 | 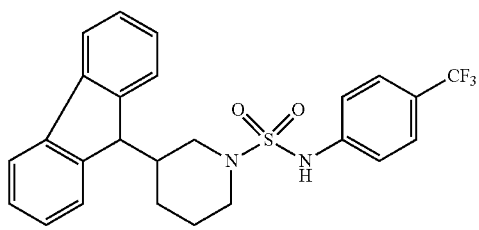 [SMILES: O=S(=O)(Nc1ccc(C(F)(F)F)cc1)N1CCCC(C2c3ccccc3-c3ccccc32)C1] | Method of SCHEME D2 |
| 67 | 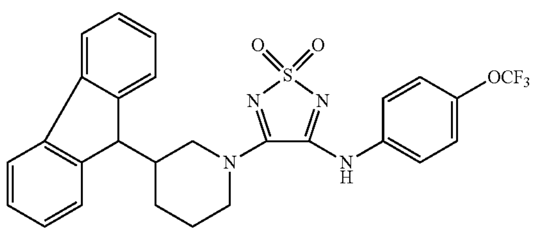 [SMILES: O=S1(=O)N=C(Nc2ccc(OC(F)(F)F)cc2)C(N2CCCC(C3c4ccccc4-c4ccccc43)C2)=N1] | SCHEME D2 and methods of SCHEME C4 |
| 68 | 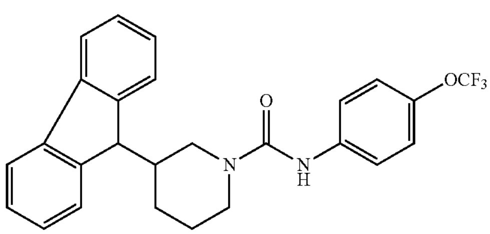 [SMILES: O=C(Nc1ccc(OC(F)(F)F)cc1)N1CCCC(C2c3ccccc3-c3ccccc32)C1] | SCHEME D2 and methods of SCHEME C4 |
| 69 | 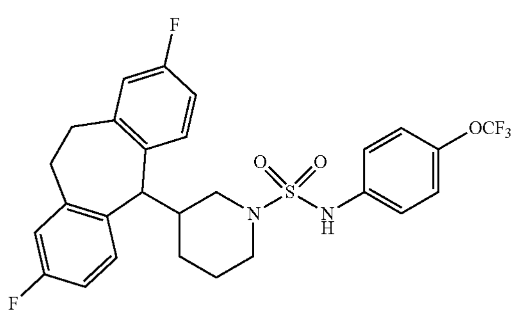 [SMILES: O=S(=O)(Nc1ccc(OC(F)(F)F)cc1)N1CCCC(C2c3ccc(F)cc3CCc3cc(F)ccc32)C1] | SCHEME D3 |

TABLE 1-continued

Examples

| Example No. | Structure | Synthesis scheme |
| --- | --- | --- |
| 70 | 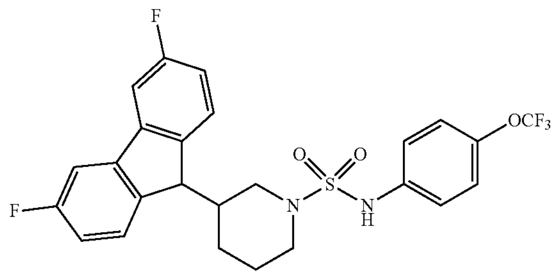 [SMILES: O=S(=O)(Nc1ccc(OC(F)(F)F)cc1)N1CCCC(C2c3ccc(F)cc3-c3cc(F)ccc32)C1] | SCHEME D3 |
| 71 | 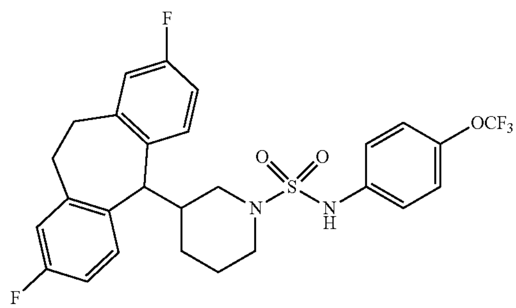 [SMILES: O=S(=O)(Nc1ccc(OC(F)(F)F)cc1)N1CCCC(C2c3ccc(F)cc3CCc3cc(F)ccc32)C1] | SCHEME D3 |
| 72 | 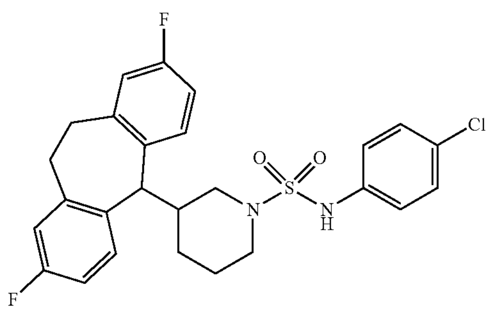 [SMILES: O=S(=O)(Nc1ccc(Cl)cc1)N1CCCC(C2c3ccc(F)cc3CCc3cc(F)ccc32)C1] | SCHEME D3 |
| 73 | 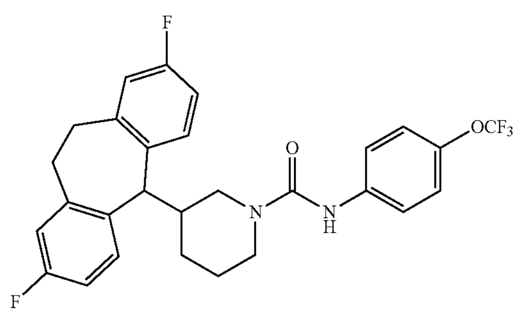 [SMILES: O=C(Nc1ccc(OC(F)(F)F)cc1)N1CCCC(C2c3ccc(F)cc3CCc3cc(F)ccc32)C1] | Method of SCHEME C2 |
| 74 | 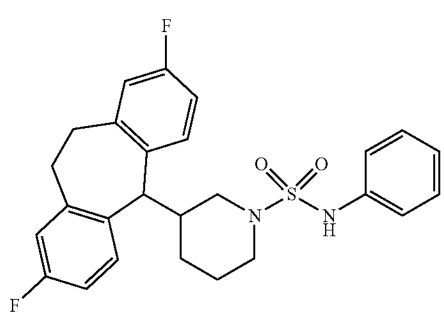 [SMILES: O=S(=O)(Nc1ccccc1)N1CCCC(C2c3ccc(F)cc3CCc3cc(F)ccc32)C1] | SCHEME D3 |

TABLE 1-continued

Examples

| Example No. | Structure | Synthesis scheme |
|---|---|---|
| 75 | 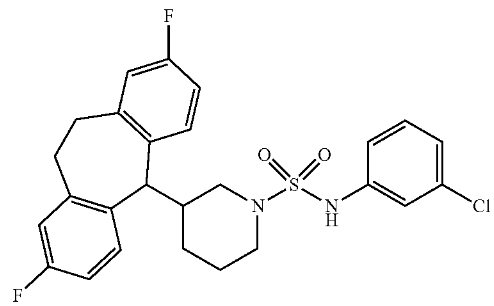 [SMILES: O=S(=O)(Nc1cccc(Cl)c1)N1CCCC(C2c3ccc(F)cc3CCc3cc(F)ccc32)C1] | SCHEME D3 |
| 76 | 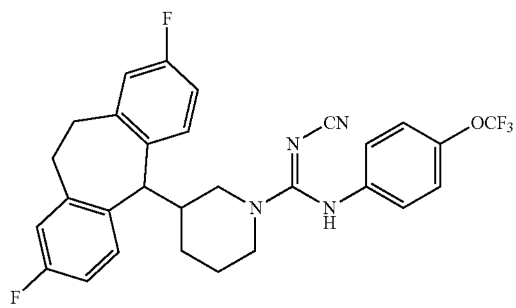 [SMILES: N#C/N=C(\Nc1ccc(OC(F)(F)F)cc1)N1CCCC(C2c3ccc(F)cc3CCc3cc(F)ccc32)C1] | Method of SCHEME C3 |
| 77 | 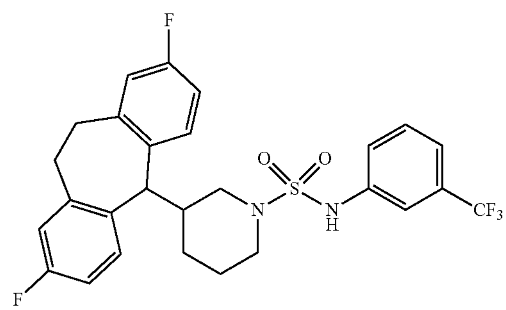 [SMILES: O=S(=O)(Nc1cccc(C(F)(F)F)c1)N1CCCC(C2c3ccc(F)cc3CCc3cc(F)ccc32)C1] | SCHEME D3 |
| 78 | 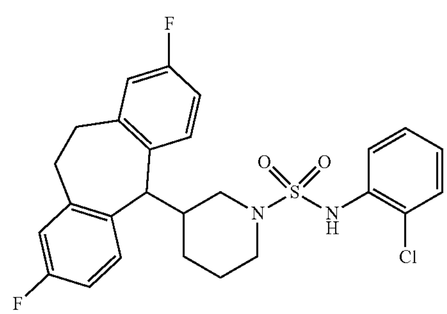 [SMILES: O=S(=O)(Nc1ccccc1Cl)N1CCCC(C2c3ccc(F)cc3CCc3cc(F)ccc32)C1] | SCHEME D3 |
| 79 | 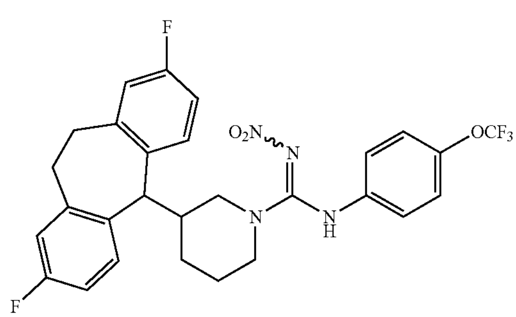 [SMILES: O=[N+]([O-])N=C(Nc1ccc(OC(F)(F)F)cc1)N1CCCC(C2c3ccc(F)cc3CCc3cc(F)ccc32)C1] | Method of SCHEME C3 |

TABLE 1-continued

Examples

| Example No. | Structure | Synthesis scheme |
|---|---|---|
| 80 | 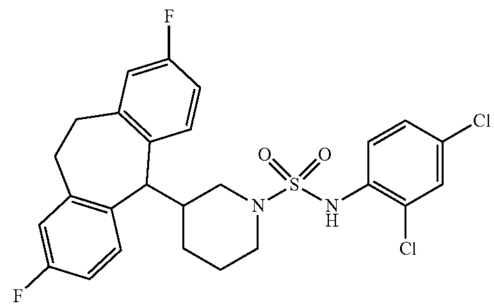 [SMILES: O=S(=O)(Nc1ccc(Cl)cc1Cl)N1CCCC(C2c3ccc(F)cc3CCc3cc(F)ccc32)C1] | SCHEME D3 |
| 81 | 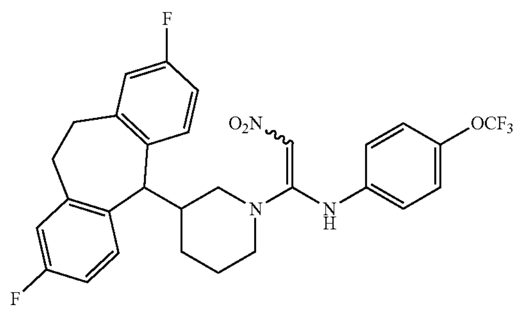 [SMILES: O=[N+]([O-])C=C(Nc1ccc(OC(F)(F)F)cc1)N1CCCC(C2c3ccc(F)cc3CCc3cc(F)ccc32)C1] | Method of SCHEME C3 |
| 82 | 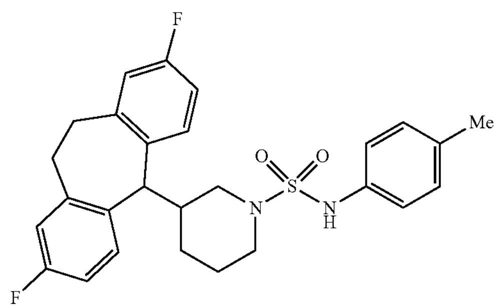 [SMILES: Cc1ccc(NS(=O)(=O)N2CCCC(C3c4ccc(F)cc4CCc4cc(F)ccc43)C2)cc1] | SCHEME D3 |
| 83 | 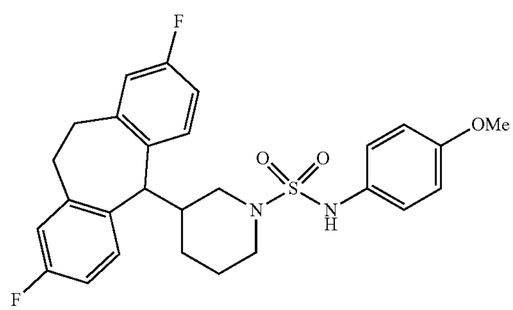 [SMILES: COc1ccc(NS(=O)(=O)N2CCCC(C3c4ccc(F)cc4CCc4cc(F)ccc43)C2)cc1] | SCHEME D3 |
| 84 | 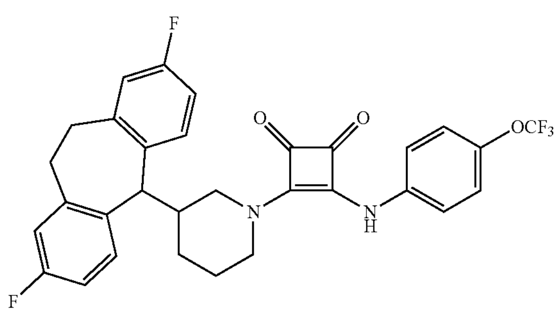 [SMILES: O=c1c(Nc2ccc(OC(F)(F)F)cc2)c(N2CCCC(C3c4ccc(F)cc4CCc4cc(F)ccc43)C2)c1=O] | Method of SCHEME C4 |

TABLE 1-continued

| Example No. | Structure | Synthesis scheme |
| --- | --- | --- |
| 85 | 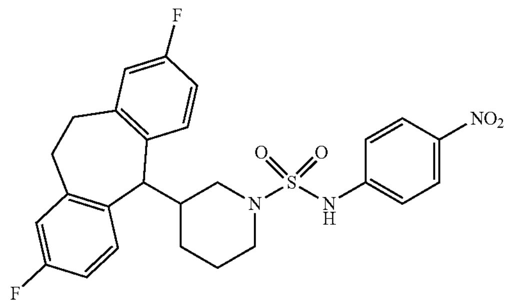 [SMILES: O=[N+]([O-])c1ccc(NS(=O)(=O)N2CCCC(C3c4ccc(F)cc4CCc4cc(F)ccc43)C2)cc1] | SCHEME D3 |
| 86 | 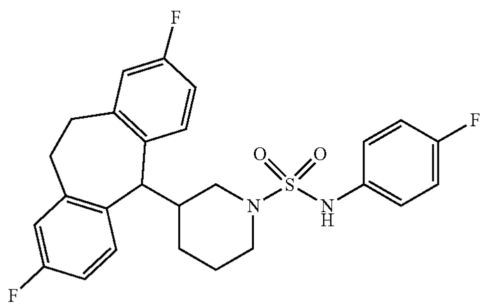 [SMILES: O=S(=O)(Nc1ccc(F)cc1)N1CCCC(C2c3ccc(F)cc3CCc3cc(F)ccc32)C1] | SCHEME D3 |
| 87 | 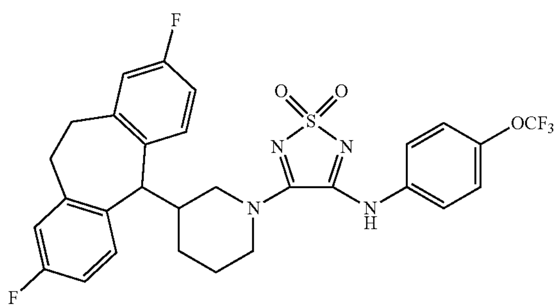 [SMILES: O=S1(=O)N=C(Nc2ccc(OC(F)(F)F)cc2)C(N2CCCC(C3c4ccc(F)cc4CCc4cc(F)ccc43)C2)=N1] | methods of SCHEME C4 |
| 88 | 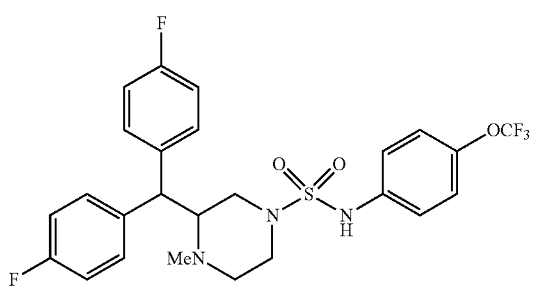 [SMILES: CN1CCN(S(=O)(=O)Nc2ccc(OC(F)(F)F)cc2)CC1C(c1ccc(F)cc1)c1ccc(F)cc1] | |
| 89 | 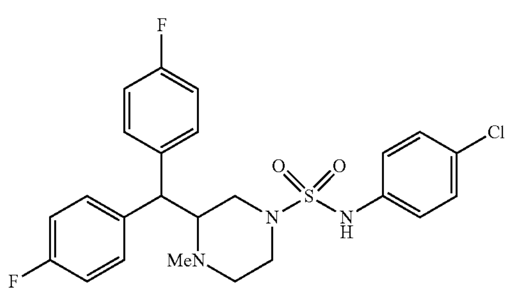 [SMILES: CN1CCN(S(=O)(=O)Nc2ccc(Cl)cc2)CC1C(c1ccc(F)cc1)c1ccc(F)cc1] | |

TABLE 1-continued

| Example No. | Structure | Synthesis scheme |
|---|---|---|
| 90 | *structure* | |
| 91 | *structure* | |
| 92 | *structure* | |
| 93 | *structure* | |

TABLE 1-continued
| Example No. | Structure | Synthesis scheme |
|---|---|---|
| 94 | 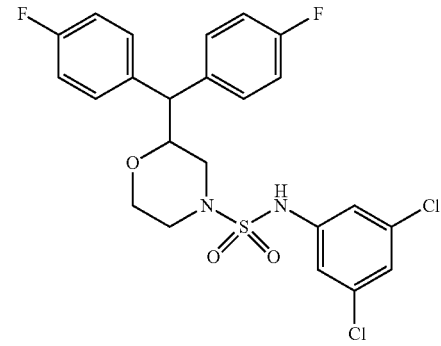 [SMILES: O=S(=O)(Nc1cc(Cl)cc(Cl)c1)N1CCOC(C(c2ccc(F)cc2)c2ccc(F)cc2)C1] | |
| 95 | 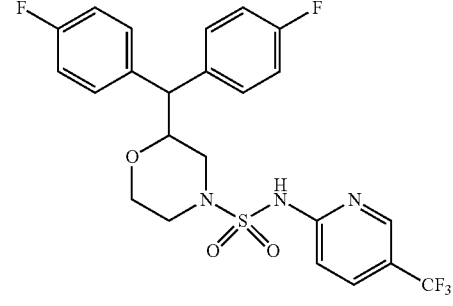 [SMILES: O=S(=O)(Nc1ccc(C(F)(F)F)cn1)N1CCOC(C(c2ccc(F)cc2)c2ccc(F)cc2)C1] | |
| 96 | 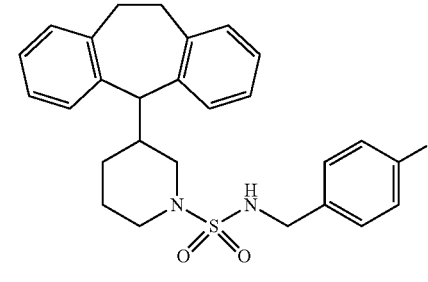 | |
| 97 | 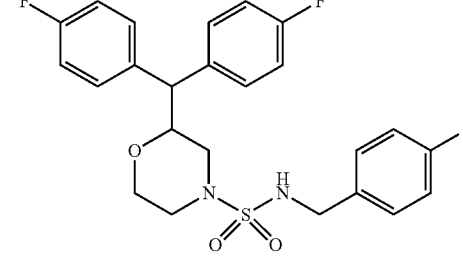 | |
| 98 | 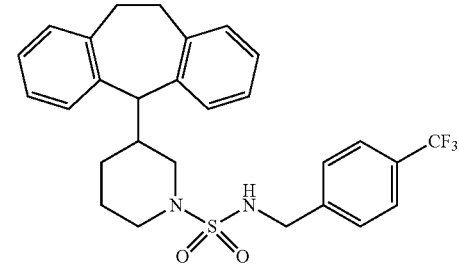 [SMILES: O=S(=O)(NCc1ccc(C(F)(F)F)cc1)N1CCCC(C2c3ccccc3CCc3ccccc32)C1] | |

TABLE 1-continued

| Example No. | Structure | Synthesis scheme |
|---|---|---|
| 99 | 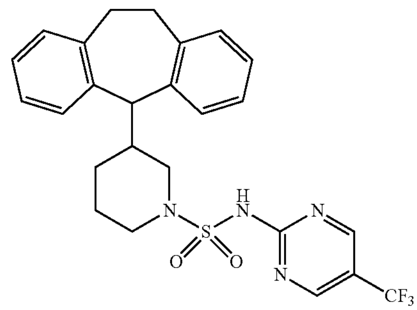 [SMILES: O=S(=O)(Nc1ncc(C(F)(F)F)cn1)N1CCCC(C2c3ccccc3CCc3ccccc32)C1] | |
| 100 | 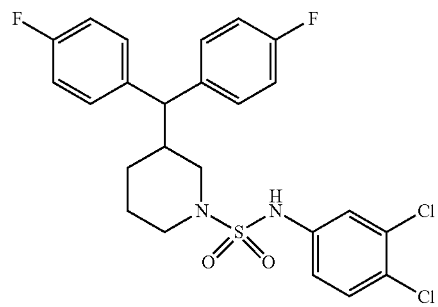 | |
| 101 | 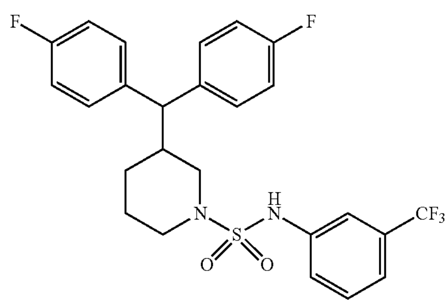 [SMILES: O=S(=O)(Nc1cccc(C(F)(F)F)c1)N1CCCC(C(c2ccc(F)cc2)c2ccc(F)cc2)C1] | |
| 102 | 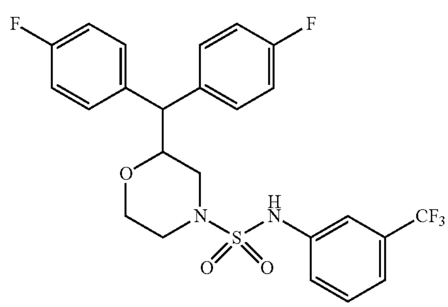 [SMILES: O=S(=O)(Nc1cccc(C(F)(F)F)c1)N1CCOC(C(c2ccc(F)cc2)c2ccc(F)cc2)C1] | |
| 103 | 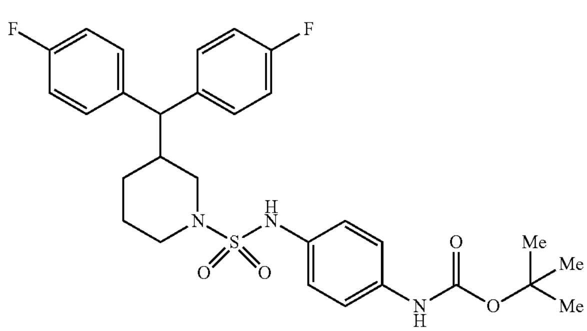 [SMILES: CC(C)(C)OC(=O)Nc1ccc(NS(=O)(=O)N2CCCC(C(c3ccc(F)cc3)c3ccc(F)cc3)C2)cc1] | |

TABLE 1-continued

Examples

| Example No. | Structure | Synthesis scheme |
|---|---|---|
| 104 | bis(4-fluorophenyl)methylidene-piperidine-N-sulfonamide-N'-(4-trifluoromethoxyphenyl) | |
| 105 | diphenylmethylidene-piperidine-N-sulfonamide-N'-(4-trifluoromethoxyphenyl) | |
| 106 | 10,11-dihydro-5H-dibenzo[a,d]cycloheptene-5-yl-piperidine-N-sulfonamide-N'-(2,2-difluoro-1,3-benzodioxol-5-yl) | |
| 107 | 10,11-dihydro-5H-dibenzo[a,d]cycloheptene-5-yl-piperidine-N-sulfonamide-N'-(2-trifluoromethoxyphenyl) | |
| 108 | bis(4-fluorophenyl)methylidene-piperidine-N-sulfonamide-N'-(4-chlorophenyl) | |

TABLE 1-continued

Examples

| Example No. | Structure | Synthesis scheme |
|---|---|---|
| 109 | bis(4-fluorophenyl)methylene-piperidine-N-sulfonyl-NH-(4-CF$_3$-phenyl) | |
| 110 | bis(4-fluorophenyl)methylene-piperidine-N-sulfonyl-NH-phenyl | |
| 111 | bis(4-fluorophenyl)methylene-piperidine-N-sulfonyl-NH-(3-CF$_3$-phenyl) | |
| 112 | bis(4-fluorophenyl)methylene-piperidine-N-sulfonyl-NH-(3-OCF$_3$-phenyl) | |
| 113 | dibenzosuberyl-piperidine-N-sulfonyl-NH-(3-OCF$_3$-phenyl) | |
| 114 | | |

TABLE 1-continued

Examples

| Example No. | Structure | Synthesis scheme |
|---|---|---|
| 115 | 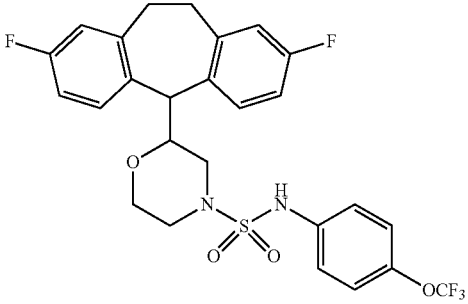 [SMILES: O=S(=O)(Nc1ccc(OC(F)(F)F)cc1)N1CCOC(C2c3ccc(F)cc3CCc3cc(F)ccc32)C1] | |
| 116 | 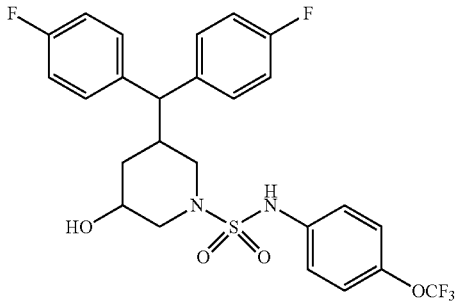 [SMILES: O=S(=O)(Nc1ccc(OC(F)(F)F)cc1)N1CC(O)CC(C(c2ccc(F)cc2)c2ccc(F)cc2)C1] | |
| 117 | 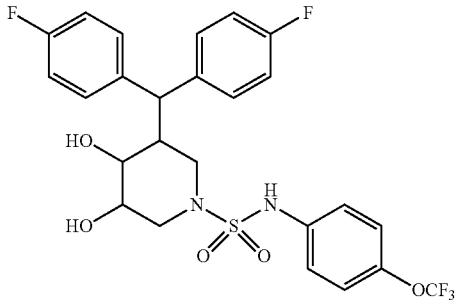 [SMILES: O=S(=O)(Nc1ccc(OC(F)(F)F)cc1)N1CC(O)C(O)C(C(c2ccc(F)cc2)c2ccc(F)cc2)C1] | |

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in Protecting Group Chemistry, 1$^{st}$ Ed., Oxford University Press, 2000; and in March's Advanced Organic chemistry: Reactions, Mechanisms, and Structure, 5$^{th}$ Ed., Wiley-Interscience Publication, 2001.

General Synthesis. Synthesis of compounds in the present invention generally proceed via derivatization of a 3-(diarylmethyl) cycloamine. This is shown generically in SCHEME A, wherein a 3-(diarylmethyl) cycloamine is reacted with an aryl sulfamoyl chloride, isocyanate, or the like reagent, to give the requisite sulfonyl urea or urea derivative, route A1. Alternatively the 3-(diarylmethyl) cycloamine maybe reacted with a reagent such as diphenyl cyanocarbonimidate to give an intermediate which is reacted in a second step with an aniline to give a cyano guanidine urea analog, similar methods may be used to prepare cyclobutendione or thiadiazoledioxide derivatives, route A2.

SCHEME A. General synthetic routes

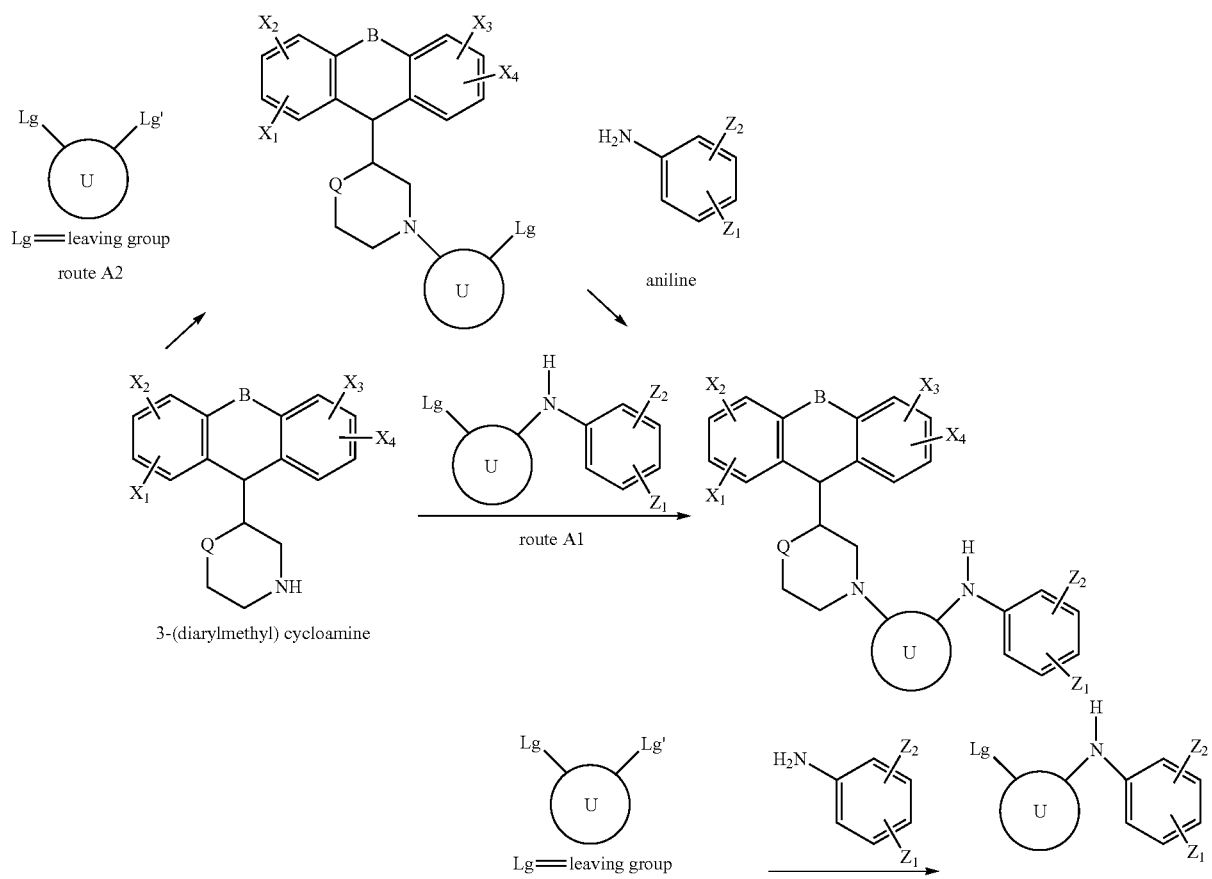

Several syntheses of 3-(diarylmethyl) cycloamines are known, see for example see Mizzoni et al, U.S. Pat. No. 3,503,983, Hitchcock et al, U.S. Pat. No. 82,858,306, Mueller et al, PCT Int Appl.: WO 00/02551, Ting et al, PCT publ. No.: WO 95/15949 and examples are shown in SCHEMES B. Variants of these routes, or other synthetic routes may also be employed as shown for example syntheses described below.

Scheme B2

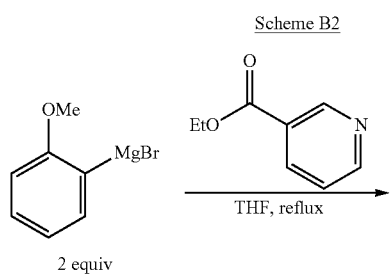

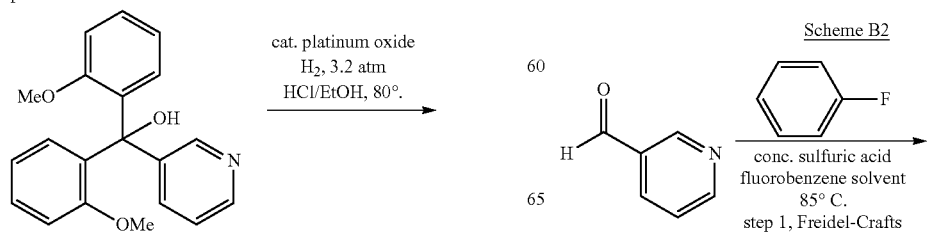

-continued

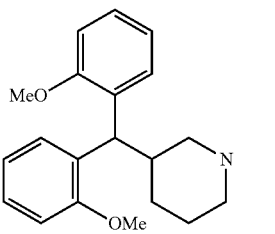

3-(bis(2-methoxyphenyl)methyl)piperidine
Known, see Mizzoni et al,
U.S. Pat. No. 3503983

Scheme B2

-continued

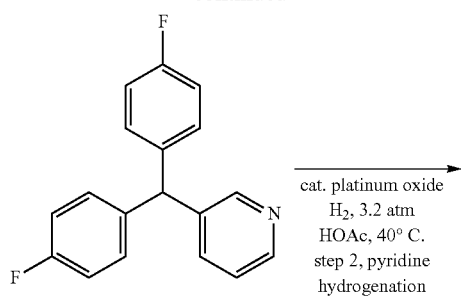

cat. platinum oxide
H₂, 3.2 atm
HOAc, 40° C.
step 2, pyridine
hydrogenation

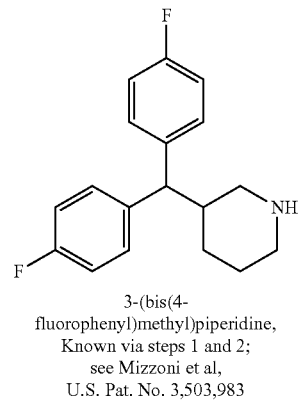

3-(bis(4-
fluorophenyl)methyl)piperidine,
Known via steps 1 and 2;
see Mizzoni et al,
U.S. Pat. No. 3,503,983

Scheme B3

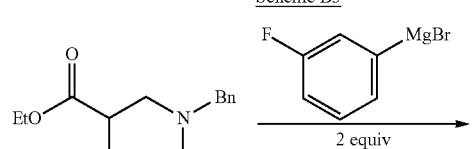

H₂, cat. palladium hydroxide

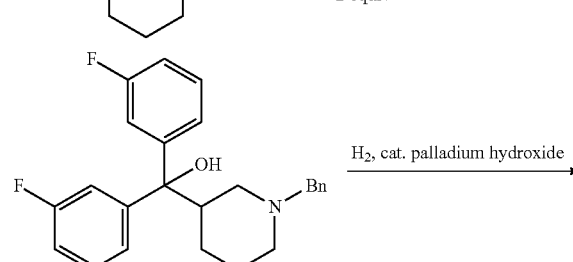

AcOH, HCl
reflux

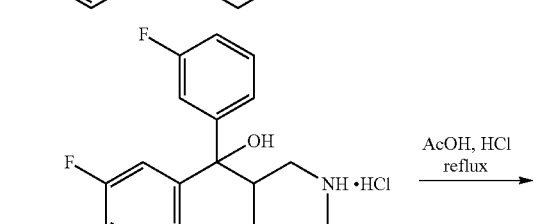

H₂, Pd/C

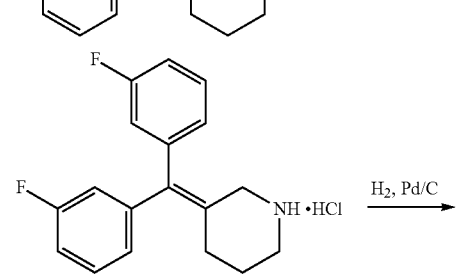

-continued

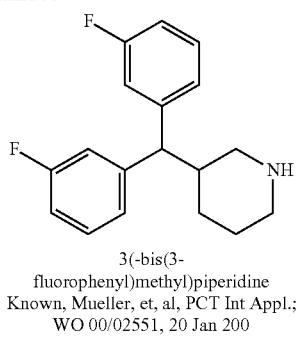

3(-bis(3-
fluorophenyl)methyl)piperidine
Known, Mueller, et, al, PCT Int Appl.;
WO 00/02551, 20 Jan 200

Scheme B4

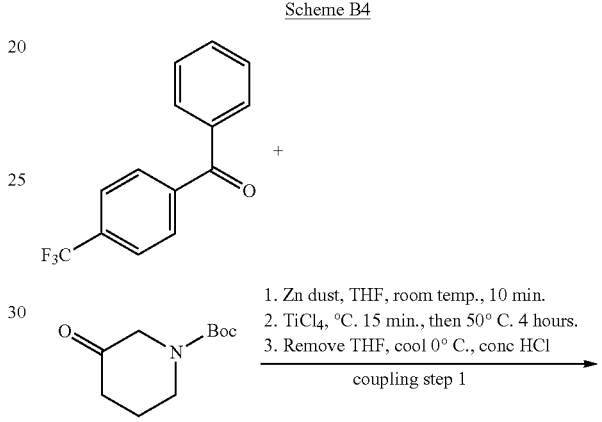

1. Zn dust, THF, room temp., 10 min.
2. TiCl₄, °C. 15 min., then 50° C. 4 hours.
3. Remove THF, cool 0° C., conc HCl coupling step 1

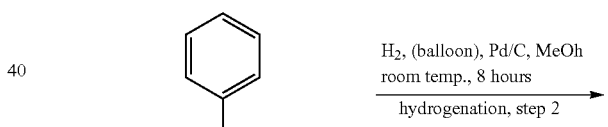

H₂, (balloon), Pd/C, MeOh
room temp., 8 hours hydrogenation, step 2

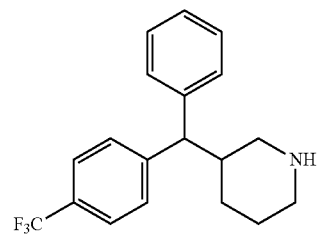

Known, 3-(phenyl(4-
(trifluoromethyl)phenyl)m)
ethyl)piperidine,
via steps 1 and 2; see
Hitccock et al,
US Patent No.
82858306, Sept 4 2012

Scheme B5

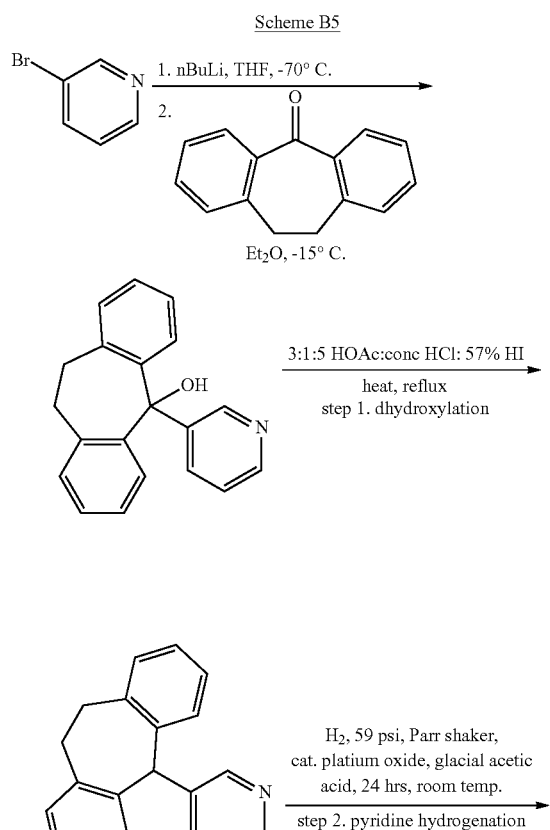

Known 3-(10,11-dihydro-5H-dibenzo[a,d][7]annulen-5-yl)piperidine
See Ting et al, PCT publ. No. WO 95/15949, 15 June 1995, via steps 1. and 2

SCHEMES B. Syntheses of 3-(diarylmethyl) cycloamines
Exemplary syntheses are presented below:

SCHEMES C: Synthesis of examples wherein the bridging group B is absent.

SCHEME C1 preparation of sulfonyl urea examples.

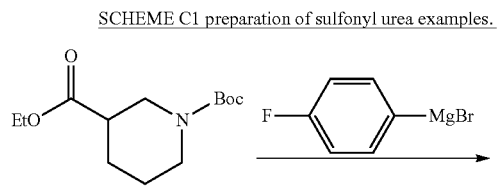

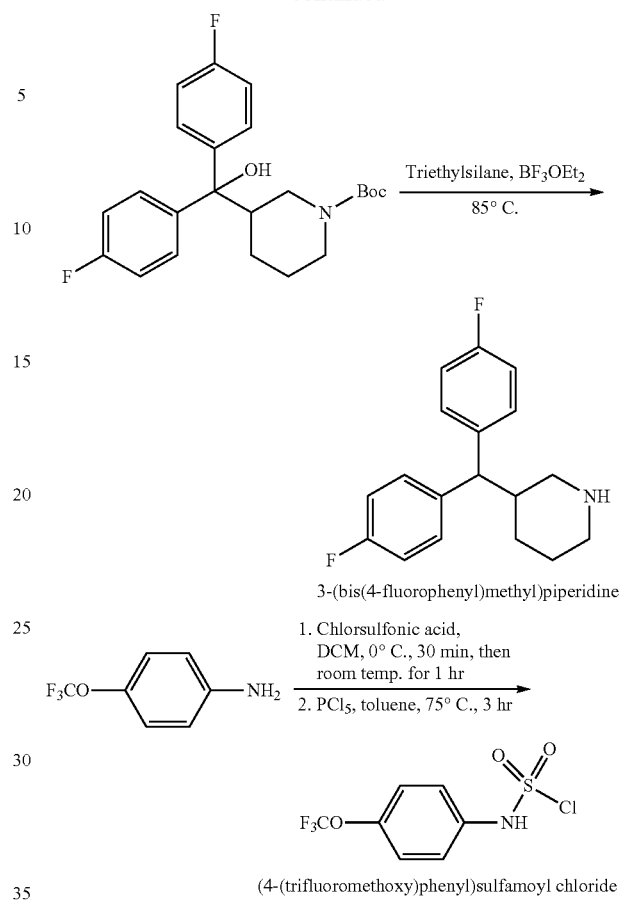

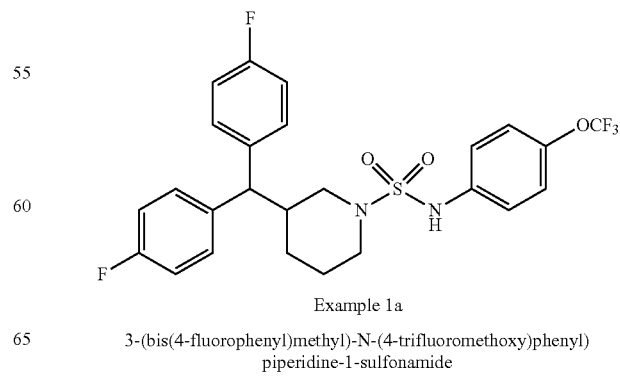

Example 1a
3-(bis(4-fluorophenyl)methyl)-N-(4-trifluoromethoxy)phenyl)
piperidine-1-sulfonamide

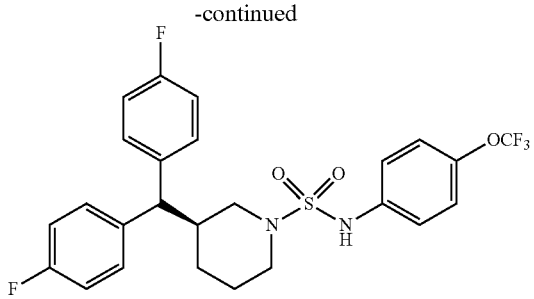

Example 1b (S)-3-(bis(4-fluorophenyl)methyl)-N-(4-trifluoromethoxy)phenyl)
piperidine-1-sulfonamide

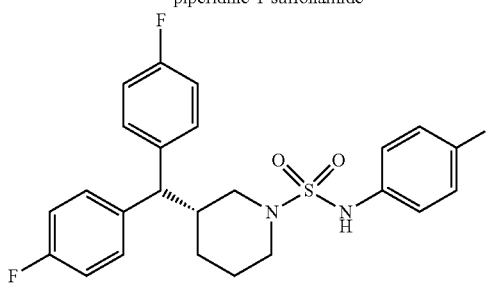

Example 1b (R)-3-(bis(4-fluorophenyl)methyl)-N-(4-trifluoromethoxy)phenyl)
piperidine-1-sulfonamide 3-(bis(4-fluorophenyl)methyl)piperidine is a known compound and may be prepared by the method shown in Scheme B2. The compound has also been prepared by a modification of the method shown in Scheme B3: briefly, one equivalent of N-Boc protected ethyl piperidine-3-carboxylate was added to a solution of 2.2 equivalents of the Grignard reagent formed from 4-fluoro-1-bromobenzene in THF with stirring at 0° C. The reaction was allowed to warm to room temperature and stirred overnight then quenched by adding aqueous ammonium chloride. The mixture was diluted with ethyl acetate, washed with brine and the oranic layer was dried over anhydrous sodium sulfate, then filtered and concentrated. The crude product was purified by flash chromatography to give Boc protected 3-(bis(4-fluorophenyl)(hydroxy)methyl)piperidine. Boc protected 3-(bis(4-fluorophenyl)(hydroxy)methyl)piperidine was dehydroxylated and Boc deprotected by treating with excess triethylsilane and boron trifluoride etherate in dioxane at 85° C. Reaction was cooled, diluted with methylene chloride and washed with sodium bicarbonate solution. The organic solution was dried over sodium sulfate, filtered and concentrated to give the crude product, 3-(bis(4-fluorophenyl)methyl)piperidine which was purified by flash chromatography. $^1$H NMR (400 MHz, CDCl$_3$) δ 9.640 (1H, br s), 9.410 (1H, br s), 7.280 (2H, m), 7.190 (2H, m), 6.694 (4H, m), 3.543 (1H, br d), 3.284 (1H, br d), 3.214 (1H, br d), 2.842 (1H, br q), 2.702 (1H, br q), 2.430 (1H, q), 1.950-1.800 (2H, overlapping m), 1.718 (1H, br d), 1.080 (1H br q); ESI-LCMS m z 288.15 [M+H$^+$].

Preparation of sulfamoyl chloride used in the synthesis of Example 1 proceeds by reacting 3-(bis(4-fluorophenyl)methyl)piperidine with (4-(trifluoromethoxy)phenyl)sulfamoyl chloride. The sulfamoyl chloride was prepared as follows: to a solution of 4-(trifluoromethoxy)aniline (2.00 g, 11.3 mmol) in dry dichloromethane (12 mL), placed in ice bath under argon, was added a solution of chlorosulfonic acid (0.438 g, 3.76 mmol) in dichloromethane (2.0 mL). The reaction mixture was stirred at 0° C. for 30 min, and at RT for 1 h. Precipitate was collected by filtration and dried under high vacuum. The material was suspended in toluene (6.0 mL) and PCl$_5$ (0.782 g, 3.76 mmol) was added. The mixture was stirred at 75° C. for 3 h, cooled to RT, and filtered. Solid residue was washed with toluene and filtrate was collected. The filtrate was evaporated and dried under high vacuum. The crude (4-(trifluoromethoxy)phenyl)sulfamoyl chloride (1.01 g) was used for the next step without further purification.

Synthesis of Example 1a. To a solution of (4-(trifluoromethoxy)phenyl)sulfonylchloride (550 mg, 2 mmol) in DCM (10 mL) was added 3-(bis(4-fluorophenyl)methyl)piperidine (460 mg, 1.6 mmol). The resulting mixture was stirred at room temperature for 1 hour. The mixture was concentrated under vacuum and purified by chromatography using Biotage (C18 column, eluting with 10% to 95% MeCN in H$_2$O, containing 0.1% TFA) to afford Example 1a (265 mg, 31% yield) as a white solid. HPLC purity: 98.9% @ 214 nm, 100.0% @ 254 nm. LCMS (Shimadzu XR): R$_t$=2.504 min; m/z calculated for [M−H]$^-$525.13, found 525.10. $^1$H NMR, 400 MHz in DMSO-d$_6$: δ 10.03 (1H, s), 7.37-7.03 (12H, aromatic m), 3.66 (1H, d J=11.6 Hz), 3.49 (1H, br d J=11.6 Hz), 3.27 (1H, br d J=12.4 Hz), 2.68 (1H, br t J=11.6), 2.39 (1H, br t J=11 Hz), 2.26 (1H, m), 1.61 (1H, br d), 1.37 (2H, overlapping m), 0.89 (1H, m).

Other solvents such as dry acetonitrile, THF or DMF may also be used for the reaction. Amine bases such as triethylamine, ethyldiisopropylamine or pyridine may also be added in the reaction to form the sulfonyl urea.

Example 1a may be resolved into it's enantiomers, by preparative chiral HPLC to give (S)-3-(bis(4-fluorophenyl)methyl)-N-(4-(trifluoromethoxy)phenyl)piperidine-1-sulfonamide, Example 1b and (R)-3-(bis(4-fluorophenyl)methyl)-N-(4-(trifluoromethoxy)phenyl)piperidine-1-sulfonamide, Example 1c. Alternatively the intermediate, 3-(bis(4-fluorophenyl)methyl)piperidine, may be resolved by chiral HPLC or crystallization with a chiral acid to give optically enriched (S)- or (R)-3-(bis(4-fluorophenyl)methyl)piperidine and this material may be carried through the steps above to give final products in optically pure form. Optically enriched 3-(bis(4-fluorophenyl)methyl)piperidine may also be prepared by starting from optically pure N-Boc protected ethyl piperidine-3-carboxylate. Examples 2-12 may be prepared the route shown in SCHEME C1 where the aniline used to prepare the sulfamoyl chloride is appropriately selected: in Example 7, 3-chloroaniline is used used as the starting material and so forth.

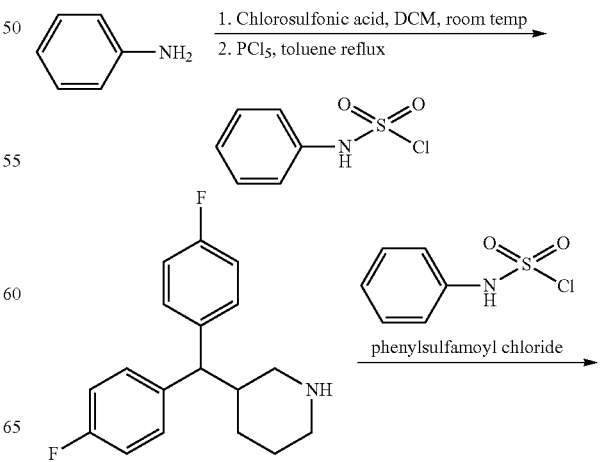

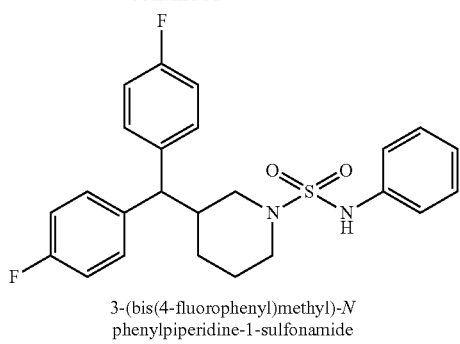

3-(bis(4-fluorophenyl)methyl)-*N*-phenylpiperidine-1-sulfonamide

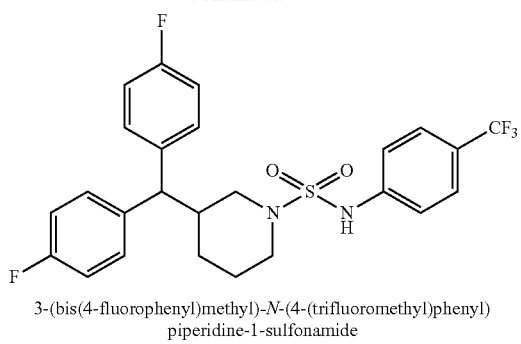

3-(bis(4-fluorophenyl)methyl)-*N*-(4-(trifluoromethyl)phenyl)piperidine-1-sulfonamide Synthesis of Example 2. To a solution of aniline (930 mg, 10.0 mmol) in DCM (20 mL) was added chlorosulfonic acid (1.42 g, 12.2 mmol). The mixture was stirred at RT for 1 hour and concentrated under vacuum before diluting with dry toluene (10 mL). To the above solution was added PCl$_5$ (2.12 g, 10.2 mmol). The mixture was heated at 110° C. for overnight. After removing the solvent under vacuum, the crude phenylsulfamoyl chloride was used directly in next step without further purification. To a solution of phenylsulfamoyl chloride (381 mg, 2 mmol) in DCM (10 mL) was added 3-(bis(4-fluorophenyl)methyl)piperidine (460 mg, 1.6 mmol). The resulting mixture was stirred at room temperature for 1 hour. The mixture was concentrated under vacuum and purified by Biotage (C18 column, eluting with 10% to 95% MeCN in H$_2$O, containing 0.1% TFA) to afford Example 2, 3-(bis(4-fluorophenyl)methyl)-N-phenylpiperidine-1-sulfonamid (218 mg, 27.5% yield) as a white solid. HPLC purity: 97.3% @ 214 nm, 100.0% @ 254 nm. ESI-MS m/z [MH]$^+$ found, 443.10. $^1$H NMR, 400 MHz in DMSO-d$_6$: δ 9.78 (1H, s), 7.34-7.26 (6H, aromatic m), 7.13-7.04 (7H, aromatic m), 3.66 (1H, d J=11.2 Hz), 3.48 (1H, br d J=12.0 Hz), 3.29 (1H, br d J=12.0 Hz), 2.65 (1H, br t J=12.0), 2.37 (1H, br t J=12.0), 2.26 (1H, br t J=11 Hz), 1.59 (1H, m), 1.34 (2H, overlapping m), 0.87 (1H, m).

Synthesis of Example 4. To a solution of 4-trifluoromethylaniline (1.61 g, 10.0 mmol) in DCM (20 mL) was added chlorosulfonic acid (1.42 g, 12.2 mmol). The mixture was stirred at RT for 1 hour and concentrated under vacuum before diluting with dry toluene (10 mL). To the above solution was added PCl$_5$ (2.12 g, 10.2 mmol). The mixture was heated at 110° C. for overnight. After removing the solvent under vacuum, the crude (4-(trifluoromethyl)phenyl)sulfamoyl chloride was used directly in next step without further purification. To a solution of (4-(trifluoromethyl)phenyl)sulfamoyl chloride (520 mg, 2 mmol) in DCM (10 mL) was added 3-(bis(4-fluorophenyl)methyl)piperidine (460 mg, 1.6 mmol). The resulting mixture was stirred at room temperature for 1 hour. The mixture was concentrated under vacuum and purified by Biotage (C18 column, eluting with 10% to 95% MeCN in H$_2$O, containing 0.1% TFA) to afford Example 4, 3-(bis(4-fluorophenyl)methyl)-N-(4-(trifluoromethyl)phenyl)piperidine-1-sulfonamide, (220 mg, 24% yield) as a white solid. HPLC purity: 98.5% @ 214 nm, 98.2% @ 254 nm. LCMS (Shimadzu 2200): R$_f$=3.674 min; m/z calculated for [M+H]$^+$ 511.14, found 511.20. $^1$H NMR, 400 MHz in DMSO-d$_6$: S 10.33 (1H, s), 7.69 (2H, d J=8.8 Hz), 7.32-7.25 (6H, aromatic m), 7.13-7.03 (4H aromatic m), 3.68 (1H, d J=11.2 Hz), 3.52 (1H, br d J=11.2 Hz), 3.29 (1H, br d J=12.0 Hz), 2.70 (1H, br t J=8.8 Hz), 2.41 (1H, br t J=10.0), 2.28 (1H, m), 1.62 (1H, m), 1.36 (2H, overlapping m), 0.92 (1H, m).

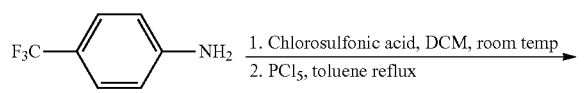

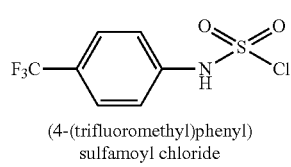

(4-(trifluoromethyl)phenyl)sulfamoyl chloride

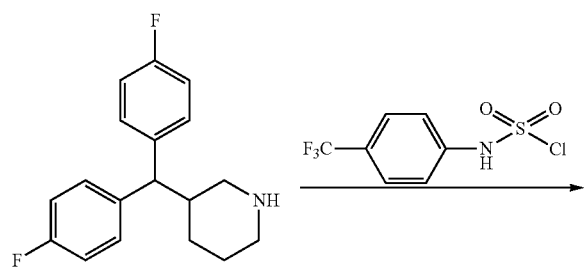

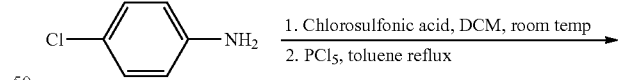

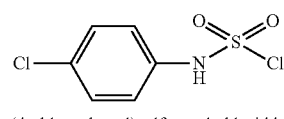

(4-chlorophenyl)sulfamoyl chloridde

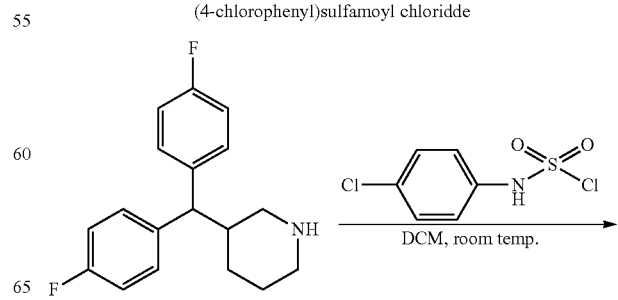

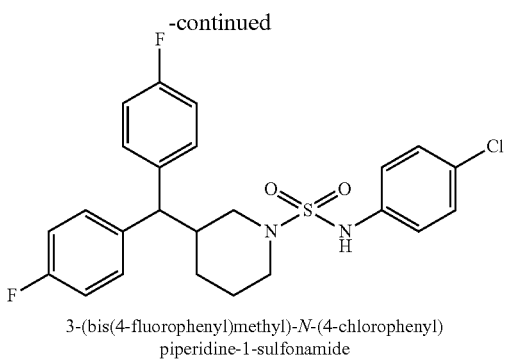

3-(bis(4-fluorophenyl)methyl)-*N*-(4-chlorophenyl)
piperidine-1-sulfonamide

Synthesis of Example 6. To a solution of 4-chloroaniline (1.27 g, 10.0 mmol) in DCM (20 mL) was added chlorosulfonic acid (1.42 g, 12.2 mmol). The mixture was stirred at RT for 1 hour and concentrated under vacuum before diluting with dry toluene (10 mL). To the above solution was added PCl$_5$ (2.12 g, 10.2 mmol). The mixture was heated at 110° C. for overnight. After removing the solvent under vacuum, the crude (4-chlorophenyl)sulfamoyl chloride was used directly in next step without further purification. To a solution of (4-chlorophenyl)sulfamoyl chloride (450 mg, 2 mmol) in DCM (10 mL) was added 3-(bis(4-fluorophenyl)methyl)piperidine (460 mg, 1.6 mmol). The resulting mixture was stirred at room temperature for 1 hour. The mixture was concentrated under vacuum and purified by chromatography using Biotage (C18 column, eluting with 10% to 95% MeCN in H$_2$O, containing 0.1% TFA) to afford 3-(bis(4-fluorophenyl)methyl)-N-(4-chlorophenyl)piperidine-1-sulfonamide (228 mg, 26.5% yield) as a white solid. HPLC purity: 100% @214 nm, 100% @ 254 nm. LCMS (Shimadzu XR): R$_t$=2.449 min; m/z calculated for [M+H]$^+$ 477.11, found 477.10. $^1$H NMR, 400 MHz in DMSO-d$_6$: δ 9.96 (1H, s), 7.39 (2H, d J=8.8 Hz), 7.33-7.28 (4H, aromatic m), 7.14-7.04 (6H aromatic m), 3.67 (1H, d J=11.6 Hz), 3.48 (1H, br d J=12.0 Hz), 3.28 (1H, br d J=10.4 Hz), 2.64 (1H, br t J=10.8 Hz), 2.37 (1H, br t J=10.0), 2.27 (1H, m), 1.60 (1H, m), 1.39-1.24 (2H, overlapping m), 0.91 (1H, m).

Example 13, a urea, is prepared by treating 3-(bis(4-fluorophenyl)methyl)piperidine with 4-trifluoromethoxyphenyl isocyanate in a solvent such as THF, toluene or acetonitrile, as shown in SCHEME C2. Analogous urea examples may be prepared using other substituted phenyl isocyanates.

SCHEME C2

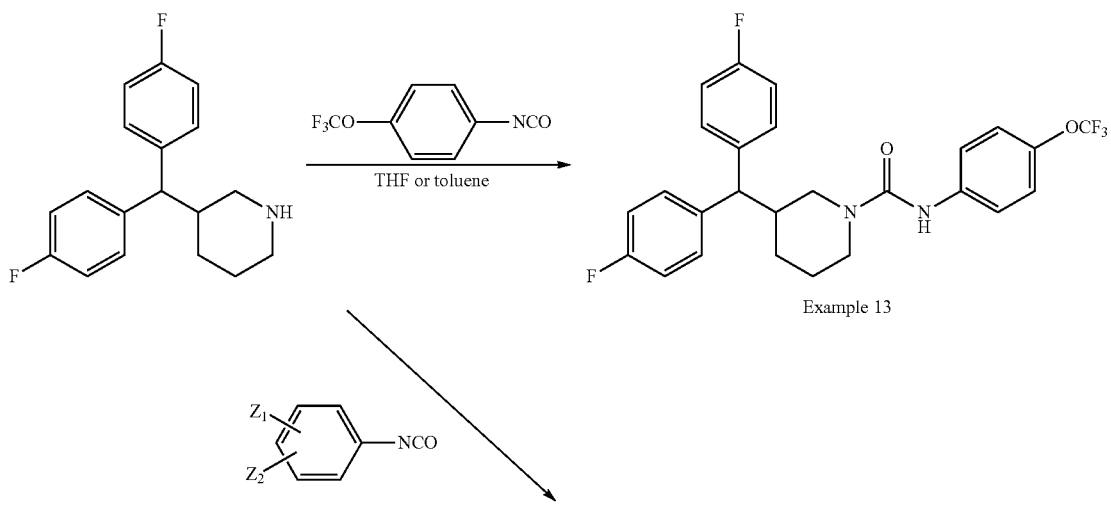

Example 13

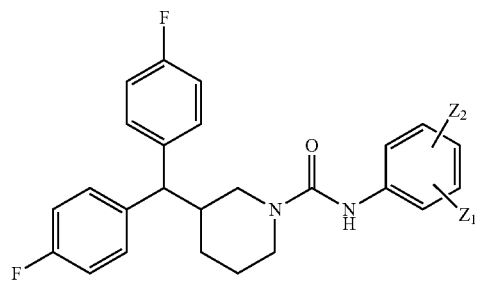

Other urea isosteres may be accessed from 3-(bis(4-fluorophenyl)methyl)piperidine as shown in SCHEMES C3, C4. Thus SCHEME C3 shows the synthesis of the cyano-amidine urea isostere: 3-(bis(4-fluorophenyl)methyl)piperidine is reacted with diphenyl cyanocarbonimidate in an alcohol solvent such as methanol or ispropanol to give phenyl 3-(bis(4-fluorophenyl)methyl)-N-cyanopiperidine-1-carbimidate, which is reacted with 4-trifluoromethoxy aniline in a second step to give the product cyanoamidine, Example 14 via route 2. Alternatively, 4-trifluoromethoxy aniline may be activated to give phenyl-N'-cyano-N-(4-(trifluoromethoxy)phenyl)carbamimidate, which is reacted in a second step with 3-(bis(4-fluorophenyl)methyl)piperidine to give Example 14 via route 1; these sequences are shown in SCHEME C3. Nitroguanidine, Example 15 are synthesized by an analogus route to that shown in SCHEME C3, starting from 1-nitro-2,3-diphenylisourea in place of diphenyl cyanocarbonimidate. Similarly the nitroethene isostere, Example 16, may be synthesized by the same shown in Scheme C3 using (2-nitroethene-1,1-diyl)bis(methylsulfane) in place of diphenyl cyanocarbonimidate.

SCHEME C3

Route 2

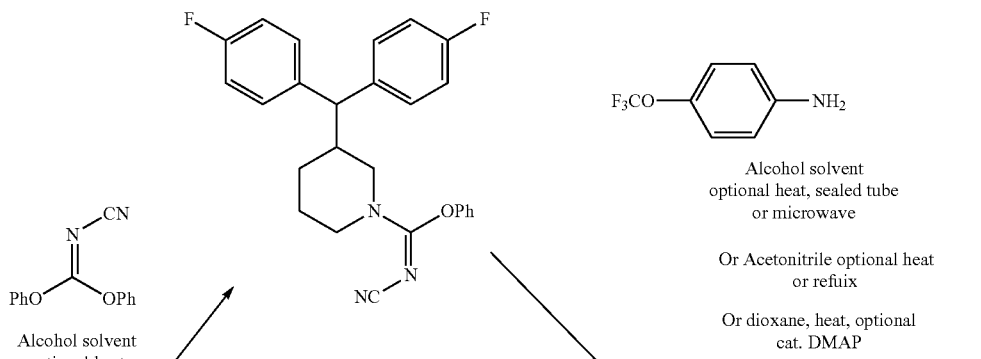

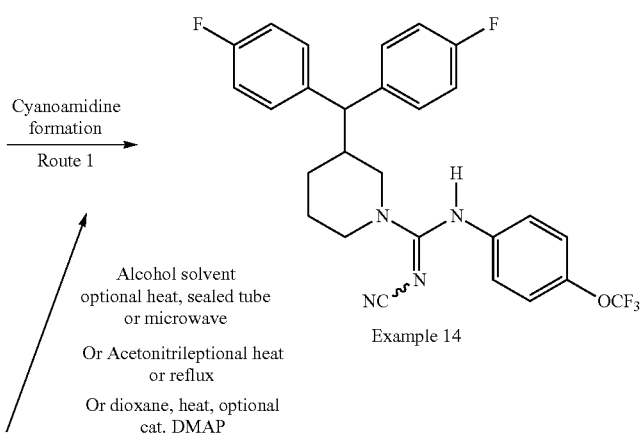

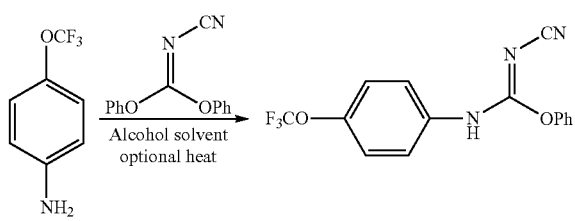

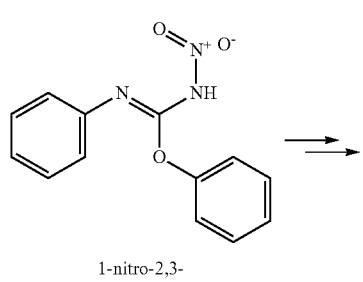

1-nitro-2,3-diphenylisourea

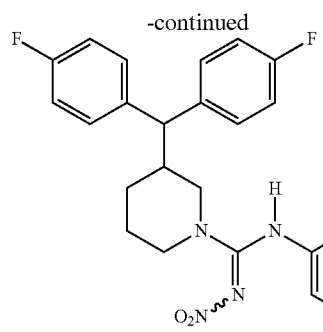

Example 15

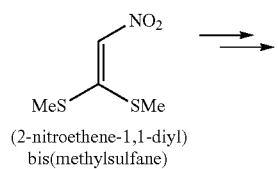

(2-nitroethene-1,1-diyl)bis(methylsulfane)

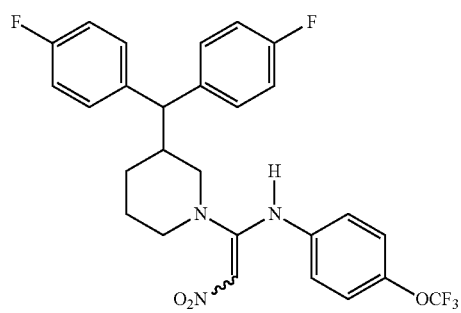

Example 16

Analogous routes to the cyclobutenedione and thiadiazole dioxide analogs are shown in SCHEME C4, which show syntheses of Examples 17 and 18. Stepwise nucleophilic displacements by amines on 3,4-dimethoxycyclobut-3-ene-1,2-dione are described in Merritt et al, Bioorganic & Medicinal Chemistry Letters 16 (2006) 4107-4110 and these conditions may be adapted for synthesis of compounds of the present invention. 4-trifluoromethoxy aniline is stirred with an excess of 3,4-dimethoxycyclobut-3-ene-1,2-dione in methanol. The reaction is concentrated in vacuo and maybe be purified by flash chromatography if required. The intermediate 3-methoxy-4-((4-(trifluoromethoxy)phenyl)amino)cyclobut-3-ene-1,2-dione is treated with 3-(bis(4-fluorophenyl)methyl)piperidine in a solvent such as methanol and an amine base such as diisopropylamine with heating as required. Other solvents such as ethanol, isopropanol or butanol may be used with conventional heating or microwave to effect the reaction. The order of the reactions may be reversed, ie condensation with 3-(bis(4-fluorophenyl)methyl)piperidine is performed first, followed by reaction with 4-trifluoromethoxy aniline, as shown in SCHEME C4. The thiadiazoledioxides are prepared in an analogous way from 3,4-diethoxy-1,2,5-thiadiazole 1,1-dioxide, where representative conditions for amine displacements are described in Biju et al, Bioorg. Med. Chem. Lett. 18 (2008) 228-231.

Scheme C4

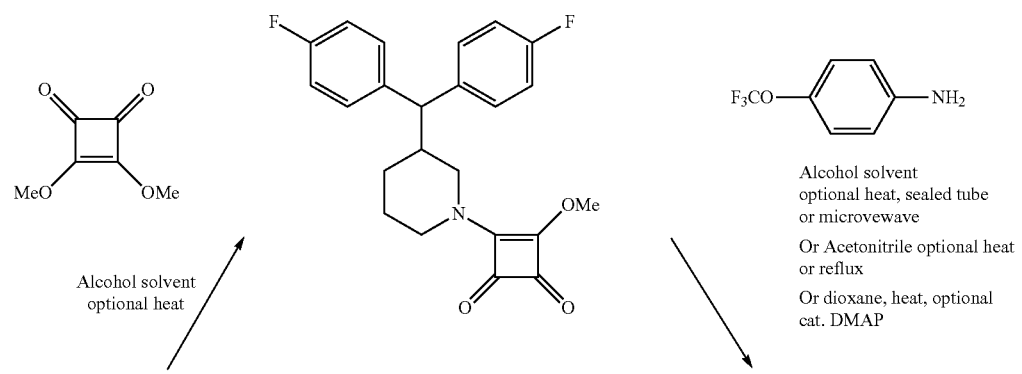

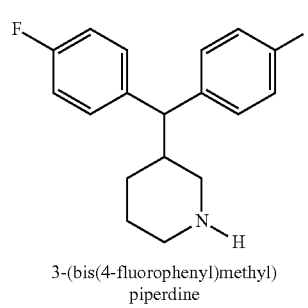

3-(bis(4-fluorophenyl)methyl)piperdine

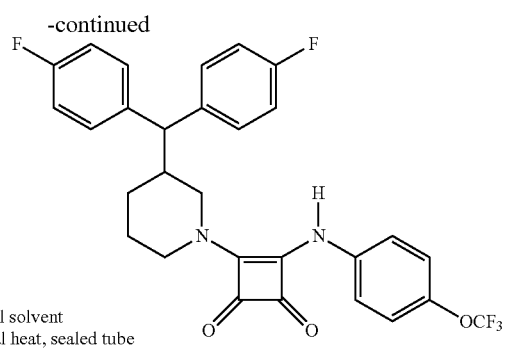

Example 17

Cyclobutendione formation

Alcohol solvent optional heat, sealed tube or microwave
Or Acetonitrile optional heat or reflux
Or dioxane, heat, optional cat. DMAP

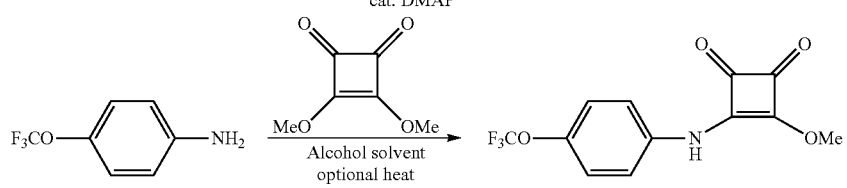

Alcohol solvent optional heat

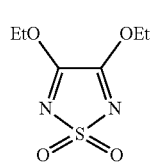

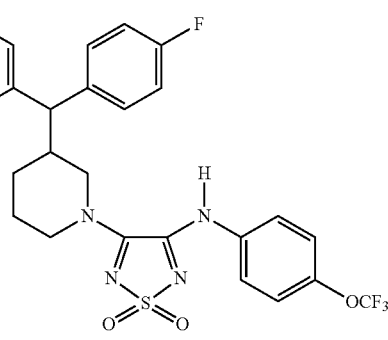

Example 18

Steps as above

SCHEME C5

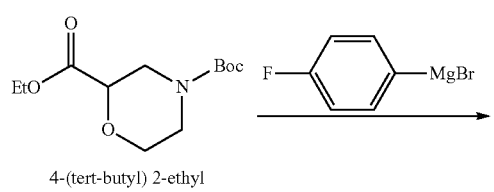

4-(tert-butyl) 2-ethyl morpholine-2,4-dicarboxylate

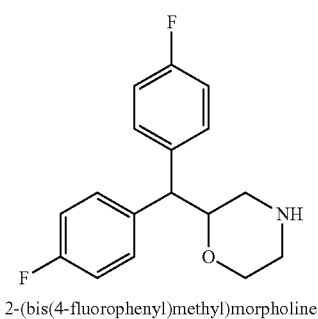

2-(bis(4-fluorophenyl)methyl)morpholine

1. Chlorsulfonic acid, DCM, 0° C., 30 min, then room temp. for 1 hr
2. PCl$_5$, toluene, 75° C., 3 hr

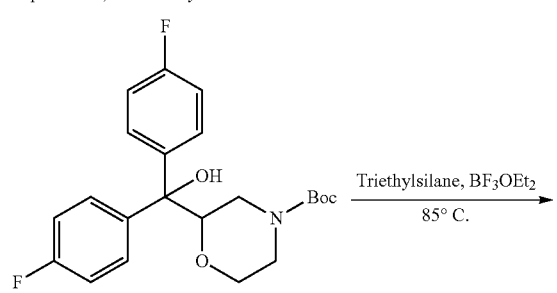

Triethylsilane, BF$_3$OEt$_2$
85° C.

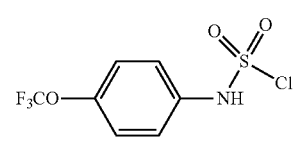

(4-(trifluoromethoxy)phenyl)sulfamoyl chloride

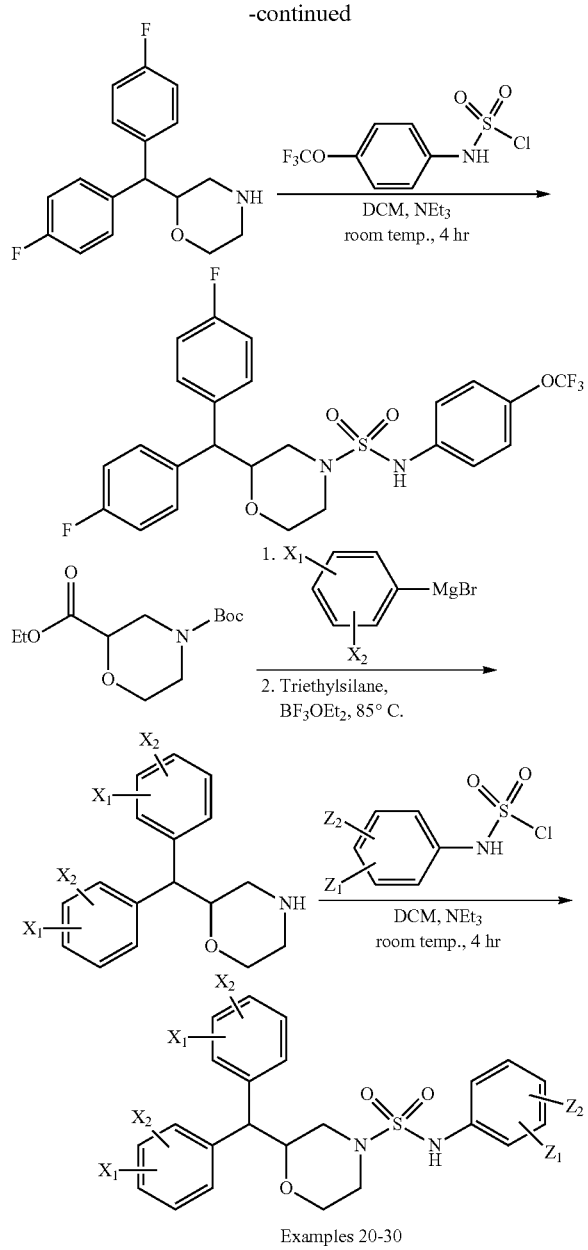

Examples 20-30

Examples where the cycloamine is heterocyclic, for example morpholino with Q=O, may be synthesized as shown in SCHEME C5. Reaction conditions and procedures are similar to those shown in SCHEME C1: N-Boc protected ethyl morpholine-2-carboxylate is reacted with excess 4-fluorophenyl magnesium bromide to give the Boc-protected tertiary alcohol. This is dehydroxylated and deprotected with triethylsilane—borontrifluoride etherate to give 2-(bis(4-fluorophenyl)methyl)morpholine. 2-(bis(4-fluorophenyl)methyl)morpholine is reacted with (4-(trifluoromethoxy)phenyl)sulfamoyl chloride to give Example 19. This sequence may be used to synthesize Examples 20-30 by using other substituted phenyl sulfamoyl chlorides, starting from the appropriate aniline. The sequence may be further adapted by employing other readily available substituted phenyl Grignard (or substituted phenyl lithium) reagents, as shown in SCHEME C5. As before, Example 19 may be resolved into it's enantiomers by preparative chiral HPLC.

2-(bis(4-fluorophenyl)methyl)morpholine may also be resolved, or synthesized from optically enriched strating materials, and used in condensation with appropriately substituted phenyl sulfamoyl chlorides.

Example 31, a urea, maybe prepared from 2-(bis(4-fluorophenyl)methyl)morpholine by treating it with 4-trifluoromethoxyphenyl isocyanate by the methods described for SCHEME C2. Related urea analogs maybe prepared by using other readily available substituted phenyl isocyanates.

Urea isosteres, Examples 32, 33 and 34 may be prepared from 2-(bis(4-fluorophenyl)methyl)morpholine by the methods describe for SCHEME C3. Similarly cyclobutendione and thiadiazoledioxide analogs, Examples 35 and 36 respectively, may be prepared from 2-(bis(4-fluorophenyl)methyl) morpholine by the methods described for SCHEME C4. The methods described in SCHEME C5 may be used to synthesize thiomorpholine examples using N-Boc protected ethyl thiomorpholine-2-carboxylate as a starting material, see example 61.

The methods described in SCHEME C1 may be adapted to synthesize examples in which the central ring is a pyrrolidine, $Q=(CH_2)_n$ with n=0, or azepane (homopiperidine), $Q=(CH_2)_n$ with n=2. These are shown in SCHEME C6 for the syntheses of Examples 55 and 56. Ureas, urea isosteres, cyclobetendione and thiadiazole dioxide analogs of the pyrrolidines and azepanes may be prepared in the same way as described above for the piperidines in SCHEMES C2, C3 and C4. Examples 55 and 56, shown in SCHEME C6 may be separated in their enantiomers by preparative chiral HPLC or prepared from optically pure starting materials.

In the above example syntheses the aryl groups of the diaryl cycloamines are the same, however methods are reported for the synthesis wherein the two aryl groups are differently substituted. An instance is shown in SCHEME B4 as reported in Hitchcock et al, U.S. Pat. No. 82,858,306 and this material may be used to make Example 63 by the methods of SCHEME C1. Other unsymmetrically substituted benzephones may be used in the method reported by Hitchcock with 3-oxo-N-Boc piperidine or other 3-oxo protected cycloamines, for example 3-oxo-N-Boc pyrrolidine. A second route to examples in which the aryl groups are differently substituted is shown in SCHEME C7: here the Weinreb amide is formed from an N-Boc protected cycloic amino acid, for example morpholine-2-carboxylic acid, using standard coupling conditions. The Weinreb amide is treated with 1.1 equivalents of a substituted phenyl Grignard reagent, for example 4-fluorophenyl magnesium bromide, in THF at −78° C. and warmed to 0° C. The reaction is quenched with aqueous ammonium chloride and worked up under standard conditions to yield a ketone, N-Boc-2-(4-fluorobenzoyl)morpholine in the example given in SCHEME C7. This ketone is treated in a second step with an aryl lithium, for example phenyllithium to give a tertiary alcohol, which is worked-up, isolated and purified by standard procedures. The tertiary alcohol is then converted to the final product, Example 64 by the steps described in SCHEME C1, and also shown in SCHEME C7.

SCHEME C6

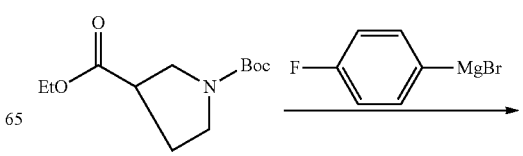

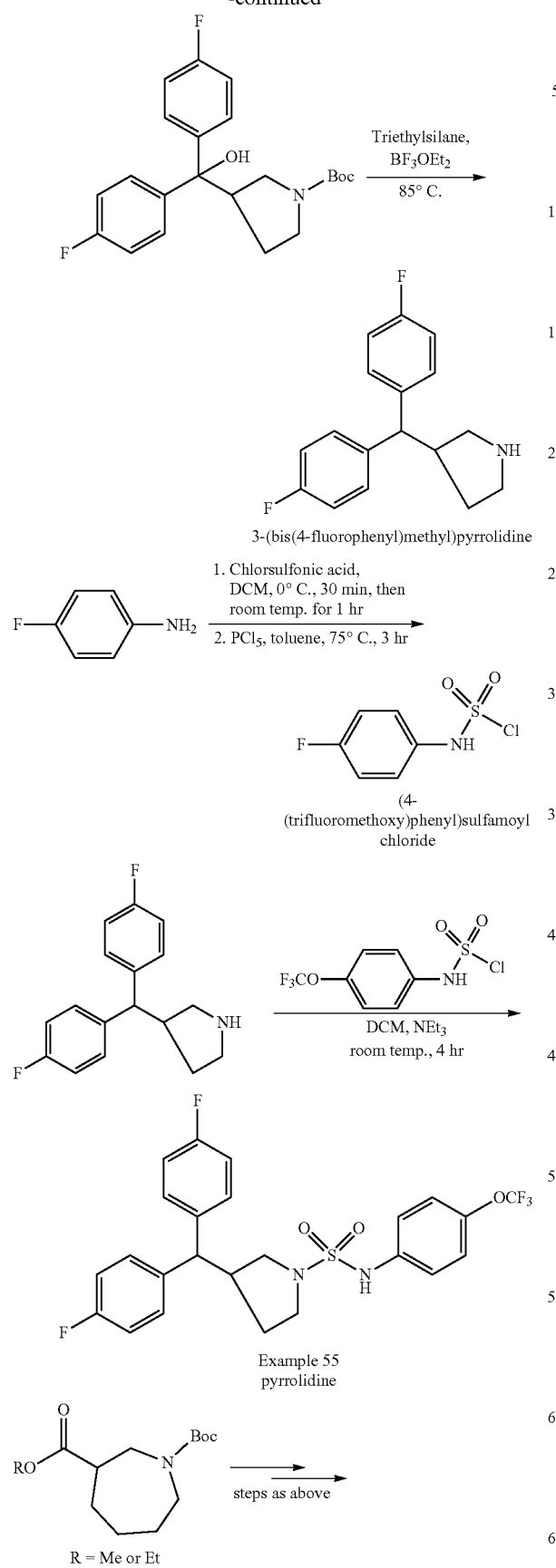
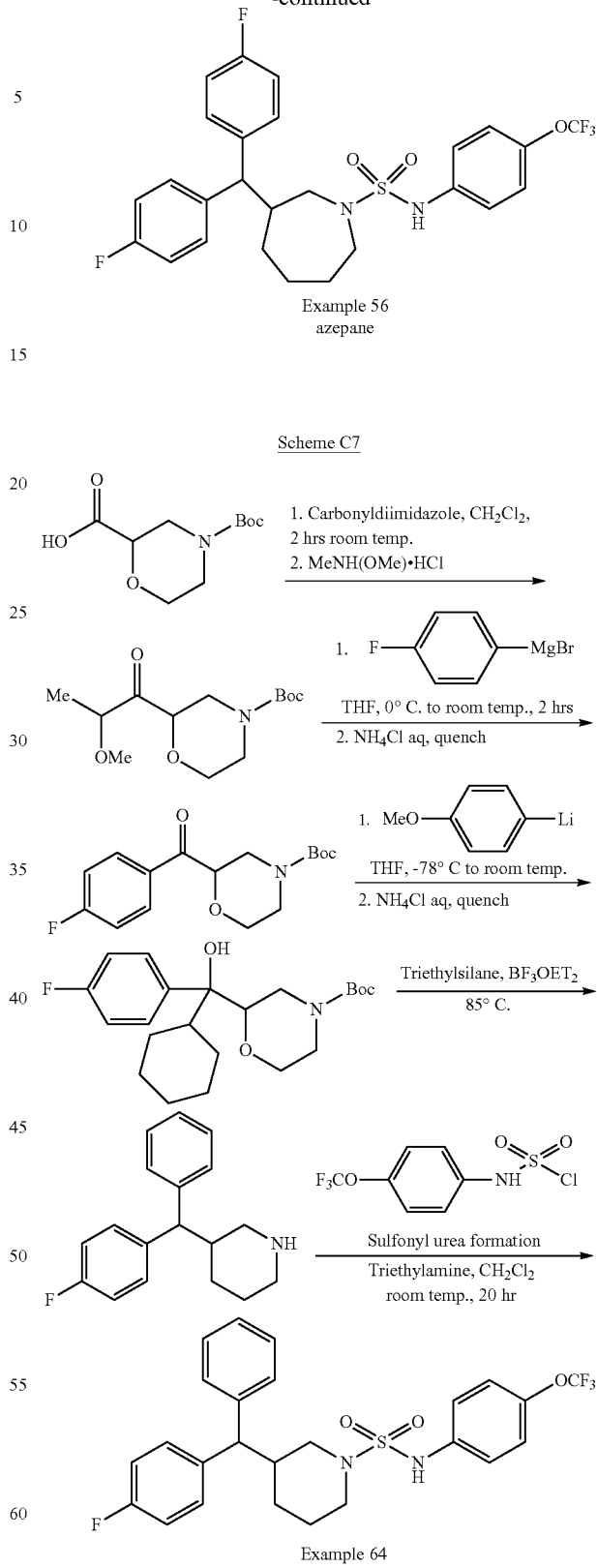
SCHEMEs D: Synthesis of examples wherein the bridging group B is —CH$_2$CH$_2$— or a direct bond. 3-(10,11-dihydro-5H-dibenzo[a,d][7]annulen-5-yl)piperidine is a known compounds and it was prepared by the method of Ting et al as shown in SCHEME B5. A variant of this route in which the intermediate tertiary alcohol was reduced with triethylsilane-boron trifluoride etherate prior to reduction of the pyridine was also successfully used. 3-(10,11-dihydro-5H-dibenzo[a,d][7]annulen-5-yl)piperidine has $^1$H NMR (400 MHz, CDCl$_3$) δ 9.520 (1H, br s), 9.237 (1H, br s), 7.160-6.977 (8H overlapping m), 3.650-3.393 (3H, overlapping in), 3.181 (1H, br d), 3.000-2.850 (4H, overlapping in), 2.610 (1H, in), 2.427 (1H, br q), 1.800-1.675 (3H, overlapping in), 1.100 (1H, in), 1.080; ESI-LCMS m z 278.20 [M+H$^+$]. Formation of the sulfonyl urea proceeds using the same conditions and reagents as described in SCHEME C1: reaction of 3-(10,11-dihydro-5H-dibenzo[a,d][7]annulen-5-yl)piperidine with (4-(trifluoromethoxy)phenyl)sulfamoyl chloride gives Example 37. Examples 38-48 are synthesized in the same way using sulfamoyl chlorides prepared from the appropriately substituted anilines.

Ureas, urea isosteres, cyclobutendione and thiadiazolediooxide Examples 49-54 are prepared from 3-(10,11-dihydro-5H-dibenzo[a,d][7]annulen-5-yl)piperidine using the reactions described in SCHEME C2, C3 and C4.

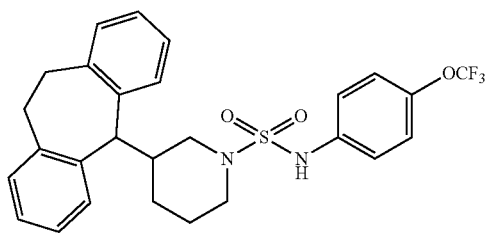

Example 37

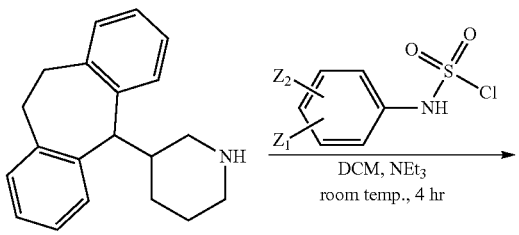

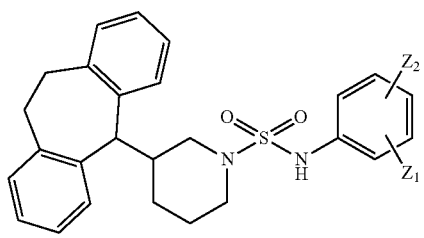

Example 38-48

Scheme D1

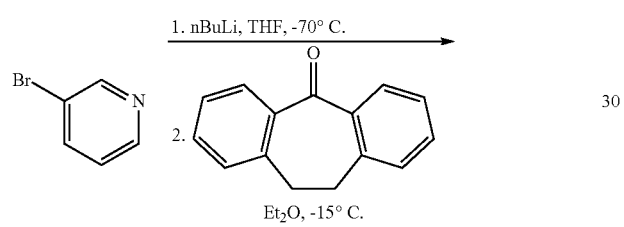

tertiary alcohol intermediate

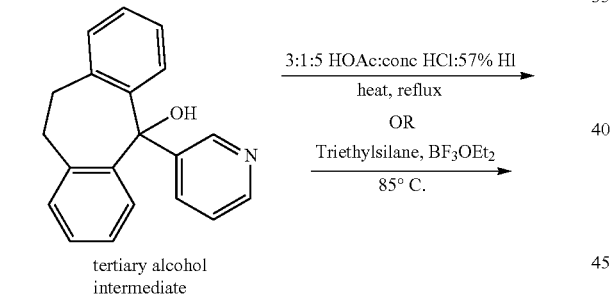

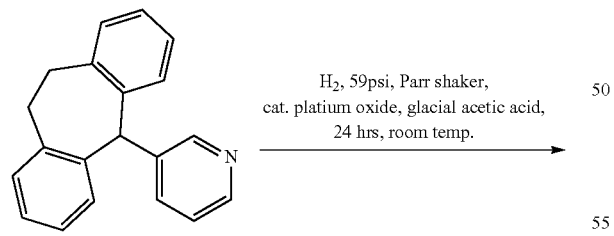

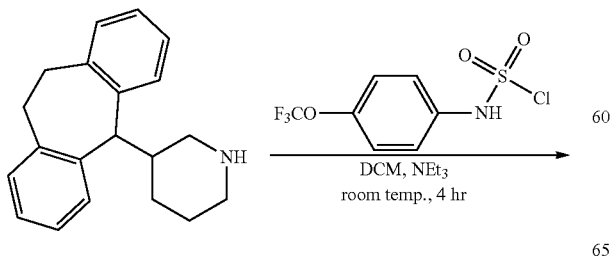

SCHEME D2

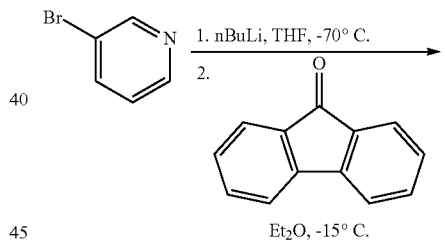

tertiary alcohol intermediate

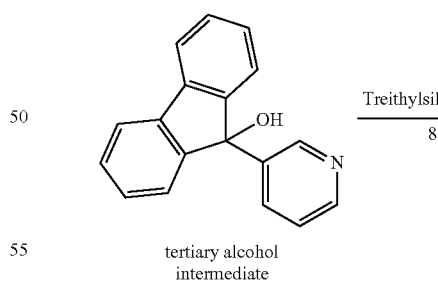

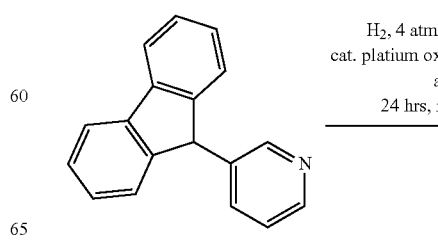

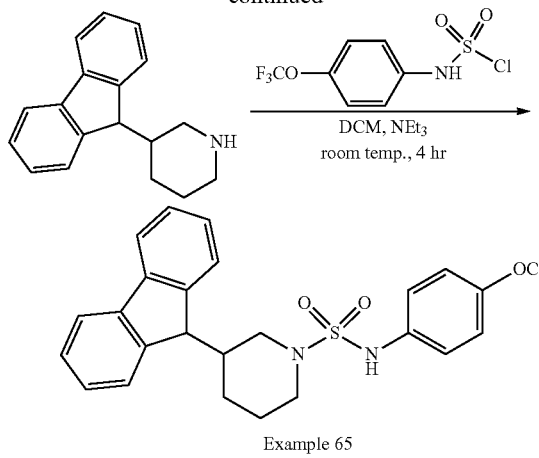

Example 65

Examples in which the bridging group B is a direct bond may be prepared by the route shown in SCHEME D2, which is analogous to D1 except that fluoren-9-one is used as a starting material: synthesis of Example 65 is shown, however other sulfamoyl ureas maybe prepared by use of the appropriately substituted phenyl sulfamoyl chlorides, for instance Example 66. Ureas, urea isosteres, cyclobutendione and thiadiazoledioxide analogs are prepared from 3-(9H-fluoren-9-yl)piperidine using the reactions described in SCHEME C2, C3 and C4 and instances of these are Examples 67 and 68.

Use of substituted cyclic diaryl ketones as starting materials in SCHEMEs D1 or D2, for example 3,6-difluoro-9H-fluoren-9-one, gives access to substituted Examples 69 and 70 as shown in SCHEME D3.

SCHEME D3

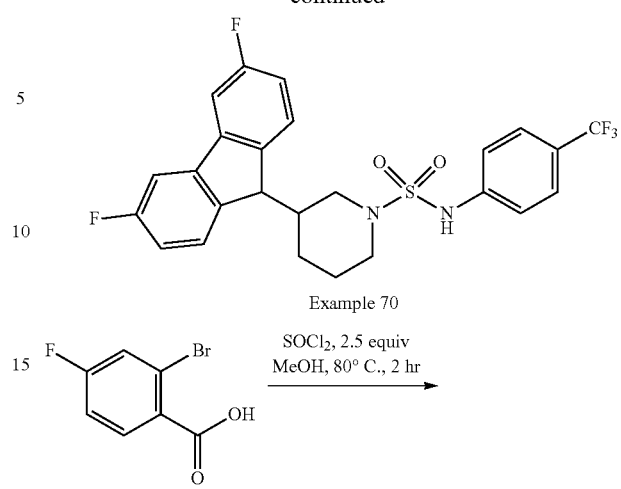

Example 70

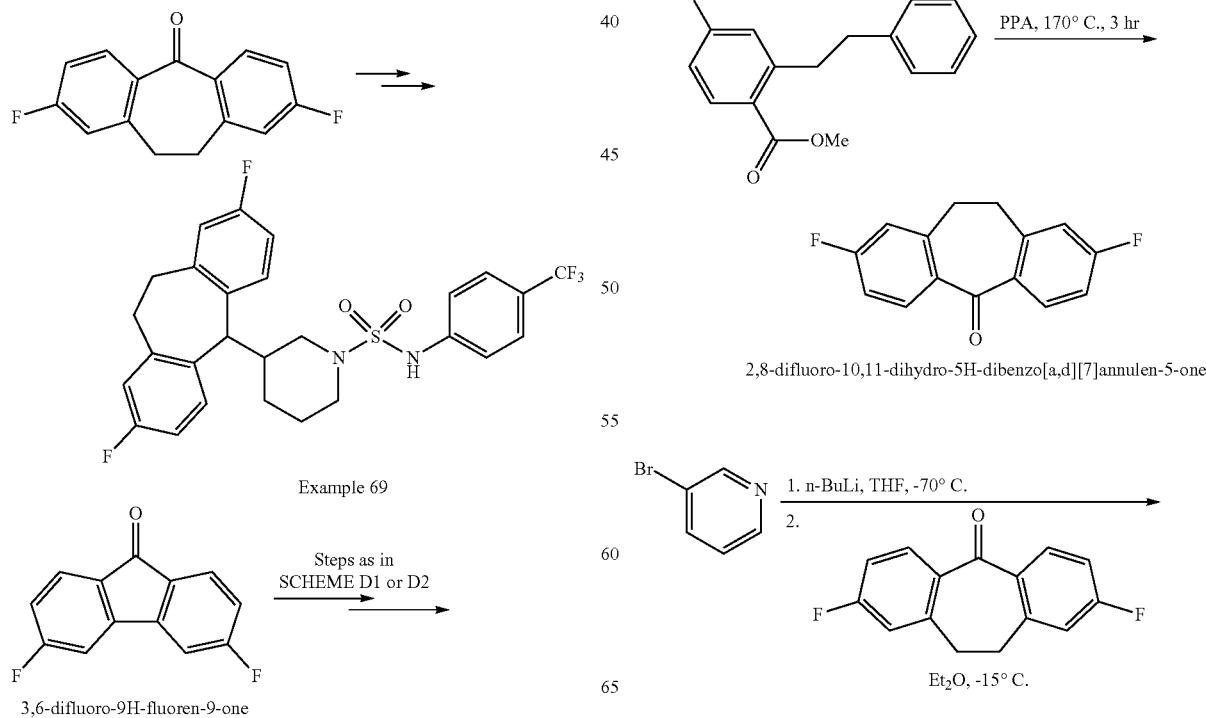

2,8-difluoro-10,11-dihydro-5H-dibenzo[a,d][7]annulen-5-one

-continued

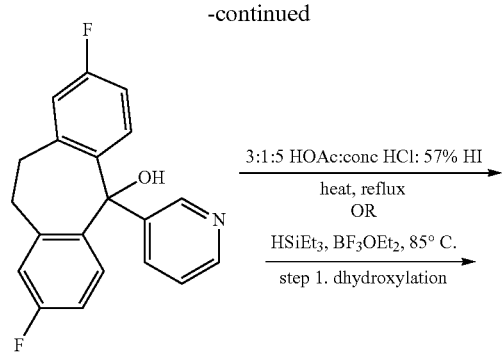

3:1:5 HOAc:conc HCl: 57% HI
heat, reflux
OR
HSiEt₃, BF₃OEt₂, 85° C.

step 1. dhydroxylation

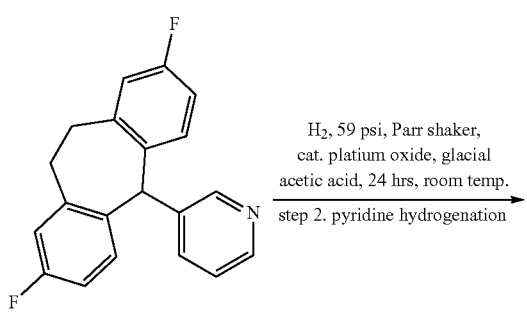

H₂, 59 psi, Parr shaker,
cat. platium oxide, glacial
acetic acid, 24 hrs, room temp.

step 2. pyridine hydrogenation

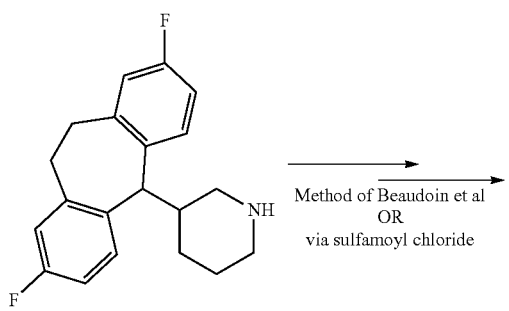

Method of Beaudoin et al
OR
via sulfamoyl chloride

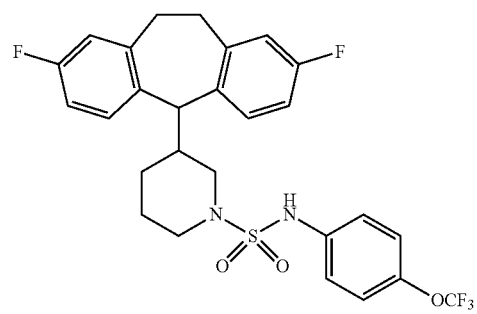

Compounds prepared by the routes shown in SCHEMES D1, D2 and D3 may be accessed in optically pure form by preparative chiral HPLC.

Synthesis of 3-(bis(4-fluorophenyl)methyl)-N-(4-(trifluoromethoxy)phenyl)piperidine-1-sulfonamide. Conditions are adapted from Beaudoin et al, J. Org. Chem. 2003, vol 68, pages 115-119.

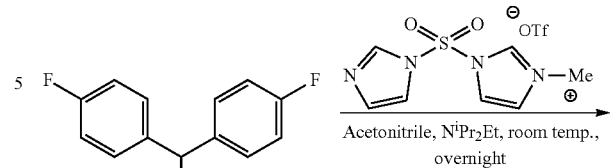

Acetonitrile, N$^i$Pr₂Et, room temp.,
overnight

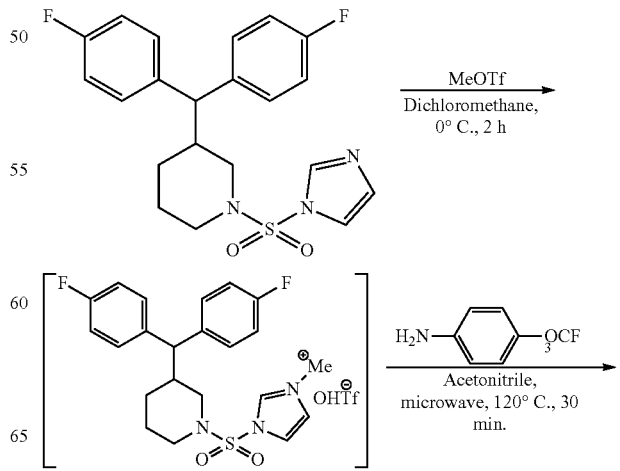

6.44 g (20 mmole, 1 equiv) of 3-(bis(4-fluorophenyl)methyl)piperidine hydrochloride was dissolved in 40 mL dry acetonitrile and 7.2 g (20 mmole, 1 equiv) of freshly prepared 3-(Imidazole-1-sulfonyl)-1-methyl-3H-imidazol-1-ium triflate was added as a solid in one portion with stirring. The mixture was stirred briefly then 3.4 mL (2.6 g, 20 mmole, 1 equiv) of Hunigs base was added. The pale yellow solution was stirred at room temperature over night. The reaction was partly evaporated to remove acetonitrile, then diluted with 200 mL ethyl acetate and washed with water. The solution was dried over sodium sulfate, filtered and evaporated to give a viscous oil which was purified by flash chromatography eluting with 30 to 35% ethyl acetate-hexane. Product, 1-((1H-imidazol-1-yl)sulfonyl)-3-(bis(4-fluorophenyl)methyl)piperidine, is obtained as 2.49 g (6 mmole, 30%), of a viscous clear oil which forms glassy solid foam on pumping under high vacuum. 300 MHz $^1$H NMR in CDCl₃ 7.80 (s, 1H), 7.19-6.94 (overlapping m, 10H), 3.69-3.64 (m, 1H), 3.55-3.46 (m, 2H), 2.73-2.64 (m, 1H), 2.38-2.30 (m, 2H), 1.85-1.78 (m, 1H), 1.70-1.59 (overlapping m, 2H), 1.03-0.97 (m, 1H). TLC-MS ESI +ve 417.9 [M+H]$^+$

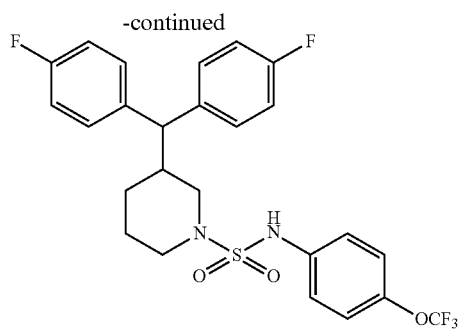

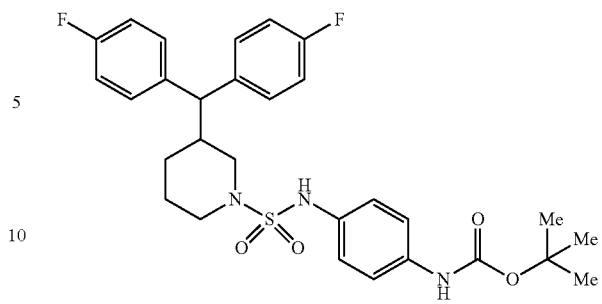

A solution of 2.49 g (6 mmole, 1 equiv) of 1-((1H-imidazol-1-yl)sulfonyl)-3-(bis(4-fluorophenyl)methyl)piperidine in 25 mL dry methylenechloride was cooled to 0° C. with stirring. 0.72 mL of methyl trifluoromethanesulfonate (1.08 g, 6.6 mmole, 1.1 equiv) was added and the mixture stirred at 0° C. for two hours. The solution was evaporated and pumped on for 15 min. The residue was taken up in 20 mL dry acetonitrile and transferred to a microwave vial and 0.89 mL (1.16 g, 6.6 mmole, 1.1 equiv) of 4-(trifluoromethoxy)aniline was added. The mixture was stirred and heated at 120° C. for 30 min. The reaction was diluted into 150 mL ethyl acetate, then washed successively with 50 mL 0.5M HCl and 50 mL sat. aq. NaHCO$_3$. The organic was dried over magnesium sulfate, filtered and evaporated to give crude material which was purified by flash chromatography eluting with 5 to 10% ethyl acetate-hexane. Clear viscous oil forms glassy solid on pumping in vacuo. 3-(bis(4-fluorophenyl)methyl)-N-(4-(trifluoromethoxy)phenyl)piperidine-1-sulfonamide: 300 MHz $^1$H NMR in CDCl$_3$ 7.25-6.94 (overlapping m, 12H), 6.62 (s, 1H), 3.69 (d 11.7 Hz, 1H), 3.47 (d 11.4 Hz, 2H), 2.80 (t 11.7 Hz, 1H), 2.44 (t 12 Hz, 1H), 2.22 (m, 1H), 1.71-1.47 (overlapping m, 3H), 0.97 (m, 1H). TLC-MS ESI –ve ion 525.1 [M–H]$^-$

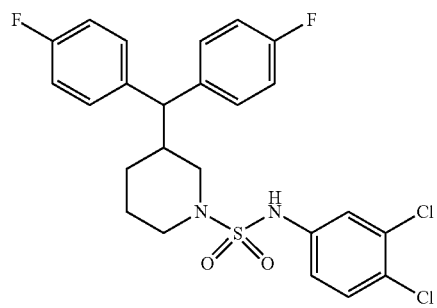 [SMILES: O=S(=O)(Nc1ccc(Cl)c(Cl)c1)N1CCCC(C(c2ccc(F)cc2)c2ccc(F)cc2)C1]

Synthesis of 3-(bis(4-fluorophenyl)methyl)-N-(3,4-dichlorophenyl)piperidine-1-sulfonamide follows the method and conditions above, using 3,4-dichloroaniline in the second coupling step. Thus starting from 0.67 g of 1-((1H-imidazol-1-yl)sulfonyl)-3-(bis(4-fluorophenyl)methyl)piperidine, the product is obtained in as 0.23 g, 28%, of a white crystalline solid after purification by flash chromatography, eluting with 10% ethyl actate-hexane. 300 MHz $^1$H NMR in CDCl$_3$ 7.18-6.92 (overlapping m, 11H), 6.69 (s, 1H), 3.68 (m, 1H), 3.48 (m, 2H), 2.83 (m, 1H), 2.48 (t, 1H), 2.20 (m, 1H). 1.75-1.40 (overlapping m, 3H), 0.99 (m, 1H). TLC-MS ESI –ve ion 508.8 and 510.8 [M–H]$^-$ Synthesis of tert-butyl (4-((3-(bis(4-fluorophenyl)methyl)piperidine)-1-sulfonamido)phenyl)carbamate follows the method and conditions above using tert-butyl (4-aminophenyl)carbamate as the aniline component in the coupling step. Thus starting from 0.4 g (1 mmole, 1 equiv) of 1-((1H-imidazol-1-yl)sulfonyl)-3-(bis(4-fluorophenyl)methyl)piperidine the product is obtained as an off-white solid, 0.212 g, 38% yield, after flash chromatography eluting with 20% ethyl acetate-hexane. 300 MHz $^1$H NMR in CDCl$_3$. 7.32 (m, 2H) 7.13-6.91 (overlapping m, 10H), 6.52 (s, 1H), 6.35 (s, 1H), 3.63 (m, 1H), 3.47 (overlapping m, 2H), 2.74 (m, 1H), 2.41 (m, 1H), 2.21 (m, 1H), 1.63-1.41 (overlapping m, 3H), 1.52 (s, 9H), 0.95 (m, 1H). TLC-MS ESI +ve ion, 557.9 [M+H]$^+$ and 579.7 [M+Na]$^+$ The sulfonyl ureas may also be synthesized by reacting the 3-diarylcyloamine with an aryl sulfamoyl chloride. Synthesis of 3-(bis(4-fluorophenyl)methyl)-N-(4-(trifluoromethoxy)phenyl)piperidine-1-sulfonamide.

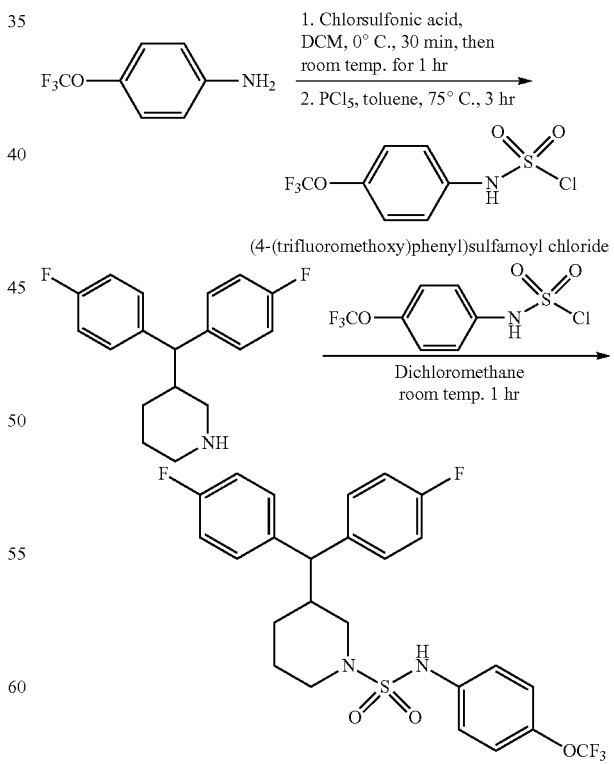

The sulfamoyl chloride was prepared as follows: to a solution of 4-(trifluoromethoxy)aniline (2.00 g, 11.3 mmol) in dry dichloromethane (12 mL), placed in ice bath under argon, was added a solution of chlorsulfonic acid (0.438 g, 3.76 mmol) in dichloromethane (2.0 mL). The reaction mixture was stirred at 0° C. for 30 min, and at room temperature for 1 hr. Precipitate was collected by filtration and dried under high vacuum. The material was suspended in toluene (6.0 mL) and PCl$_5$ (0.782 g, 3.76 mmol) was added. The mixture was stirred at 75° C. for 3 h, cooled to room temperature, and filtered. Solid residue was washed with toluene and filtrate was collected. The filtrate was evaporated and dried under high vacuum. The crude (4-(trifluoromethoxy)phenyl)sulfamoyl chloride (1.01 g) was used for the next step without further purification.

To a solution of (4-(trifluoromethoxy)phenyl)sulfonyl-chloride (550 mg, 2 mmol) in DCM (10 mL) was added 3-(bis(4-fluorophenyl)methyl)piperidine (460 mg, 1.6 mmol). The resulting mixture was stirred at room temperature for 1 hour. The mixture was concentrated under vacuum and purified by chromatography using Biotage (C18 column, eluting with 10% to 95% MeCN in H$_2$O, containing 0.1% TFA) to afford Example 1a (265 mg, 31% yield) as a white solid. HPLC purity: 98.9% @ 214 nm, 100.0% @ 254 nm. LCMS (Shimadzu XR): R$_t$=2.504 min; m/z calculated for [M−H]$^-$525.13, found 525.10. $^1$H NMR, 400 MHz in DMSO-d$_6$: δ 10.03 (1H, s), 7.37-7.03 (12H, aromatic m), 3.66 (1H, d J=11.6 Hz), 3.49 (1H, br d J=11.6 Hz), 3.27 (1H, br d J=12.4 Hz), 2.68 (1H, br t J=11.6), 2.39 (1H, br t J=11 Hz), 2.26 (1H, m), 1.61 (1H, br d), 1.37 (2H, overlapping m), 0.89 (1H, m).

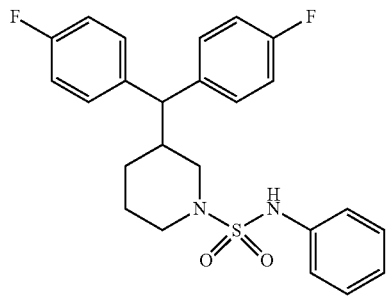 [SMILES: O=S(=O)(Nc1ccccc1)N1CCCC(C(c2ccc(F)cc2)c2ccc(F)cc2)C1]

3-(bis(4-fluorophenyl)methyl)-N-phenylpiperidine-1-sulfonamide was synthesized by the method above using aniline to prepare the sulfamoyl urea: 3-(bis(4-fluorophenyl)methyl)-N-phenylpiperidine-1-sulfonamid (218 mg, 27.5% yield) as a white solid. HPLC purity: 97.3% @ 214 nm, 100.0% @ 254 nm. ESI-MS m/z [MH]$^+$ found, 443.10. $^1$H NMR, 400 MHz in DMSO-d$_6$: δ 9.78 (1H, s), 7.34-7.26 (6H, aromatic m), 7.13-7.04 (7H, aromatic m), 3.66 (1H, d J=11.2 Hz), 3.48 (1H, br d J=12.0 Hz), 3.29 (1H, br d J=12.0 Hz), 2.65 (1H, br t J=12.0), 2.37 (1H, br t J=12.0), 2.26 (1H, br t J=11 Hz), 1.59 (1H, m), 1.34 (2H, overlapping m), 0.87 (1H, m).

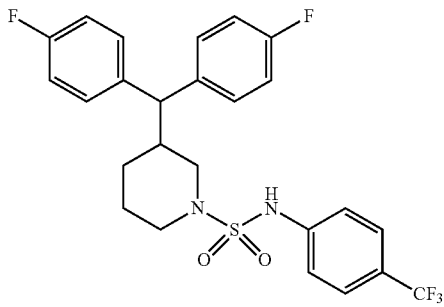

3-(bis(4-fluorophenyl)methyl)-N-(4-(trifluoromethyl)phenyl)piperidine-1-sulfonamide was synthesized by the method above using 4-trifluoromethylaniline to prepare the sulfamoyl urea: 3-(bis(4-fluorophenyl)methyl)-N-(4-(trifluoromethyl)phenyl)piperidine-1-sulfonamide, (220 mg, 24% yield) as a white solid. HPLC purity: 98.5% @ 214 nm, 98.2% @ 254 nm. LCMS (Shimadzu 2200): R$_t$=3.674 min; m/z calculated for [M+H]$^+$ 511.14, found 511.20. $^1$H NMR, 400 MHz in DMSO-d$_6$: δ 10.33 (1H, s), 7.69 (2H, d J=8.8 Hz), 7.32-7.25 (6H, aromatic m), 7.13-7.03 (4H aromatic m), 3.68 (1H, d J=11.2 Hz), 3.52 (1H, br d J=11.2 Hz), 3.29 (1H, br d J=12.0 Hz), 2.70 (1H, br t J=8.8 Hz), 2.41 (1H, br t J=10.0), 2.28 (1H, m), 1.62 (1H, m), 1.36 (2H, overlapping m), 0.92 (1H, m).

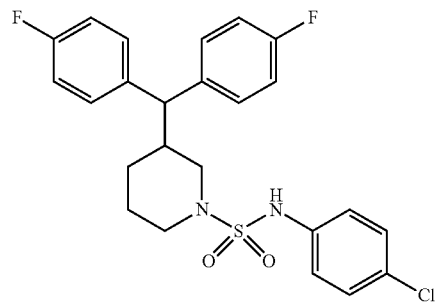 [SMILES: O=S(=O)(Nc1ccc(Cl)cc1)N1CCCC(C(c2ccc(F)cc2)c2ccc(F)cc2)C1]

3-(bis(4-fluorophenyl)methyl)-N-(4-chlorophenyl)piperidine-1-sulfonamide was synthesized by the method above using 4-chloroaniline to prepare the sulfamoyl urea: 3-(bis(4-fluorophenyl)methyl)-N-(4-chlorophenyl)piperidine-1-sulfonamide (228 mg, 26.5% yield) as a white solid. HPLC purity: 100% @ 214 nm, 100% @ 254 nm. LCMS (Shimadzu XR): R$_t$=2.449 min; m/z calculated for [M+H]$^+$ 477.11, found 477.10. $^1$H NMR, 400 MHz in DMSO-d$_6$: δ 9.96 (1H, s), 7.39 (2H, d J=8.8 Hz), 7.33-7.28 (4H, aromatic m), 7.14-7.04 (6H aromatic m), 3.67 (1H, d J=11.6 Hz), 3.48 (1H, br d J=12.0 Hz), 3.28 (1H, br d J=10.4 Hz), 2.64 (1H, br t J=10.8 Hz), 2.37 (1H, br t J=10.0), 2.27 (1H, m), 1.60 (1H, m), 1.39-1.24 (2H, overlapping m), 0.91 (1H, m).

Sulfonyl urea examples where the 3-diaryl moiety are joined to for a ring were synthesized by the method of Beaudoin et al, J. Org. Chem. 2003, vol 68, pages 115-119.

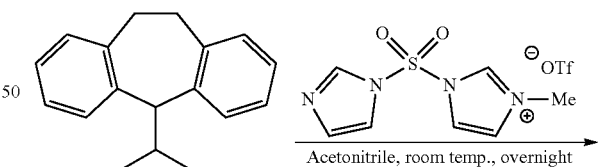

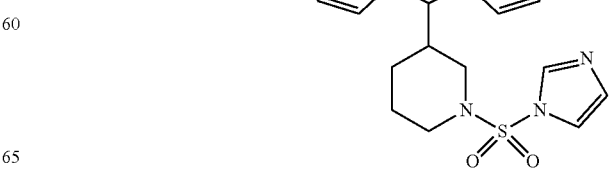

1.38 g (5 mmole, 1 equiv) of 3-(10,11-dihydro-5H-dibenzo[a,d][7]annulen-5-yl)piperidine was dissolved in 20 mL dry acetonitrile and 1.81 g of freshly prepared 3-(Imidazole-1-sulfonyl)-1-methyl-3H-imidazol-1-ium triflate was added as a solid in one portion with stirring. The mixture was stirred at room temperature overnight, then partially evaporated to remove acetonitrile to give a pale yellow mobile oil. Ethyl acetate, 100 mL, was added and the organic was washed with 50 mL water, then dried over sodium sulfate, filtered, and evaporated to give crude product. This material was purified by flash chromatography eluting with 30% ethyl acetate-hexane, to give 1.1 g (2.1 mmole, 54%) of product as a crystalline white solid. 300 MHz $^1$H NMR in CDCl$_3$ 7.74 (s, 1H), 7.13-7.01 (overlapping m, 10H), 3.63 (m, 1H), 3.61-3.37 (overlapping m, 4H), 3.01-2.85 (m, 2H), 2.67 (m, 1H), 2.40 (m, 2H), 1.76 (m, 1H), 1.52 (m, 1H), 1.45 (m, 1H), 0.97 (m, 1H). TLC-MS ESI +ve ion, 408.2 [M+H]$^+$

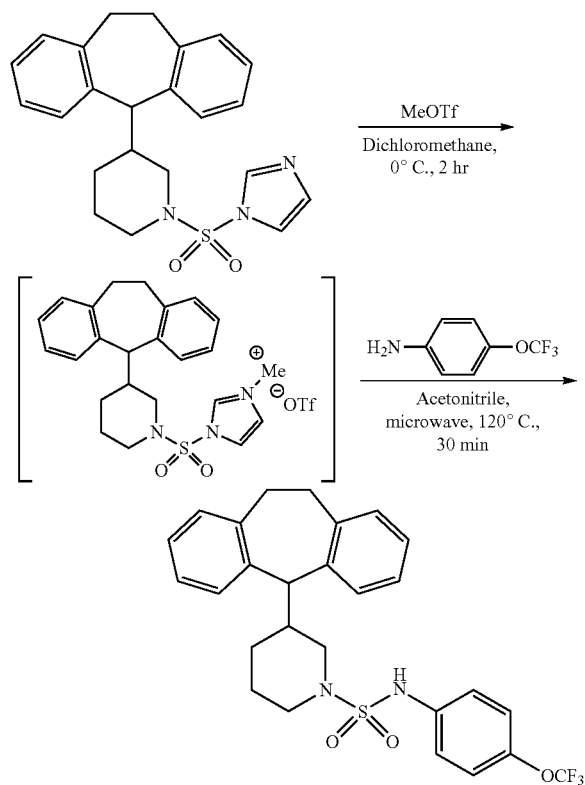

0.81 g (2 mmole, 1 equiv) of 1-((1H-imidazol-1-yl)sulfonyl)-3-(10,11-dihydro-5H-dibenzo[a,d][7]annulen-5-yl)piperidine was dissolved in 15 mL dichloromethane and cooled to 0° C. with stirring. Methyl trifluoromethanesulfonate, 0.24 mL (0.36 g, 2.2 mmole, 1.1 equiv) was added. Dense white precipitate formed after about 10 min. Mixture was stirred at 0° C. for 2 hr. Solvent was evaporated and white residue was transferred to microwave vial using 15 mL dry acetonitrile. 4-trifluoromethoxyaniline was added and the mixture was stirred and heated in microwave at 120° C. for 30 min. Reaction was diluted into 100 mL ethyl acetate and washed twice with 1M HCl aq, then once with sat. aq. NaHCO$_3$, and dried over magnesium sulfate. Solution was filtered and evaporated to give crude product as an oil which was purified by flash chromatography, eluting with 5 to 10% ethyl acetate-hexane. Product from column was initially viscous a oil which crystallized on standing and the solid was washed with hexane, to give 0.477 g (0.92 mmole, 46%) of white crystalline solid. 300 MHz $^1$H NMR in CDCl$_3$ 7.14-6.88 (overlapping m, 12H), 3.67 (m, 1H), 3.41-3.25 (overlapping m, 4H), 2.90-2.83 (overlapping m, 3H), 2.47 (m, 1H), 2.17 (m, 1H), 1.65 (m, 1H), 1.49 (m, 1H), 1.35 (m, 1H), 0.97 (m, 1H). TLC-MS ESI +ve ion, 516.9 [M+H]$_+$, −ve ion 514.9 [M−H]$^-$.

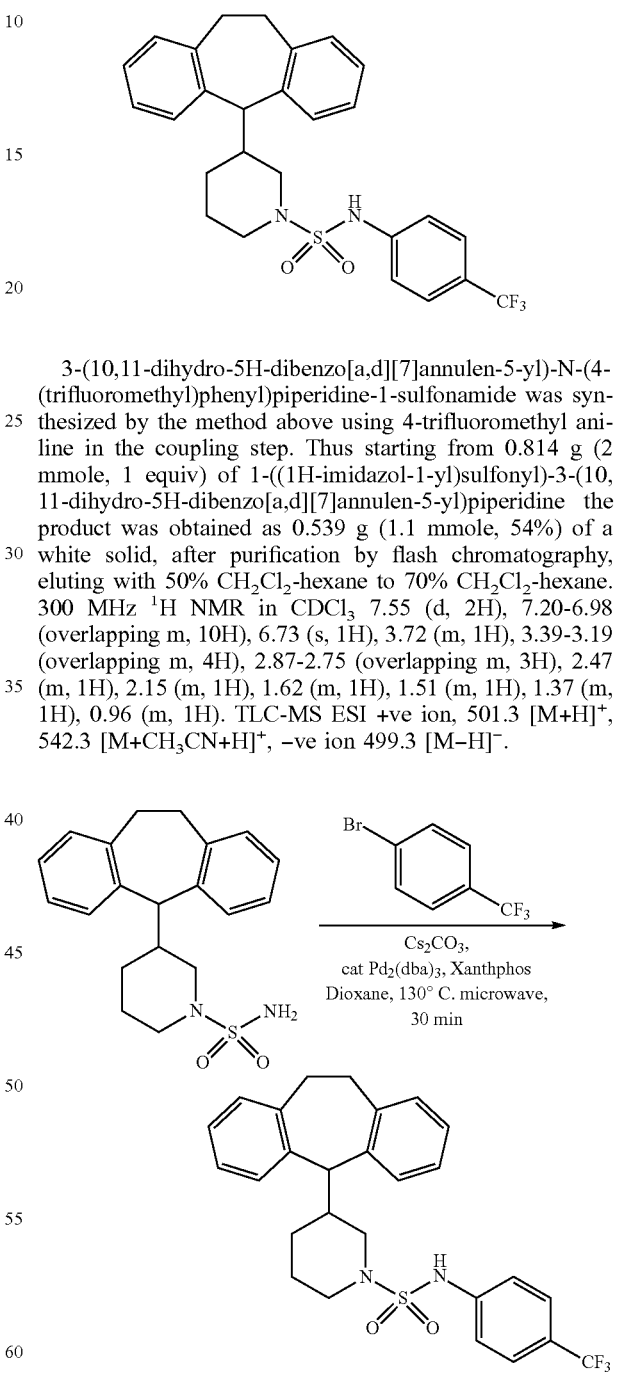

3-(10,11-dihydro-5H-dibenzo[a,d][7]annulen-5-yl)-N-(4-(trifluoromethyl)phenyl)piperidine-1-sulfonamide was synthesized by the method above using 4-trifluoromethyl aniline in the coupling step. Thus starting from 0.814 g (2 mmole, 1 equiv) of 1-((1H-imidazol-1-yl)sulfonyl)-3-(10,11-dihydro-5H-dibenzo[a,d][7]annulen-5-yl)piperidine the product was obtained as 0.539 g (1.1 mmole, 54%) of a white solid, after purification by flash chromatography, eluting with 50% CH$_2$Cl$_2$-hexane to 70% CH$_2$Cl$_2$-hexane. 300 MHz $^1$H NMR in CDCl$_3$ 7.55 (d, 2H), 7.20-6.98 (overlapping m, 10H), 6.73 (s, 1H), 3.72 (m, 1H), 3.39-3.19 (overlapping m, 4H), 2.87-2.75 (overlapping m, 3H), 2.47 (m, 1H), 2.15 (m, 1H), 1.62 (m, 1H), 1.51 (m, 1H), 1.37 (m, 1H), 0.96 (m, 1H). TLC-MS ESI +ve ion, 501.3 [M+H]$^+$, 542.3 [M+CH$_3$CN+H]$^+$, −ve ion 499.3 [M−H]$^-$.

3-(10,11-dihydro-5H-dibenzo[a,d][7]annulen-5-yl)-N-(4-(trifluoromethyl)phenyl)piperidine-1-sulfonamide was also prepared by arylation of 3-(10,11-dihydro-5H-dibenzo[a,d][7]annulen-5-yl)piperidine-1-sulfonamide using conditions adapted from Alcaraz et al, Organic Letters, vol 6, pages 2705-2701. Thus, a 35 mL microwave vial was charged with 0.178 g (0.5 mmole, 1 equiv) 3-(10,11-dihydro-5H-dibenzo[a,d][7]annulen-5-yl)piperidine-1-sulfonamide, 0.14 g (0.08 mL, 0.6 mmole 1.2 equiv), cesium carbonate, 0.23 g (0.7 mmole, 1.4 equiv), and catalyst XantPhos, 22 mg (7.5 mole %) and Pd$_2$(dba)$_3$, 13 mg (2.5 mole %). 10 mL dry dioxane was added and the mixture was sparged briefly with argon, sealed and heated at 130° C. for 30 min. Reaction was diluted into 100 mL ethtyl acetate, washed with water and organic was dried over magnesium sulfate. Filtration and evaporation gives crude material as a yellow oil which was purified by flash chromatography, eluting with 5 to 10% ethyl acetate hexane. Material gives glassy foam under vacuumed, 104 mg, 41% of product with $^1$H NMR and TLC-MS as above.

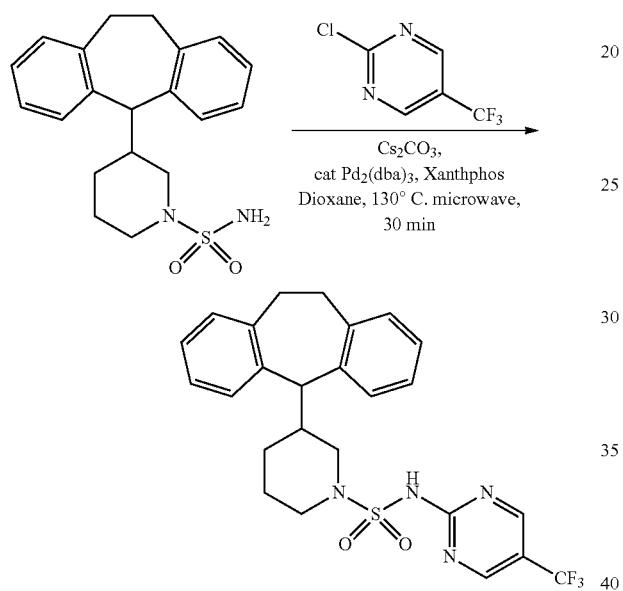

3-(10,11-dihydro-5H-dibenzo[a,d][7]annulen-5-yl)-N-(5-(trifluoromethyl)pyrimidin-2-yl)piperidine-1-sulfonamide was synthesized using the conditions above using 2-chloro-5-(trifluoromethyl)pyrimidine. 300 MHz $^1$H NMR in CDCl$_3$ 8.51 (s, 1H), 7.83 (m, 2H), 7.09-6.88 (overlapping m, 8H), 3.77 (m, 1H), 3.39-3.18 (overlapping m, 4H), 2.88-2.81 (overlapping m, 3H), 2.44 (m, 1H), 2.25 (m, 1H), 1.71-1.54 (overlapping m), 1.41 (m, 1H), 0.95 (m, 1H). TLC-MS ESI +ve ion, 503.2 [M+H]$^+$.

3-(2,8-difluoro-10,11-dihydro-5H-dibenzo[a,d][7]annulen-5-yl)piperidine was prepared as shown in the scheme above and used in sulfonyl urea synthesis following the method described by Beaudoin et al, J. Org. Chem. 2003, vol 68, pages 115-119.

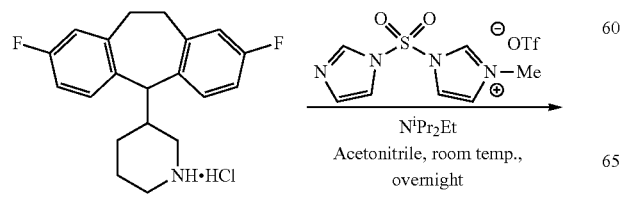

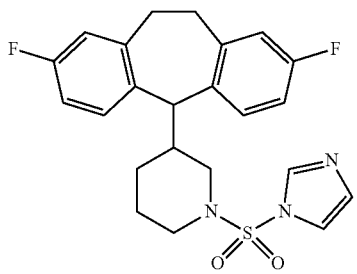

3.13 g (10 mmole, 1 equiv) of 1-((1H-imidazol-1-yl)sulfonyl)-3-(2,8-difluoro-10,11-dihydro-5H-dibenzo[a,d][7]annulen-5-yl)piperidine hydrochloride was dissolved in 50 mL dry acetonitrile and 2.0 mL (1.52 g, 12 mmole, 1.2 equiv) of diisopropylethylamine was added. 5.5 g of freshly prepared 3-(Imidazole-1-sulfonyl)-1-methyl-3H-imidazol-1-ium triflate was added as a solid in one portion with stirring. The mixture was stirred at room temperature overnight, then partially evaporated to remove acetonitrile to give a pale yellow mobile oil. Ethyl acetate, 250 mL, was added and the organic was washed with 100 mL water and the aqueous was back extracted with 50 mL ethyl acetate. Combined ethyl acetate was washed with saturated aqueous brine, then dried over sodium sulfate, filtered, and evaporated to give crude product. This material was purified by flash chromatography eluting with 30% ethyl acetate-hexane, to give 1.5 g (3.3 mmole, 33%) of product as a foam on evaporation, which is a glassy solid on pumping in vacuo. 300 MHz $^1$H NMR in CDCl$_3$ 7.76 (s, 1H), 7.13 (m, 2H), 7.00 (m, 2H), 6.90-6.74 (overlapping m, 4H), 3.57 (m, 1H), 3.49-3.31 (overlapping m, 4H), 2.89 (m, 2H), 2.72 (dt, 1H), 2.47-2.32 (m, 2H), 2.77 (m, 1H), 1.48 (overlapping m, 2H), 0.98 (m, 1H). TLC-MS ESI +ve ion, 444.6 [M+H]$^+$ and 485.6 [M+CH$_3$CN+H]$^+$.

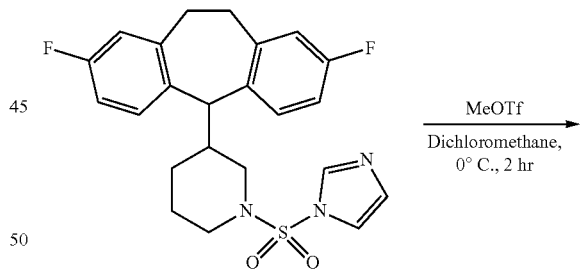

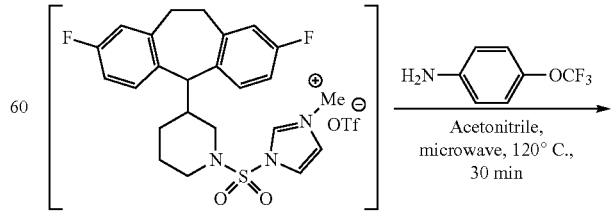

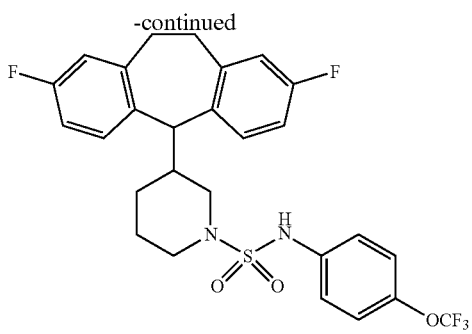

1.5 g (3.3 mmole, 1 equiv) of 1-((1H-imidazol-1-yl)sulfonyl)-3-(2,8-difluoro-10,11-dihydro-5H-dibenzo[a,d][7]annulen-5-yl)piperidine was dissolved in 20 mL dichloromethane and cooled to 0° C. with stirring. Methyl trifluoromethanesulfonate, 0.41 mL (0.61 g, 4 mmole, 1.1 equiv) was added. Dense white precipitate formed after about 5 min. Suspension was stirred at 0° C. for 2 hr. Solvent was evaporated and white residue was transferred, as a solution using 15 mL dry acetonitrile, to a microwave vial. 4-trifluoromethoxyaniline, 0.54 mL (0.71 g, 4 mmole, 1.1 equiv) was added and the mixture was stirred and heated in microwave at 120° C. for 30 min. Reaction was diluted into 100 mL ethyl acetate and washed one with 1M HCl aq, then once with sat. aq. NaHCO$_3$, and dried over magnesium sulfate. Solution was filtered and evaporated to give crude product as an oil which was purified by flash chromatography, eluting with 5 to 10% ethyl acetate-hexane. Product from column was initially viscous a oil which crystallized on standing. The solid was recrystallized from dichloromethane-hexane, filtered and washed with hexane and dried in vacuo. Product, 3-(2,8-difluoro-10,11-dihydro-5H-dibenzo[a,d][7]annulen-5-yl)-N-(4-(trifluoromethoxy)phenyl)piperidine-1-sulfonamide was obtained as 1.06 g (1.9 mmole, 57%) of white crystalline solid. 300 MHz $^1$H NMR in CDCl$_3$ 7.13 (m, 2H), 7.04-6.92 (overlapping m, 4H), 6.85-6.72 (overlapping m, 4H), 6.67 (s, 1H), 3.65 (m, 1H), 3.39-3.22 (overlapping m, 4H), 2.86-2.74 (overlapping m, 3H), 2.5 (m, 1H), 2.14 (m, 1H), 1.71-1.38 (overlapping m, 3H), 0.98 (m, 1H). TLC-MS ESI –ve ion 551.6 [M–H]$^-$.

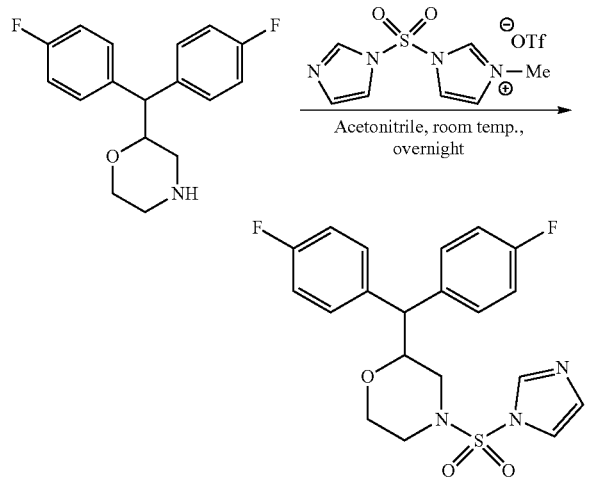

5.43 g (15 mmole, 1.5 equiv) of freshly prepared 3-(Imidazole-1-sulfonyl)-1-methyl-3H-imidazol-1-ium triflate was dissolved in 50 mL dry acetonitrile. A solution of 2.89 g of 2-(bis(4-fluorophenyl)methyl)morpholine in 20 mL dry acetonitrile was added and the mixture stirred over night at room temperature. Mixture was evaporated to give mobile orange oil, which was loaded directly onto a flash chromatography column and eluted with 40% ethyl acetate-hexanes. Product crystallizes to give white solid. 300 MHz $^1$H NMR in CDCl$_3$ 7.82 (s, 1H), 7.21-6.95 (overlapping m, 10H), 4.12 (dt, 1H), 3.96 (dd, 1H), 3.88 (d, 1H), 3.69-3.59 (overlapping m, 2H), 3.44 (d, 1H), 2.68 (dt, 1H), 2.31 (t, 1H). TLC-MS ESI +ve ion, 420.4 [M+H]$^+$ and 461.5 [M+CH$_3$CH+H]$^+$.

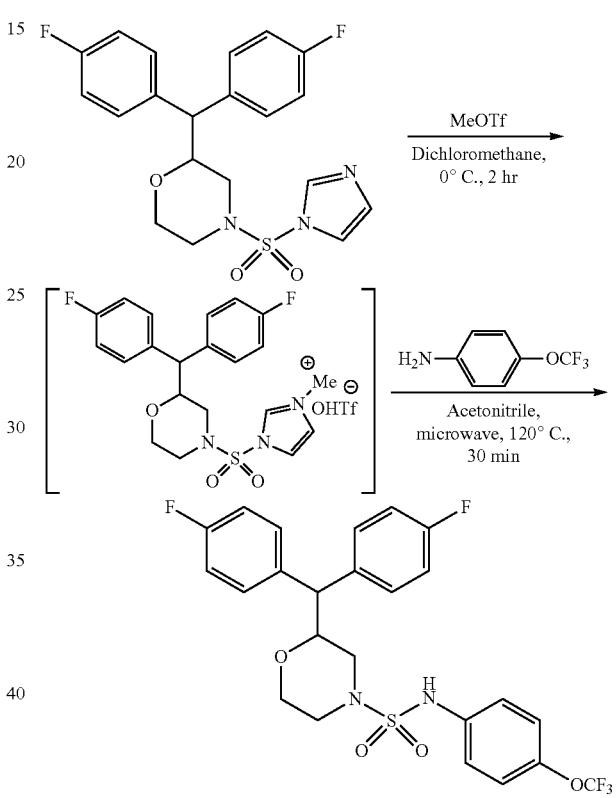

2-(bis(4-fluorophenyl)methyl)-N-(4-(trifluoromethoxy)phenyl)morpholine-4-sulfonamide was prepared by conditions adapted from Beaudoin et al, J. Org. Chem. 2003, vol 68, pages 115-119. Thus 0.83 g (2 mmole, 1 equiv) of 4-((1H-imidazol-1-yl)sulfonyl)-2-(bis(4-fluorophenyl)methyl)morpholine was dissolved in 10 mL dry dichloromethane and cooled to 0° C. 0.24 mL (0.36 g, 2.2 mmole, 1.1 equiv) of methyl trifluoromethanesulfonate was added and the mixture stirred at 0° C. for 2 hours. The solution was evaporated and pumped on briefly, then the residue transferred to a microwave vial with 10 mL dry acetonitrile. 0.3 mL (0.39 g, 2.2 equiv) of 4-trifluoromethoxyaniline was added and the mixture heated at 120° C. for 30 min in a CEM microwave. Pale yellow solution (with small quantity of colorless precipitate) was diluted into 100 mL ethyl actate and washed with 50 mL water, then the organic was dried over magnesium sulfate. Filtration and evaporation gives the crude material which was purified by flash chromatography, eluting with 5 to 10% ethyl acetate hexane to give the product as a clear viscous oil. Tituration with 1:2 dichloromethane:hexane gives a semi-solid from which solvent is decanted, and pumping on residue gives product as foam which forms glassy solid, 0.63 g, (1.2 mmole), 60% yield. 300 MHz ¹H NMR in CDCl₃ 7.20-6.93 (overlapping m, 12H), 6.55 (s, 1H), 3.97-3.85 (overlapping m, 3H), 3.52 (m, 2H), 3.33 (d 12 Hz, 1H), 2.92 (m, 1H), 2.59 (m, 1H). TLC-MS ESI –ve ion 527.6 [M–H]⁻.

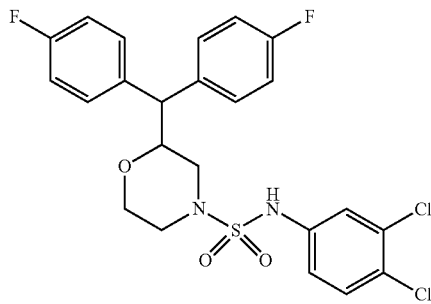 [SMILES: O=S(=O)(Nc1ccc(Cl)c(Cl)c1)N1CCOC(C(c2ccc(F)cc2)c2ccc(F)cc2)C1]

2-(bis(4-fluorophenyl)methyl)-N-(3,4-dichlorophenyl) morpholine-4-sulfonamide was prepared via the method above using 3,4-dichloroaniline in the coupling step. 300 MHz ¹H NMR in CDCl₃ 7.37 (d, 2H), 7.21-6.91 (overlapping m, 9H) 6.47 (s, 1H), 4.02--3.87 (overlapping m, 3H), 3.55 (m, 2H), 3.33 (d 12 Hz, 1H), 2.92 (m, 1H), 2.60 (m, 1H). TLC-MS ESI –ve ion 511.5, 513.5 [M–H]⁻.

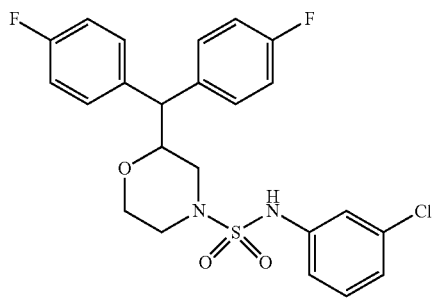 [SMILES: O=S(=O)(Nc1cccc(Cl)c1)N1CCOC(C(c2ccc(F)cc2)c2ccc(F)cc2)C1]

2-(bis(4-fluorophenyl)methyl)-N-(3-chlorophenyl)morpholine-4-sulfonamide was prepared by the method above using 3-chloroaniline in the coupling step. 300 MHz ¹H NMR in CDCl₃ 7.22-6.93 (overlapping m, 12H), 6.59 (s, 1H), 4.00-3.86 (overlapping m, 3H), 3.57-3.48 (overlapping m, 2H), 3.34 (d 12 Hz, 1H), 2.90 (m, 1H), 2.59 (m, 1H). TLC-MS ESI –ve ion 477.5 [M–H]⁻.

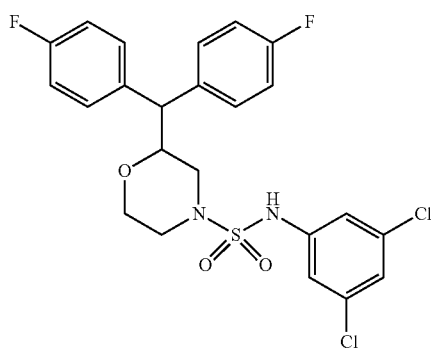 [SMILES: O=S(=O)(Nc1cc(Cl)cc(Cl)c1)N1CCOC(C(c2ccc(F)cc2)c2ccc(F)cc2)C1]

2-(bis(4-fluorophenyl)methyl)-N-(3,5-dichlorophenyl) morpholine-4-sulfonamide was prepared by the method above using 3,5-dichloroaniline in the coupling step. 300 MHz ¹H NMR in CDCl₃ 7.21-6.94 (overlapping m, 11H) 6.59 (s, 1H), 3.99-3.87 (overlapping m, 3H), 3.58-3.50 (overlapping m, 2H), 3.34 (d 12 Hz, 1H), 2.95 (m, 1H), 2.62 (m, 1H). TLC-MS ESI –ve ion 511.5, 513.5 [M–H]⁻.

Examples of moripholine-4-sulfonamides wherein the central ring is morpholino have also been prepared via the sulfamoyl chloride route. For example:

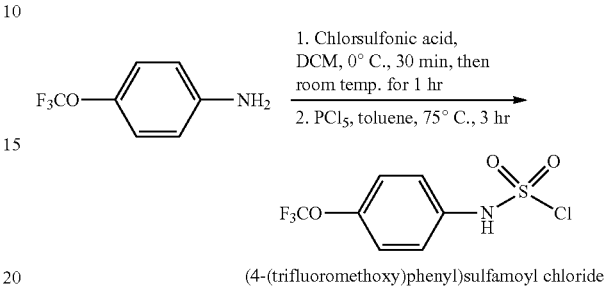

(4-(trifluoromethoxy)phenyl)sulfamoyl chloride

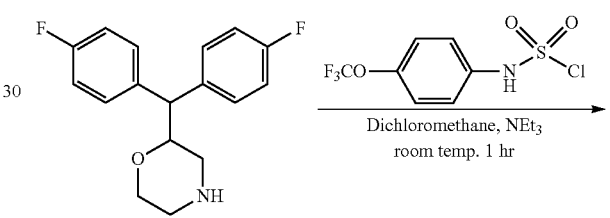

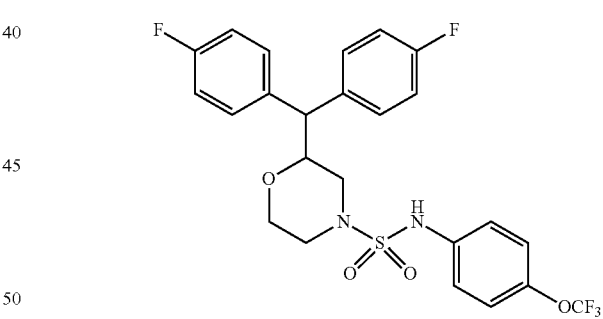

To a solution of (4-(trifluoromethoxy)phenyl)sulfamoyl chloride, 0.595 g (2.16 mmole) in 10 mL dichloromethane was added 2-(bis(4-fluorophenyl)methyl)morpholine, 0.500 g (1.73 mmole) and triethylamine, 0.656 g (6.48 mmole). The mixture was stirred at room temperature for 1 hour then evaporated and purified by reverse phase HPLC (C18 column, eluting with 10% to 95% MeCN in H₂O, containing 0.1% TFA) to afford 2-(bis(4-fluorophenyl)methyl)-N-(4-(trifluoromethoxy)phenyl)morpholine-4-sulfonamide (250 mg, 22% yield) as a white solid. 300 MHz ¹H NMR in DMSO-d₆ 10.20 (br s, 1H), 7.36-7.03 (overlapping m, 12H), 4.13-4.04 (overlapping m, 2H), 3.82 (m, 1H), 3.43-3.36 (m, 2H), 3.14 (m, 1H), 2.72 (m, 1H), 2.45 (m, 1H). LC-MS ESI –ve ion 527.1 [M–H]⁻.

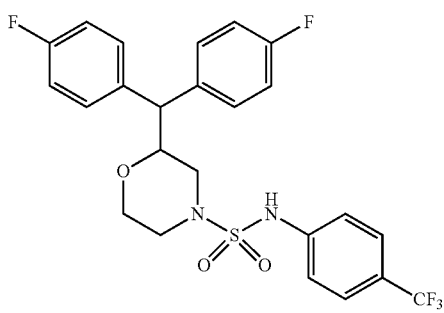 [SMILES: O=S(=O)(Nc1ccc(C(F)(F)F)cc1)N1CCOC(C(c2ccc(F)cc2)c2ccc(F)cc2)C1]

2-(bis(4-fluorophenyl)methyl)-N-(4-(trifluoromethyl)phenyl)morpholine-4-sulfonamide was synthesized by the same route using (4-trifluoromethylphenyl)sulfamoyl chloride. 300 MHz $^1$H NMR in DMSO-$d_6$ 10.50 (br s, 1H), 7.68 (d, 2H), 7.36-7.28 (overlapping m, 6H), 7.15-7.03 (overlapping m, 4H), 4.16-4.07 (overlapping m, 2H), 3.82 (m, 1H), 3.46-3.42 (m, 2H), 3.16 (m, 1H), 2.73 (m, 1H) 2.40 (m, 1H). LC-MS ESI –ve ion 511.1 [M–H]$^-$.

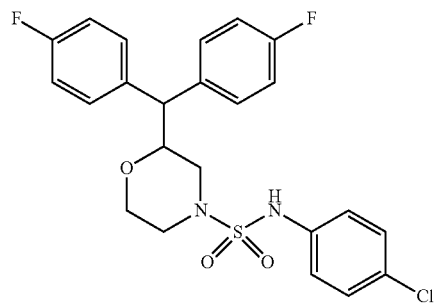

2-(bis(4-fluorophenyl)methyl)-N-(4-chlorophenyl)morpholine-4-sulfonamide was synthesized by the same route using (4-chlorophenyl)sulfamoyl chloride. 300 MHz $^1$H NMR in DMSO-$d_6$ 10.13 (s, 1H), 7.39-7.30 (overlapping m, 6H), 7.16-7.04 (overlapping m, 6H), 4.14-4.03 (overlapping m, 2H), 3.79 (m, 1H), 3.44-3.36 (m, 2H), 3.14 (m, 1H), 2.66 (m, 1H), 2.50 (m, 1H). LC-MS ESI –ve ion 477.1 [M–H]$^-$.

Examples where L is a substituted alkyl group, for example benzyl and the like, were prepared by alkylation of N-Boc sulfamides followed by deprotection as shown in the examples below.

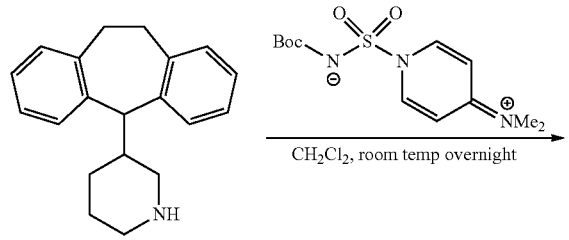

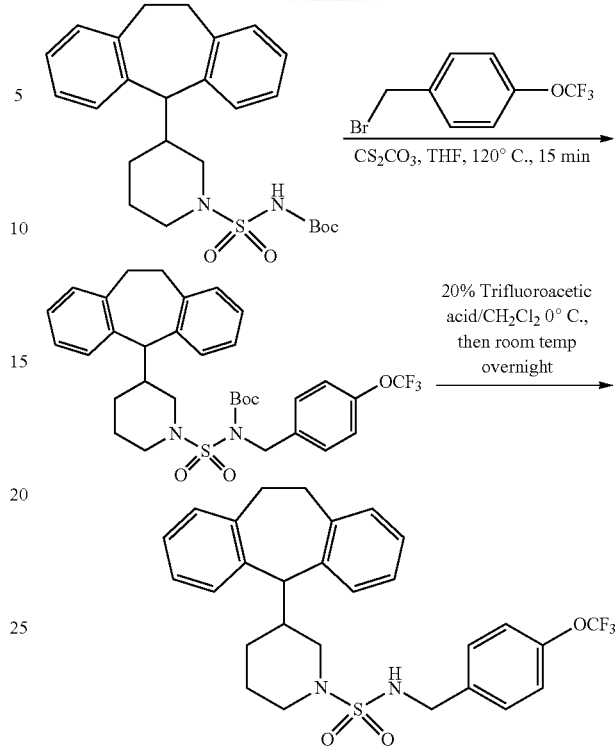

Step 1. Synthesis and use of N-(tert-butoxycarbonyl)-N-[4-(dimethylazaniumylidene)-1,4-dihydropyridin-1-ylsulfonyl]-azanide as a sulfamolyating reagent is described in Winum et al, Organic Letters, vol 3, pages 2241-2243.

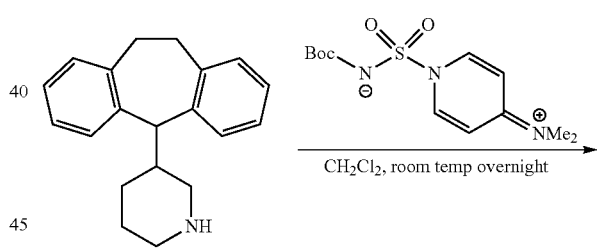

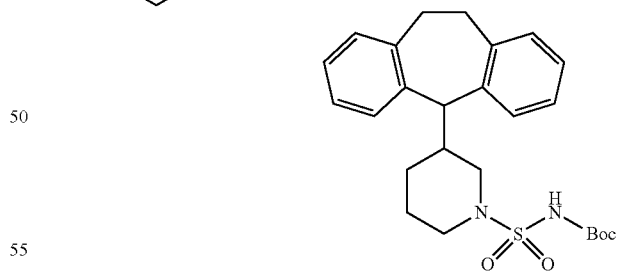

A solution of 1.44 g (5.2 mmole, 1 equiv) of 3-(10,11-dihydro-5H-dibenzo[a,d][7]annulen-5-yl)piperidine in 10 mL dichloromethane was treated with 1.7 g (5.7 mmole 1.1 equiv) of N-(tert-butoxycarbonyl)-N-[4-(dimethylazaniumylidene)-1,4-dihydropyridin-1-ylsulfonyl]-azanide. The mixture was stirred at room temperature for 2 hours, then diluted with 100 mL dichloromethane and washed with 0.1 M aq hydrochloric acid the sat. aqueous sodium bicarbonate. The organic was dried over sodium sulfate, filtered and evaporated to give crude product. Material was purified by flash chromatography eluting with 15 to 20% ethyl acetate-hexane. Product, tert-butyl ((3-(10,11-dihydro-5H-dibenzo[a,d][7]annulen-5-yl)piperidin-1-yl)sulfonyl)carbamate is a white crystalline solid, 1.77 g, 75% yield. 300 MHz $^1$H NMR in CDCl$_3$ 7.20-7.05 (overlapping m, 8H), 6.85 (s, 1H), 3.65-3.53 (m, 1H), 3.52-3.42 (overlapping m, 5H), 3.03-2.86 (overlapping m, 4H), 2.71 (m, 1H), 2.56 (m, 1H), 1.81-1.60 (overlapping m, 3H), 1.45 (s, 9H), 1.08 (m, 1H). TLC-MS ESI +ve ion 479.0 [M+Na]$^+$.

Step 2. Alkylation

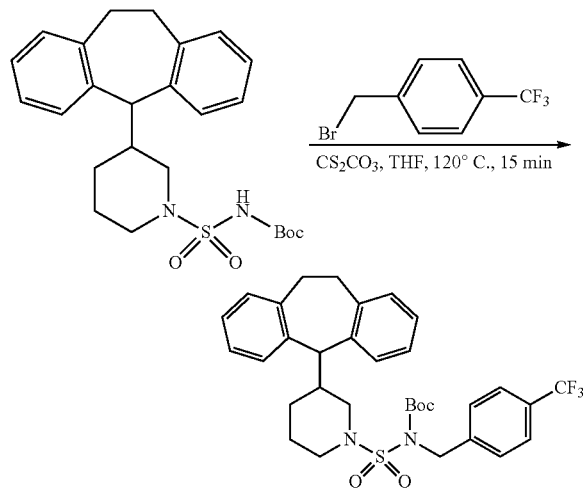

A microwave vial was charged with 0.23 g (0.5 mmole, 1 equiv) of tert-butyl ((3-(10,11-dihydro-5H-dibenzo[a,d][7]annulen-5-yl)piperidin-1-yl)sulfonyl)carbamate, 0.1 mL (0.13 g, 0.55 mmole, 1.1 equiv) of 4-trifluoromethylbenzylbromide and 0.18 g (0.55 mmole, 1.1 equiv) cesium carbonate. 10 mL dry THF was added, the vial sealed, and mixture stirred and heated at 100° C. in CEM microwave for 30 min. reaction mixture was diluted into 75 mL ethyl acetate and washed with water once, the dried over magnesium sulfate. Filtration and evaporation gives crude product which was purified by flash chromatography, eluting with 5 to 10% ethyl acetate hexanes. Clear oil crystallizes to give product as white crystalline solid: tert-butyl ((3-(10,11-dihydro-5H-dibenzo[a,d][7]annulen-5-yl)piperidin-1-yl)sulfonyl)(4-(trifluoromethyl)benzyl)carbamate. 300 MHz $^1$H NMR in CDCl$_3$ 7.58 (d, 2H), 7.40 (d, 2H), 7.20-7.07 (overlapping m, 8H), 4.81-4.67 (m(diastereotopic CH$_2$), 2H), 3.59-3.38 (overlapping m, 5H), 2.98-2.86 (overlapping m, 3H), 2.63 (m, 1H), 2.50 (m, 1H), 1.68 (m, 2H), 1.50 (m, 1H), 1.42 (s, 9H), 1.12 (m, 1H). TLC-MS ESI +ve ion 515.2 [M-Boc]$^+$, 637.4 [M+Na]$^+$.

Step 3. Boc Deprotection.

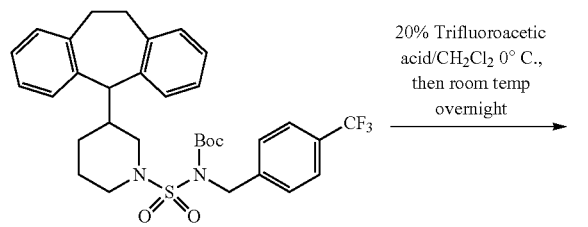

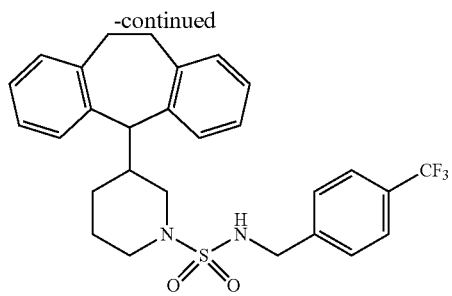

tert-butyl ((3-(10,11-dihydro-5H-dibenzo[a,d][7]annulen-5-yl)piperidin-1-yl)sulfonyl)(4-(trifluoromethyl)benzyl carbamate was deprotected by dissolving in 8 mL dichloromethane then cooling to 0° C., adding 2 mL trifluoroacetic acid, and stirring at room temperature overnight. Reaction was diluted with 75 mL ethyl acetate and washed with sat aq. sodium bicarbonate twice and dried over magnesium sulfate. Filtration and evaporation gives the product, 3-(10,11-dihydro-5H-dibenzo[a,d][7]annulen-5-yl)-N-(4-(trifluoromethyl)benzyl)piperidine-1-sulfonamide, as white crystalline solid, 194 mg (0.38 mmole), 75% over steps 2 and 3. 300 MHz $^1$H NMR in CDCl$_3$ 7.60 (d, 2H), 7.25 (d, 2), 7.21-7.06 (overlapping m, 8H), 4.32 (m, 1H), 4.16 (overlapping m, 2H), 3.59 (m, 1H), 3.51-3.38 (overlapping m, 4H), 2.97-2.85 (m, 2H), 2.75-2.67 (m, 1H), 2.48-2.39 (m, 3H), 1.75-1.41 (overlapping m, 3H), 1.05 (m, 1H). TLC-MS ESI +ve ion 515.2 [M+H]$^+$.

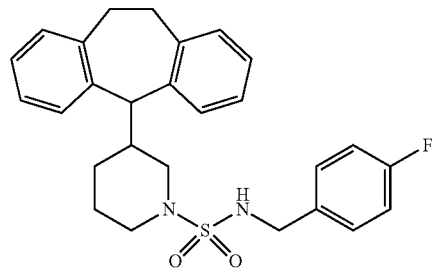 [SMILES: O=S(=O)(NCc1ccc(F)cc1)N1CCCC(C2c3ccccc3CCc3ccccc32)C1]

3-(10,11-dihydro-5H-dibenzo[a,d][7]annulen-5-yl)-N-(4-fluorobenzyl)piperidine-1-sulfonamide was synthesized starting from tert-butyl ((3-(10,11-dihydro-5H-dibenzo[a,d][7]annulen-5-yl)piperidin-1-yl)sulfonyl)carbamate with 4-fluorobenzylbromide in the alkylation step followed by Boc deprotection as above. 300 MHz $^1$H NMR in CDCl$_3$ 7.20-6.97 (overlapping m, 8H), 4.14 (m, 1H), 4.07 (m, 2H), 3.59 (m, 1H), 3.52-3.38 (overlapping m, 4H), 2.90 (m, 2H), 2.71 (m, 1H), 2.45 (m, 2H), 1.78 (m, 1H), 1.61 (m, 1H), 1.41 (m, 1H), 1.00 (m, 1H). TLC-MS ESI +ve ion 465.1 [M+H]$^+$.

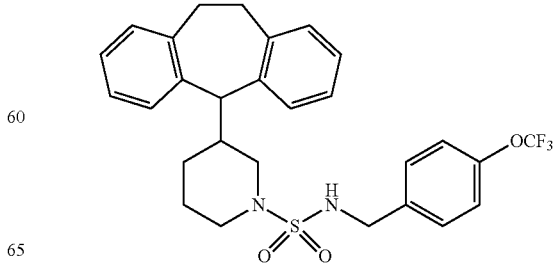

3-(10,11-dihydro-5H-dibenzo[a,d][7]annulen-5-yl)-N-(4-(trifluoromethoxy)benzyl)piperidine-1-sulfonamide was synthesized starting from tert-butyl ((3-(10,11-dihydro-5H-dibenzo[a,d][7]annulen-5-yl)piperidin-1-yl)sulfonyl)carbamate with 4-trifluoromethoxybenzylbromide in the alkylation step followed by Boc deprotection as above. 300 MHz $^1$H NMR in CDCl$_3$ 7.22-7.06 (overlapping m, 12H), 4.26 (m, 1H), 4.11 (m, 2H), 3.61 (m, 1H), 3.55-3.39 (overlapping m, 4H), 2.92 (m, 2H), 2.73 (m, 1H), 2.49 (overlapping m, 2H), 1.73 (m, 1H), 1.61 (m, 1H), 1.49 (m, 1H), 1.00 (m, 1H). TLC-MS ESI +ve ion 531.2 [M+H]$^+$, –ve ion 529.3 [M–H]$^-$.

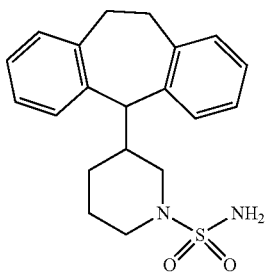 [SMILES: NS(=O)(=O)N1CCCC(C2c3ccccc3CCc3ccccc32)C1]

Deprotection of tert-butyl ((3-(10,11-dihydro-5H-dibenzo[a,d][7]annulen-5-yl)piperidin-1-yl)sulfonyl)carbamate with 20% trifluoroacetic acid in dichloromethane gives 3-(10,11-dihydro-5H-dibenzo[a,d][7]annulen-5-yl)piperidine-1-sulfonamide which was used as a starting material in the N-arylation route (Alcaraz et al) to example XX above. 3-(10,11-dihydro-5H-dibenzo[a,d][7]annulen-5-yl)piperidine-1-sulfonamide is a white solid: 300 MHz $^1$H NMR in CDCl$_3$ 7.20-7.08 (overlapping m, 8H), 4.33 (s, 2H), 3.59-3.43 (overlapping m, 4H), 3.33 (m, 1H), 2.99-2.86 (m, 2H), 2.72 (m, 1H), 2.59-4.44 (overlapping m, 2H), 1.78 (m, 1H), 1.63-1.44 (overlapping m, 2H), 1.06 (m TH).

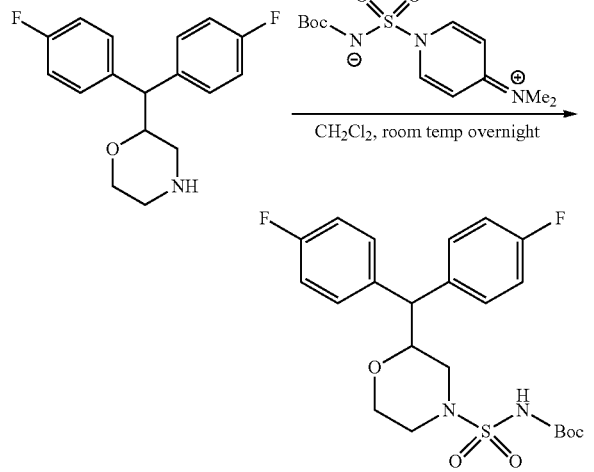

Using the method above, following Winum et al, Organic Letters, vol 3, pages 2241-2243, tert-butyl ((2-(bis(4-fluorophenyl)methyl)morpholino)sulfonyl)carbamate was synthesized and purified by flash chromatography eluting with 20% ethyl acetate-hexane. 300 MHz $^1$H NMR in CDCl$_3$ 7.25-6.96 (overlapping m, 8H), 6.88 (s, 1H), 4.20-4.11 (m, 1H), 3.96-3.92 (m, 2H), 3.70-3.50 (overlapping m, 3H), 3.10 (m, 1H), 2.75 (m, 1H). TLC-MS ESI, –ve ion 467.6 [M–H]$^-$.

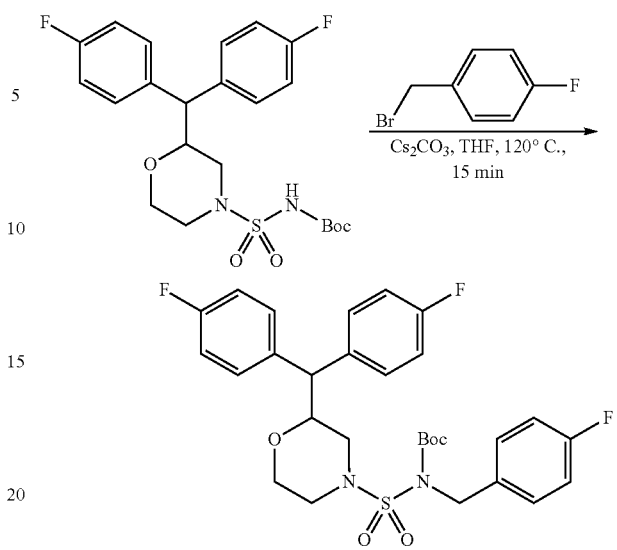

tert-butyl ((2-(bis(4-fluorophenyl)methyl)morpholino)sulfonyl)carbamate was alkylated using the conditions above to give tert-butyl ((2-(bis(4-fluorophenyl)methyl)morpholino)sulfonyl)(4-fluorobenzyl)carbamate. Purified by flash chromatography eluting with 5 to 10% ethyl acetate hexane. 300 MHz $^1$H NMR in CDCl$_3$ 7.27-7.14 (overlapping m, 6H), 7.01-6.92 (overlapping m, 6H), 4.75 (s, 1H), 4.11 (m, 1H), 3.84 (m, 2H), 3.55 (m, 1H), 3.35 (m, 2H), 2.93 (m, 1H), 2.58 (m, 1H), 1.45 (s, 9H).

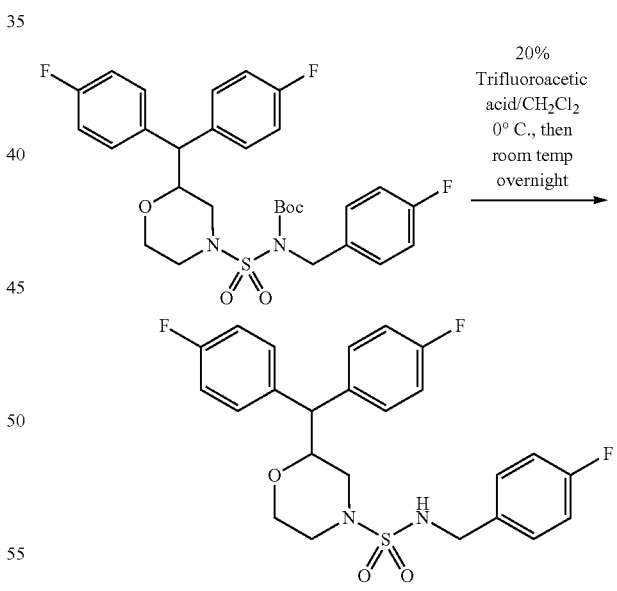

Deprotection of tert-butyl ((2-(bis(4-fluorophenyl)methyl)morpholino)sulfonyl)(4-fluorobenzyl)carbamate with 20% trifluoroacetic acid gives 2-(bis(4-fluorophenyl)methyl)-N-(4-fluorobenzyl)morpholine-4-sulfonamide. Clear oil foams under vacuumed. 300 MHz $^1$H NMR in CDCl$_3$ 7.15-6.96 (overlapping m, 12H), 4.33 (m, 1H), 4.14 (m, 2H), 4.04-3.88 (overlapping m, 3H), 3.55 (m, 1H), 3.42 (m, 1H), 3.27 (m, 1H), 2.78 (m, 1H), 2.48 (m, 1H). TLC-MS ESI, –ve ion 475.2 [M–H]$^-$.

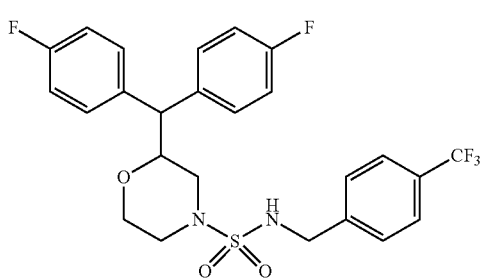 [SMILES: O=S(=O)(NCc1ccc(C(F)(F)F)cc1)N1CCOC(C(c2ccc(F)cc2)c2ccc(F)cc2)C1]

2-(bis(4-fluorophenyl)methyl)-N-(4-(trifluoromethyl) benzyl)morpholine-4-sulfonamide was synthesized by the above sequence and purified by flash chromatography eluting with 20 to 25% ethyl acetate-hexane. 300 MHz $^1$H NMR in CDCl$_3$ 7.76 (d, 2H), 7.38 (d, 2H), 7.26-6.96 (overlapping m, 8H), 4.63 (br s, 1H), 4.23 (br s, 2H), 3.97-3.87 (overlapping m, 3H), 3.50 (overlapping m, 2H), 3.25 (m, 1H), 2.82 (m, 1H), 2.50 (m, 1H). TLC-MS ESI, -ve ion 525.0 [M-H]$^-$.

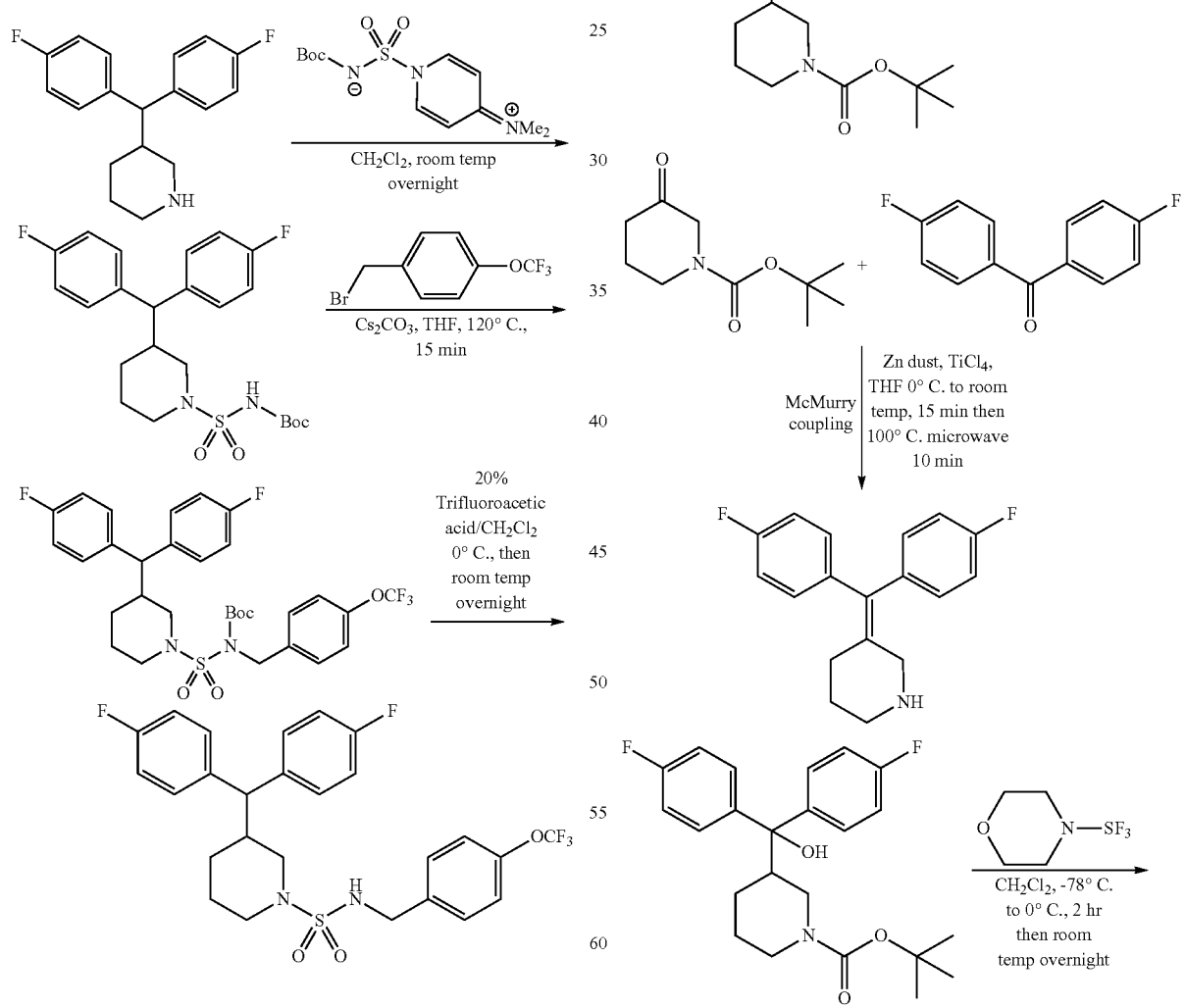

The above sulfamolyation, alkylation and deprotection route was used to prepare 3-(bis(4-fluorophenyl)methyl)-N-(4-(trifluoromethoxy)benzyl)piperidine-1-sulfonamide. 0.328 g (0.61 mmole), 61% yield over alkylation and deprotection steps as a white crystalline solid. 300 MHz $^1$H NMR in CDCl$_3$ 7.30-7.13 (overlapping in, 8H), 7.00-6.93 (overlapping in, 4H), 4.40 (br s, 1H), 4.13 (m, 2H), 3.60 (m, 1H), 3.46 (m, 2H), 2.68 (m, 1H), 3.31 (m, 2H), 1.72-1.54 (overlapping in, 3H), 0.95 (m, 1H). TLC-MS ESI, -ve ion 439.3 [M-H]$^-$.

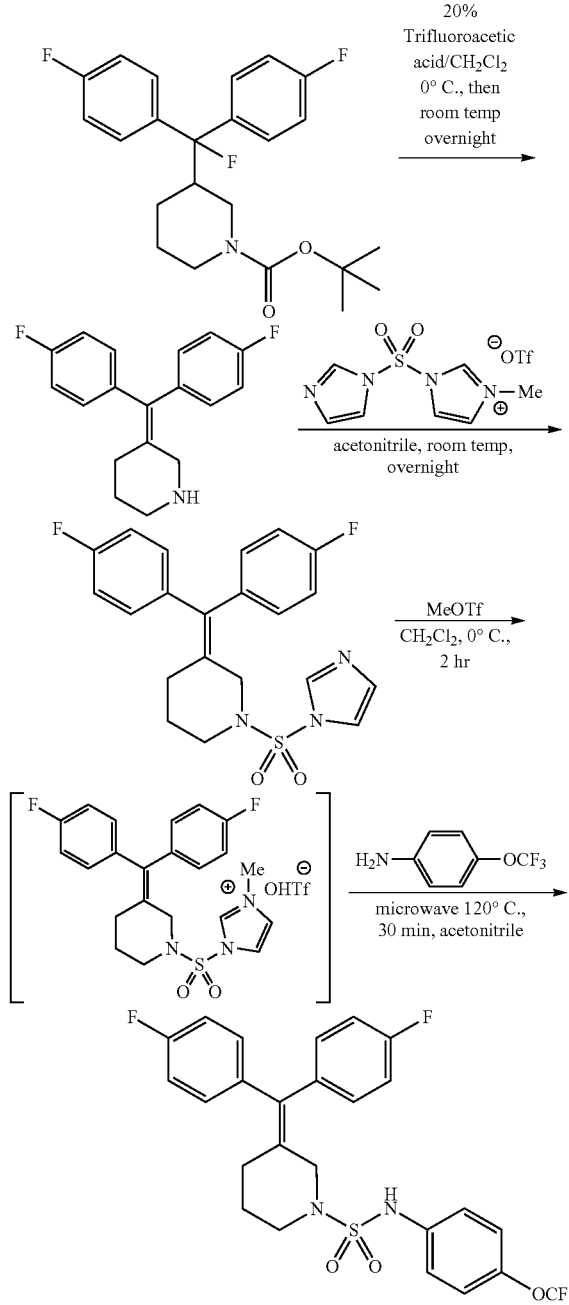

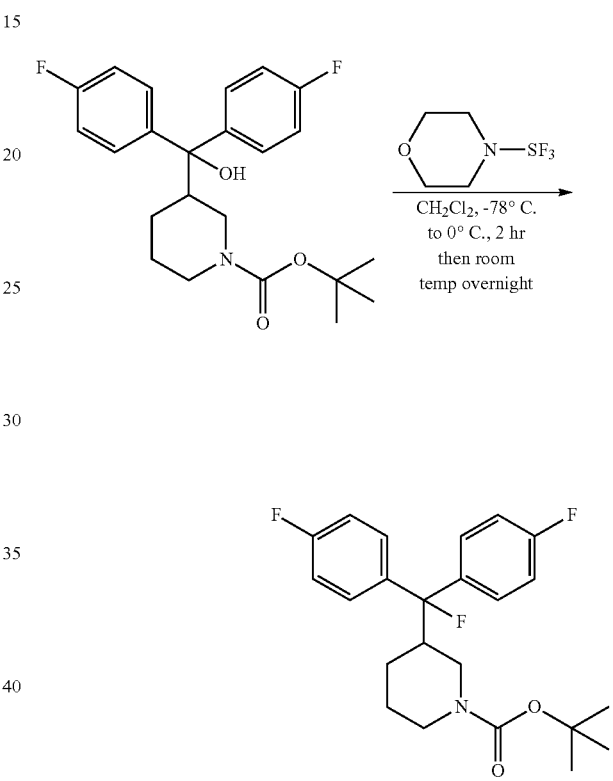

and 100 mL water. The aqueous was back extracted with 2×50 mL ethyl acetate and the combined ethyl acetate was wash with water once, then saturated brine. The ethyl acetate solution was dried over magnesium sulfate, filtered, then partially evaporated. White crystalline product precipitates and is collected by filtration and washed with 2×25 mL ethyl acetate, then dried in vacuo. Product, tert-butyl 3-(bis(4-fluorophenyl)(hydroxy)methyl)piperidine-1-carboxylate, is white crystalline solid, 11.27 g (28 mmole), 76% yield. 300 MHz $^1$H NMR in CDCl$_3$ 7.55-7.35 (overlapping m, 4H), 7.03-6.95 (overlapping m, 4H), 3.98 (m, 2H), 2.61 (m, 2H), 2.47 (m, 1H), 2.26 (m, 1H), 1.69 (m, 2H), 1.41 (s, 9H), 1.50-1.2 (overlapping m, 1H).

The diaryl moiety may be connected to the central ring via a double bond and compounds of this type were accessed as shown in the scheme above. Starting from 1-(tert-butyl) 3-ethyl piperidine-1,3-dicarboxylate: under argon a solution of 100 mL 0.8M (80 mmole, 2.2 equiv) of 4-phenylmagnesium bromide in THF was cooled to 0° C. in two-neck round bottomed flask equipped with a pressure equalizing addition funnel. A solution of 9.35 g (36.4 mmole, 1 equiv) of 1-(tert-butyl) 3-ethyl piperidine-1,3-dicarboxylate in 50 mL dry THF was added dropwise over 30 min with stirring at 0° C. The mixture was allowed to warm to room temperature and stirred overnight. The reaction was cooled to 0° C. and quenched by adding a solution of 5 g ammonium chloride in 20 mL water. The mixture was partially evaporated to remove THF, then partitioned between 200 mL ethyl acetate tert-butyl 3-(bis(4-fluorophenyl)(hydroxy)methyl)piperidine-1-carboxylate, 4.03 g (10 mmole, 1 equiv) was dissolved in 30 mL dry dichloromethane and cooled to −78° C., then morpho-DAST was added and the mixture stirred at −78° C. for 10 min. The mixture was warmed to 0° C. and stirred for approximately 30 min. The mixture was allowed to warm to room temperature and stirred overnight. The reaction was cooled to 0° C., then quenched by cautiously adding 20 mL sat. aq. sodium bicarbonate, and stirred for approximately 2 hr, after which time gas evolution stops. The mixture was diluted with 100 mL dichloromethane and washed with sodium bicarbonate, 0.1M hydrochloric acid and sodium bicarbonate. The organic was dried over magnesium sulfate, filtered and evaporated. The crude material was purified by flash chromatography to give a colorless oil which crystallizes on standing, 3.33 g (8.2 mmole), 82% yield of tert-butyl 3-(fluorobis(4-fluorophenyl)methyl)piperidine-1-carboxylate. 300 MHz $^1$H NMR in CDCl$_3$ 7.45-7.26 (overlapping m, 4H), 7.07-6.98 (overlapping m, 4H), 4.05 (m, 2H), 2.70-2.36 (overlapping m, 3H), 1.62-1.38 (m, 4H), 1.42 (s, 9H).

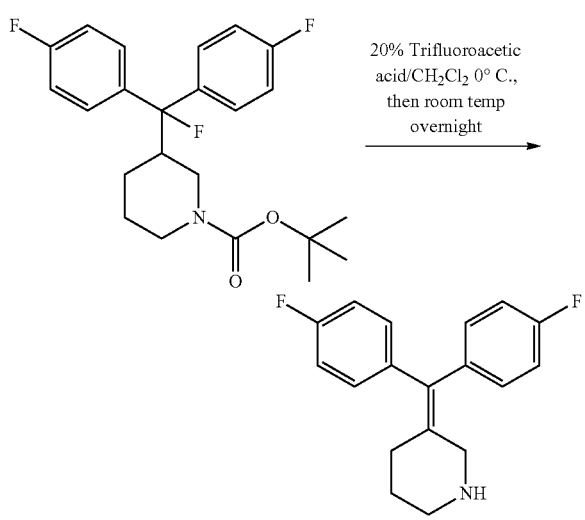

tert-butyl 3-(fluorobis(4-fluorophenyl)methyl)piperidine-1-carboxylate was dissolved in 40 mL dichloromethane and cooled to 0° C., the 10 ml trifluoroacetic acid was added. The mixture was allowed to warm to room temperature and stirred overnight. The reaction was evaporated to remove the majority of the solvent/TFA then the mixture was portioned between 100 mL ethyl acetate and 100 mL 1M sodium hydroxide. The aqueous was back extracted with 50 mL ethyl acetate and the combined ethyl acetate was washed with brine, then dried over sodium sulfate. Evaporation gives the product, 3-(bis(4-fluorophenyl)methylene)piperidine, as an oil. 300 MHz $^1$H NMR in CDCl$_3$ 7.09-6.93 (overlapping m, 8H), 3.43 (s, 2H), 2.96 (m, 2H), 2.35 (m, 2H), 1.69 (m, 2H). TLC-MS ESI, +ve ion 285.9 [M+H]$^+$, 327 [M+CH$_3$CN+H]$^+$.

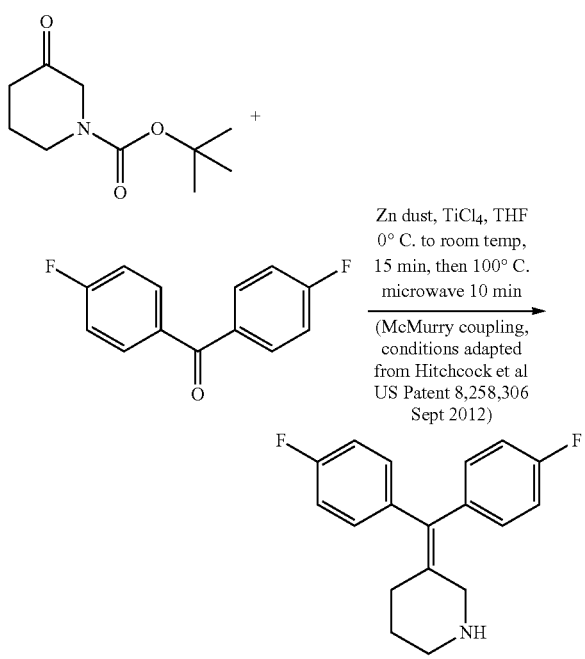

3-(bis(4-fluorophenyl)methylene)piperidine was also prepared via a McMurry coupling using conditions adapted from Hitchcock et al, U.S. Pat. No. 8,258,306. Thus a 35 mL microwave vessel was charged with 1.1 g (5 mmole, 1 equiv) of tert-butyl 3-oxopiperidine-1-carboxylate, 1.1 g (5.5 mmole, 1.1 equiv) of bis(4-fluorophenyl)methanone and 1.63 g (25 mmole, 5 equiv) of zinc dust. Dry THF, 20 mL, was added and the mixture stirred vigorously under argon. The mixture was cooled to 0° C. then 1.4 mL (2.4 g, 12.5 mmole, 2.5 equiv) of titanium tetrachloride was added and the mixture stirred at room temperature. The reaction was heated in CEM microwave for 10 min at 100° C. The reaction was quenched with hydrochloric acid, 150 mL, and diluted into 150 mL ethyl acetate. Organic was separated. Aqueous was made basic with KOH then extracted twice with 100 mL ethyl acetate. Combined organic and ethyl acetate layers were combined and dried over sodium sulfate. Filtration and evaporation gives 3-(bis(4-fluorophenyl)methylene)piperidine as a pale yellow oil which forms glassy solid on pumping in vacuo. 300 MHz $^1$H NMR in CDCl$_3$ 7.09-6.93 (overlapping m, 8H), 3.43 (s, 2H), 2.96 (m, 2H), 2.35 (m, 2H), 1.69 (m, 2H). This material was used directly in the next step.

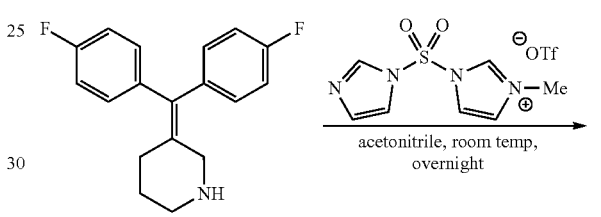

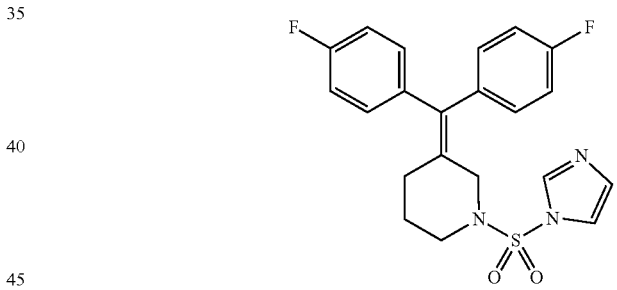

2.0 g (6.6 mmole, 1 equiv) of 3-(bis(4-fluorophenyl)methylene)piperidine was dissolved in 30 mL dry acetonitrile and 3.6 g (9.9 mmole, 1.5 equiv) of freshly prepared 3-(Imidazole-1-sulfonyl)-1-methyl-3H-imidazol-1-ium triflate was added as a solid in one portion with stirring. The pale yellow solution was stirred at room temperature overnight. Solvent was evaporated to give an orange-yellow solid which was purified by flash chromatography eluting with 30 to 50% ethyl acetate hexanes to give the product, 1-((1H-imidazol-1-yl)sulfonyl)-3-(bis(4-fluorophenyl)methylene)piperidine, as an off-white solid. 300 MHz $^1$H NMR in CDCl$_3$ 7.79 (s, 1H), 7.17-6.95 (overlapping m, 10H), 3.88 (s, 1H), 3.38 (m, 2H), 2.26 (m, 2H), 1.70 (m, 2H). TLC-MS ESI, +ve ion 416.2 [M+H]$^+$, 457.2 [M+CH$_3$CN+H]$^+$.

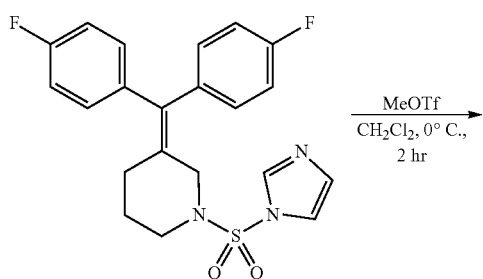

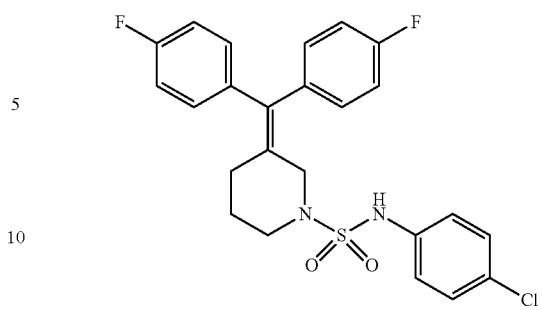

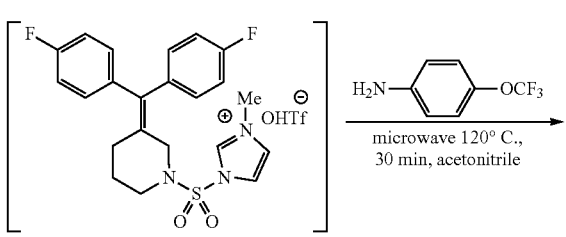

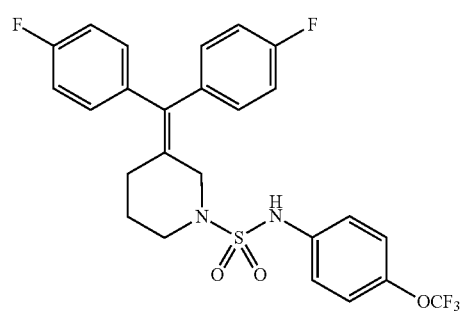

0.87 g (2 mmole, 1 equiv) of 1-((1H-imidazol-1-yl)sulfonyl)-3-(bis(4-fluorophenyl)methylene)piperidine was dissolved in 10 mL dry dichloromethane and the solution was cooled to 0° C. Methyl trifluoromethanesulfonate, 0.24 mL (0.361, 2.2 mmole, 1.1 equiv) was added dropwise with stirring. A dense white precipitate forms immediately. Slurry is stirred at 0° C. for 2 hours. Solvent is evaporated and residue pumped on for 30 min. Solid is dissolved in 15 mL dry acetonitrile and transferred to a microwave vial. 0.3 mL (0.4 g, 2.2 mmole, 1.1 equiv) of 4-trifluoromethoxyaniline is added and the solution stirred and heated at 120° C. in CEM microwave for 30 min. Reaction is diluted in 100 mL ethyl acetate and washed with 0.1M hydrochloric acid then sat. aq. sodium bicarbonate solution. Ethyl acetate solution is dried over magnesium sulfate, then filtered and evaporated to give crude product which is purified by flash chromatography eluting with 15 to 30% ethyl acetate-hexanes. Product crystallizes on standing and is recrystallized from 10 mL 5% ethyl acetate hexane to give 3-(bis(4-fluorophenyl)methylene)-N-(4-(trifluoromethoxy)phenyl)piperidine-1-sulfonamide as a white solid, 0.842 g (1.6 mmole), 80% yield. 300 MHz $^1$H NMR in CDCl$_3$ 7.19-6.92 (overlapping m, 12H), 6.49 (s, 1H), 3.86 (s, 2H), 4.43 (m, 2H), 2.29 (m, 2H), 1.70 (m, 2H). TLC-MS ESI, −ve ion 523.1 [M−H]$^-$.

3-(bis(4-fluorophenyl)methylene)-N-(4-chlorophenyl)piperidine-1-sulfonamide was synthesized from 1-((1H-imidazol-1-yl)sulfonyl)-3-(bis(4-fluorophenyl)methylene)piperidine by the method above using 4-chloroaniline in coupling step. 300 MHz $^1$H NMR in CDCl$_3$ 7.27 (m, 2H), 7.02-6.93 (overlapping m, 10H), 6.48 (s, 1H), 3.85 (s, 2H), 3.40 (m, 2H), 2.28 (m, 2H), 1.69 (m, 2H). TLC-MS ESI, −ve ion 473.1, 475.1 [M−H]$^-$.

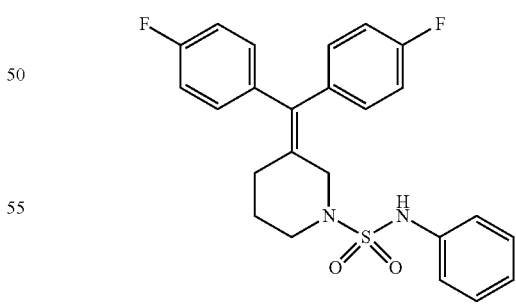

3-(bis(4-fluorophenyl)methylene)-N-(4-(trifluoromethyl)phenyl)piperidine-1-sulfonamide was synthesized from 1-((1H-imidazol-1-yl)sulfonyl)-3-(bis(4-fluorophenyl)methylene)piperidine by the method above using 4-trifluoromethylaniline in coupling step. 300 MHz $^1$H NMR in CDCl$_3$ 7.56 (d, 2H), 7.11 (d, 2H), 6.97-6.91 (overlapping m, 8H), 6.74 (s, 1H), 3.89 (s, 2H), 3.45 (m, 2H), 2.30 (m, 2H), 1.72 (m, 2H). TLC-MS ESI, −ve ion 507.2 [M−H]$^-$.

3-(bis(4-fluorophenyl)methylene)-N-phenylpiperidine-1-sulfonamide was synthesized from 1-((1H-imidazol-1-yl)sulfonyl)-3-(bis(4-fluorophenyl)methylene)piperidine by the method above using aniline in coupling step. 300 MHz $^1$H NMR in CDCl$_3$ 7.39-6.91 (overlapping m, 13H), 6.52 (s, 1H), 3.86 (s, 2H), 3.41 (m, 2H), 2.27 (m, 2H), 1.68 (m, 2H). TLC-MS ESI, +ve ion 441.1 [M+H]$^+$.

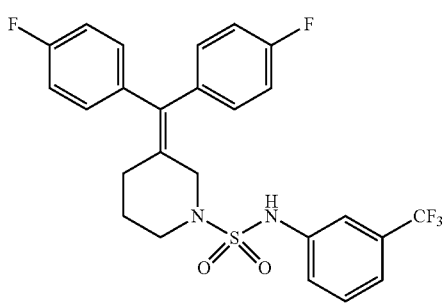 [SMILES: O=S(=O)(Nc1cccc(C(F)(F)F)c1)N1CCCC(=C(c2ccc(F)cc2)c2ccc(F)cc2)C1]

3-(bis(4-fluorophenyl)methylene)-N-(3-(trifluoromethyl)phenyl)piperidine-1-sulfonamide was synthesized from 1-((1H-imidazol-1-yl)sulfonyl)-3-(bis(4-fluorophenyl)methylene)piperidine by the method above using 3-trifluoromethylaniline in coupling step. 300 MHz $^1$H NMR in CDCl$_3$ 7.44-7.34 (overlapping m, 3H), 7.19 (m, 1H) 6.98-6.90 (overlapping m, 8H), 6.63 (s, 1H), 3.87 (s, 2H), 3.45 (m, 2H), 2.30 (m, 2H), 1.72 (m, 2H). TLC-MS ESI, –ve ion 507.2 [M–H]$^-$.

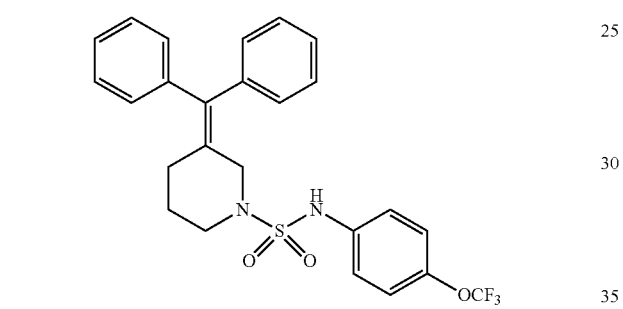

3-(diphenylmethylene)-N-(4-(trifluoromethoxy)phenyl)piperidine-1-sulfonamide. Using the methods above was synthesized from 1-((1H-imidazol-1-yl)sulfonyl)-3-(diphenylmethylene)piperidine. 300 MHz $^1$H NMR in CDCl$_3$ 7.28-6.97 (overlapping m, 14H), 6.59 (s, 1H), 3.88 (s, 2H), 3.42 (m, 2H), 2.31 (m, 2H), 1.69 (m, 2H). TLC-MS ESI, +ve ion 489.2 [M+H]$^+$.

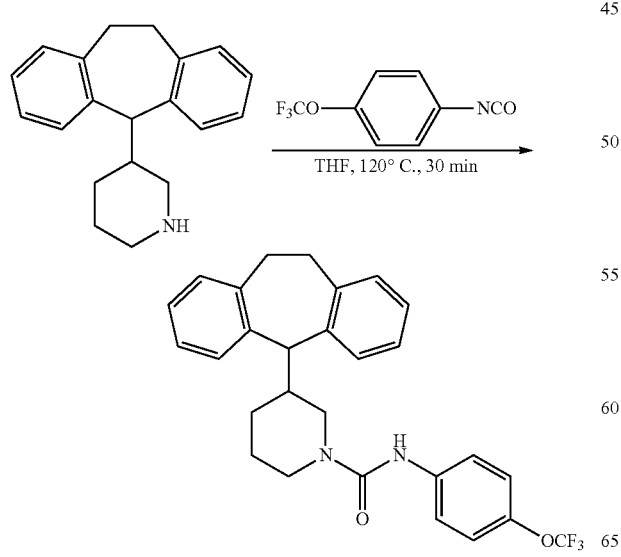

3-(10,11-dihydro-5H-dibenzo[a,d][7]annulen-5-yl)-N-(4-(trifluoromethoxy)phenyl)piperidine-1-carboxamide. To a suspension of 0.277 g (1 mmole, 1 equiv) in 10 mL THF was added 0.164 mL (0.223 g, 1.1 mmole, 1.1 equiv) of 4-trfluoromethoxyphenylisocyanate. The mixture was stirred and heated at 120° C. for 30 min in a CEM microwave. Reaction was diluted into 100 mL ethyl acetate and washed with 1M hydrochloric acid, sodium bicarbonate solution and dried over magnesium sulfate. Solution was filtered and evaporated to give crude product which was purified by flash chromatography eluting with 20% ethyl acetate-hexane. 3-(10,11-dihydro-5H-dibenzo[a,d][7]annulen-5-yl)-N-(4-(trifluoromethoxy)phenyl)piperidine-1-carboxamide is clear oil which gives glassy foam on pumping: 300 MHz $^1$H NMR in CDCl$_3$ 7.26-7.08 (overlapping m, 12H), 6.05 (s, 1H), 3.83 (m, 1H), 3.59-3.41 (overlapping m, 4H), 3.08-2.88 (overlapping m, 3H), 2.73 (m, 1H), 2.49-2.39 (m, 1H), 1.72-1.61 (overlapping m, 2H), 1.47 (m, 1H), 1.25 (m, 1H). TLC-MS ESI, +ve ion 481.2 [M+H]$^+$, –ve ion 479.3 [M–H]$^-$.

Synthetic Route to Examples 114 and 115

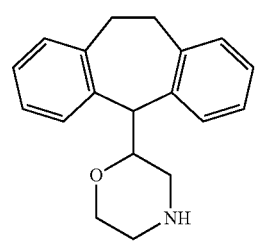

-continued

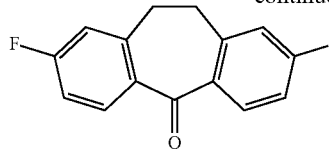

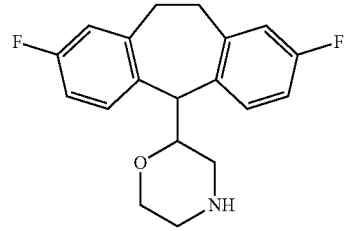 [SMILES: Fc1ccc2c(c1)CCc1cc(F)ccc1C2C1CNCCO1]

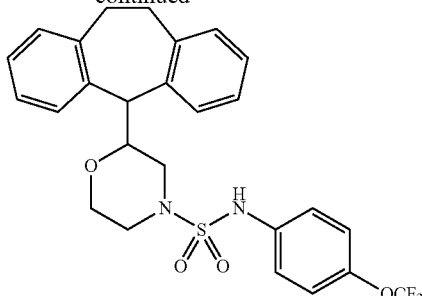

-continued

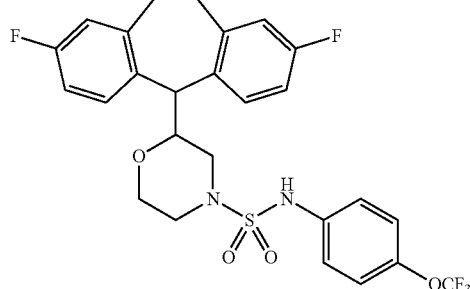

Compounds wherein the diarylmethylcycloamine is, for example, 2-(10,11-dihydro-5H-dibenzo[a,d][7]annulen-5-yl)morpholine may be synthesized the route shown above. Thus dibenzosuberone or related analogs are reduced to the corresponding secondary alcohol using sodium borohydride, then converted to the benzylic bromide using standard conditions, for example treatment with phosphorus tribromide (shown above), P(O)Br$_3$ or the like reagents. The bromide is coupled with vinyl magnesium bromide using conditions adapted from Lopez-Perez et al, Organic Letters, vol 11, pages 5514-5517 to give 5-vinyl-10,11-dihydro-5H-dibenzo[a,d][7]annulene. The double bond is epoxidized under standard conditions, for example with mCPBA, to give 2-(10,11-dihydro-5H-dibenzo[a,d][7]annulen-5-yl)oxirane. 2-(10,11-dihydro-5H-dibenzo[a,d][7]annulen-5-yl)oxirane is a known compound and may also be accessed by the routes described in Hendricks et al, WO 2016/145103 and Hendricks et al US 2015/0072982. Conditions for conversion of the epoxide to the morpholine are given in Take et al, WO 2002/000631 and involve reaction with 2-aminoethyl sulfate in the presence of a base such as sodium hydroxide in isopropanol with heating. These conditions may also be adapted to microwave heating to reduce reaction times. The above synthetic approach may also be adapted to substituted analogs such as 2-(2,8-difluoro-10,11-dihydro-5H-dibenzo[a,d][7]annulen-5-yl)morpholine by using the appropriately substituted dibenzosuberone starting material, for example 2,8-difluoro-10,11-dihydro-5H-dibenzo[a,d][7]annulen-5-one.

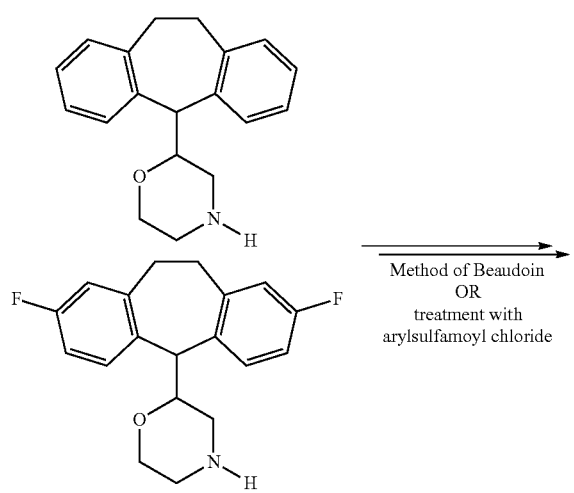

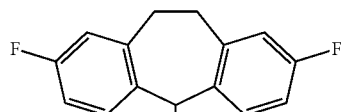

The 2-dibenzoannulenyl morpholines are converted to final products by the method of Beaudoin et al, J. Org. Chem. 2003, vol 68, pages 115-119, or by reaction with the appropriate arylsulfamoyl chloride.

Colony Formation Assay

Protocol for clonogenic assay follows Sangodkar et al., J Clin Invest 2012; 122:2637-51.

Cell culture and staining: For both A549luc and H1650 cells, 500 cells are seeded into each well of a 6-well plate and allowed to attach for 24 hours before drug treatment. The following day, cells are treated with either the appropriate dose of drug or an equivalent volume of DMSO (two replicates were treated for each condition). For each condition, depleted media is replaced with fresh media containing the equivalent drug dose four days after initial treatment. Cells are harvested either 7 (A549luc) or 8 (H1650) days after initial treatment. Briefly, medium is aspirated from each well and the cells are washed twice with ice-cold PBS, then plates are allowed to dry at room temperature for 4 hours. Cells are fixed for one hour in a fixing solution consisting of 10% methanol and 10% glacial acetic acid in distilled water, then stained overnight in 1% (w/v) crystal violet dissolved in methanol. The next day, staining solution is aspirated from the wells and plates are washed gently with distilled water to remove excess stain before colony counting. Colonies are imaged on a ChemiDoc XRS+(Bio-Rad) and images are exported as 8-bit TIFF files. Colonies are counted using the Colony Counter plugin in ImageJ, with colony size defined as between 4 and 400 square pixels, and minimum circularity set at 0.6. Duplicate wells are averaged to obtain a single value for each condition. Results (number of colonies) for A549luc cells and results (number of colonies) for H1650 cells may be analyzed separately.

Example compounds 1a, 2, 4 and 6 were assayed in an A549 cell growth inhibition assay as follows. A549 cells were cultured in DMEM medium with supplement of 10% FBS and 1% Pen-strep. Assay conditions: to perform the proliferation assay, A549 cells were seeded at 5000 cells/90 µl growth medium/well on 96-well black clear-bottom tissue culture plate. Cells were incubated at 37° C. and 5% CO$_2$ overnight to allow them to recover and reattach. Next day cells were treated with tested compounds for 72 hours. After treatment, cell proliferation was measured by Fluorescent quantitation of alamarBlue reagent. The alamarBlue assay incorporates a fluorometric/colorimetric growth indicator based on detection of metabolic activity. Specifically, resazurin, the active ingredient of alamarBlue reagent, is blue in color and virtually non-fluorescent. Upon entering cells, resazurin is reduced to resorufin, a compound that is red in color and highly fluorescent. Continued cell growth maintains a reduced environment, therefore increasing the overall fluorescence and color of the media surrounding cells. Our experiment has shown that the fluorescence intensity of alamarBlue reagent was directly proportional to cell number. To perform the alamarBlue assay, 10 µl of alamarBlue reagent was added to each well and the plate was incubated at 37° C. for an additional 1-4 hours. Fluorescence intensity was measured at an excitation of 530 nm and an emission of 590 nm using a BioTek Synergy™ 2 microplate reader.

Data analysis. Cell proliferation assays in triplicate were performed at each concentration. The fluorescent intensity data were analyzed using the computer software, Graphpad Prism. In the absence of the compound, the fluorescent intensity ($F_t$) in each data set was defined as 100%. In the absence of cells, the fluorescent intensity ($F_b$) in each data set was defined as 0%. The percent cell in the presence of each compound was calculated according to the following equation: % cell=$(F-F_b)/(F_t-F_b)$, where F=the fluorescent intensity in the presence of the compound, $F_b$=the fluorescent intensity in the absence of cells, and $F_t$=the fluorescent intensity in the absence of the compound. The values of % cell versus a series of compound concentrations were then plotted using non-linear regression analysis of Sigmoidal dose-response curve generated with the equation Y=B+(T-B)/1+10$^{(LogEC50-X) \times Hill\ Slope}$ where Y=percent cell, B=minimum percent cell, T=maximum percent cell, X=logarithm of compound and Hill Slope=slope factor or Hill coefficient. The IC50 value was determined by the concentration causing a half-maximal percent activity.

Compounds were also assayed in an A172 cell growth inhibition assay as follows. A172 glioblastoma cells were cultured in Dulbecco's modified Eagle's medium (DMEM) supplemented with 10% fetal bovine serum and 1% Penicillin-streptomycin. Incubation was performed at 37° C. and 5% $CO_2$.

A172 cells were seeded at 3000-3500 cells/90 ul growth medium per well on 96-well tissue culture plates. Cells were incubated overnight to allow them to recover and reattach. Next day cells were treated with tested compounds and incubated for 48-72 hours.

Cell Proliferation assays in triplicate were performed at each concentration. Compounds test range was 1-30 µM (0, 5, 10, 15, 20, 25, and 30). The compounds were dissolved in DMSO. A series of dilutions were made in 1% DMSO in growth medium so that the final concentration of DMSO is 0.1% in all of treatments.

After treatment, cells were allowed to equilibrate at room temperature for ½ to one hour. Cell proliferation was measured by Luminescence quantification using Promega CellTiter-Glo Luminescent Cell Viability Assay. To perform the assay, 100 µl of Celltiter-Glo substrate was added to each well, plates were shake for 2 minutes and allowed to equilibrate for 10 minutes at room temperature. Luminescence intensity was measured using the Spectramax i3x plate reader.

The Luminescence intensity data were analyzed using the computer software Graphpad Prism. In the absence of the compound, the luminescence intensity ($L_t$) in each data set was defined as 100% cell viability. The percent cell in the presence of each compound was calculated according to the following equation: % Cell=$L/L_t$, where L=the luminescence intensity in the presence of the compound.

The values of % cell versus a series of compound concentrations (0, 5, 10, 15, 20, 25, and 30 µM) were then plotted using nonlinear regression analysis of Sigmoidal dose-response curve. $IC_{50}$ values were determined by the concentration causing a half-maximal percent activity.

$IC_{50}$ for example compounds, determined by the methods above are given in the table below.

TABLE 2

| Example | $IC_{50}$ for A549 or A172 cell growth (µM) | Note |
|---|---|---|
| 1a | 8.27 (A549), 12.1 (A172) | |
| 2 | 22.86 (A549), 23 (A172) | |
| 4 | 9.61 (A549), 17.1 (A172) | |
| 6 | 12.81 (A549) | |
| 19 | 18.2 (A172) | |
| 22 | 26 (A172) | |
| 25 | 19.4 (A172) | |
| 26 | 28.2 (A172) | |
| 37 | 11.03 (A172) | |
| 40 | 15.8 (A172) | |
| 42 | 51 (A172) | |
| 71 | 13 (A172) | |
| 93 | 45 (A172) | |
| 94 | 23.2 (A172) | |
| 96 | 16.1 (A172) | |
| 97 | 27.2 (A172) | |
| 98 | 10.44 (A172) | |
| 99 | 25.3 (A172) | |
| 100 | 16.2 (A172) | |
| 101 | 22.1 (A172) | |
| 102 | 20.6 (A172) | |
| 103 | 10.35 (A172) | |
| 104 | 14.79 (A172) | |
| 105 | 20.3 (A172) | |
| 106 | 12.8 (A172) | |
| 108 | 16.1 (A172) | |
| 109 | 19.2 (A172) | |
| 110 | 25 (A172) | |
| 111 | 30 (A172) | |
| 112 | 24 (A172) | |
| 113 | 10.8 (A172) | |
| Doxorubicin | 0.34 (A549) | Positive control |

In Vivo Cancer Model

To assess the in vivo effects of the compounds, subcutaneous xenograft of lung cancer cell line H441 are generated. Cells (5×10$^6$) are injected into the right flank of 6- to 8-week-old male BALB/c nu/nu mice (Charles River, Wilmington, MA). Tumor volume is assessed twice a week by caliper measurement. Mice are randomized to treatment groups based on initial tumor volume average of 100 mm$^3$~ per group. Mice are dosed by oral gavage with 15 mg/kg of a compound of formula I QD, 15 mg/kg of a compound of formula I BID, or 50 mg/kg of a compound of formula I QD. Mouse tumors are measured twice a week for the duration of the study. Mouse body weights are recorded weekly and percentage of mice body weights during treatment are calculated as: weight at each time point/initial weight ×100. Animals are observed for signs of toxicity (mucous diarrhea, abdominal stiffness and weight loss) and adverse signs are observed. Mice undergo treatment for 30 days and are sacrificed 2 hours after the last dose. Tumors are then excised and cut for both formalin-fixation and snap frozen in liquid nitrogen. Inhibition of tumor(T) growth versus vehicle control(C) is determined.

In Vivo COPD Model.

To assess the effects of the compounds in a smoke induced COPD model the methods used in Doherty et al, Am J Respir Crit Care Med Vol, 2019, "Protein Phosphatase 2A Reduces Cigarette Smoke-induced Cathepsin S and Loss of Lung" may be used.

To assess the effects of the compounds in a homocysteine induced model of neurodegenerative disease the methods of Wei et al, Neurotherapeutics, https://doi.org/10.1007/si3311-020-00841-6, "Direct Activation of Protein Phosphatase 2A (PP2A) by Tricyclic Sulfonamides Ameliorates Alzheimer's Disease Pathogenesis in Cell and Animal Models" maybe used.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

I claim:

1. A compound of formula I:

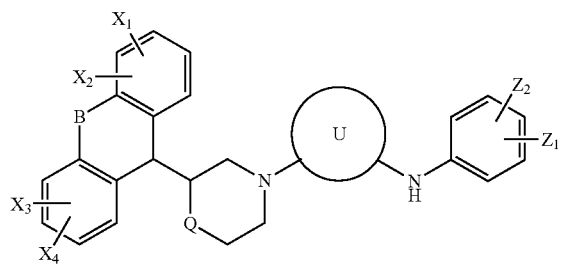

or a pharmaceutically acceptable salt thereof, wherein:

B is absent or is selected from a direct bond, O, S, —$CH_2CH_2$— or —CH=CH—;

Q is selected from —$(CH_2)_n$—, —O—, —S—, or —$SO_2$—$NR^5$;

n is 0, 1, or 2;

U is a group selected from:

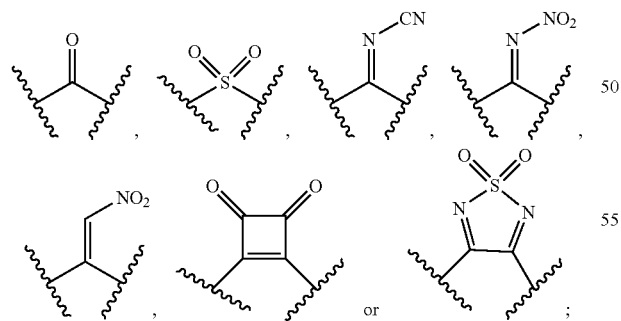

$X^1$, $X^2$, $X^3$, and $X^4$ are independently selected in each instance from hydrogen, halogen, nitro, cyano, ($C_1$-$C_6$)alkyl optionally substituted with —OH, ($C_1$-$C_6$) haloalkyl, ($C_1$-$C_6$)haloalkoxy, ($C_1$-$C_6$) haloalkylthio, —$NR^1R^2$, —$OR^1$, —$C(O)R^1$, —$OC(O)R^1$, —$C(O)NR^1R^2$, —C(O) $OR^1$, —$SR^1$, —$SO^2R^1$, or —$SO^2NR^1R^2$;

$R^1$ and $R^2$ are independently selected in each instance from hydrogen or ($C_1$-$C_6$)alkyl;

$Z^1$ and $Z^2$ are independently selected in each instance from hydrogen, halogen, nitro, cyano, azido, ($C_1$-$C_6$) alkyl, ($C_1$-$C_6$) haloalkyl, ($C_1$-$C_6$)haloalkoxy, ($C_1$-$C_6$) haloalkylthio, —$NR^3R^4$, —$NR^3C(O)R^4$, —$NR^3C(O) OR^5$, —$OR^3$, —$C(O)R^3$, —$OC(O)R^3$, —$C(O) NR^3R^4$, —C(O) $OR^3$, —$SR^3$, —$SO^2R^3$, or —$SO^2NR^3R^4$;

$R^3$, $R^4$ and $R^5$ are independently selected from lower alkyl;

$R^3$ and $R^4$ may be joined to form a ring;

$R^5$ is selected from optionally substituted lower alkyl, lower cycloalkyl, or acyl.

2. A compound, selected from:

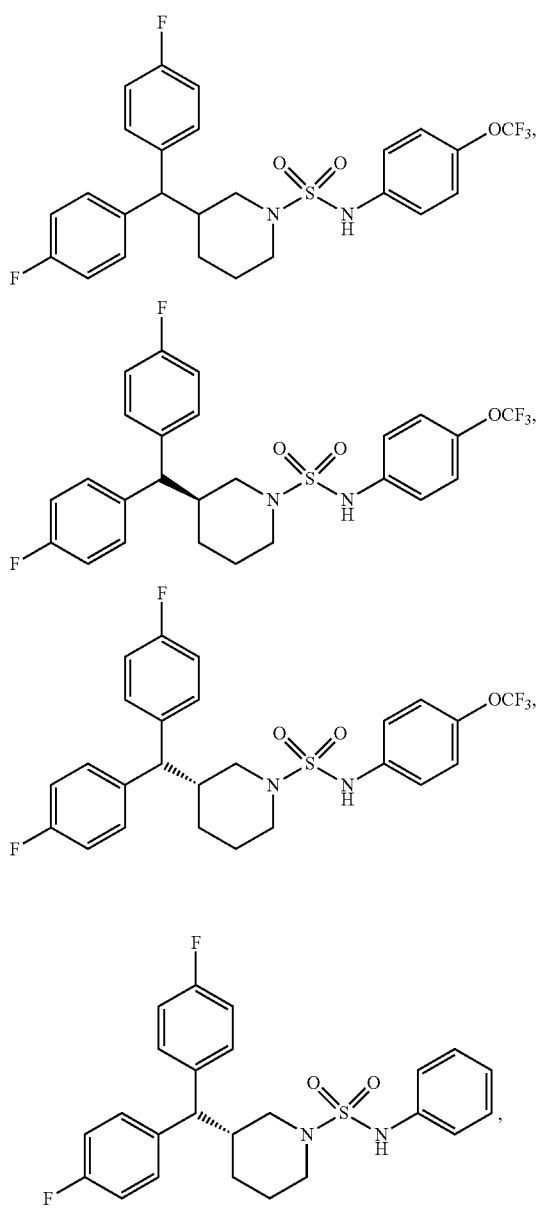

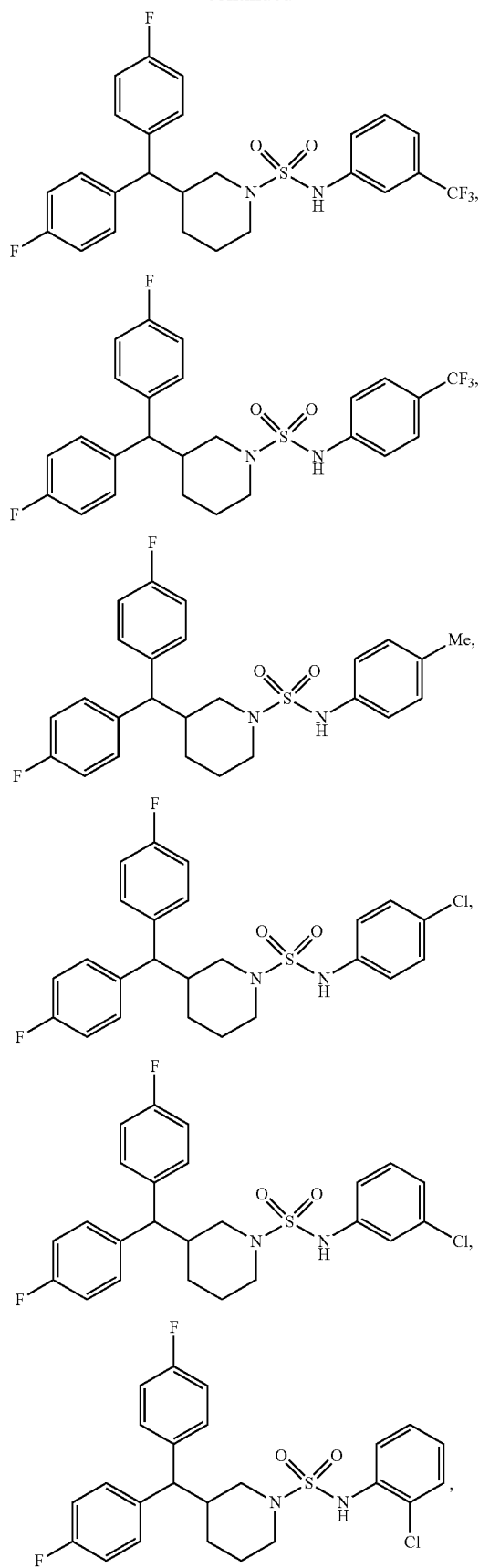
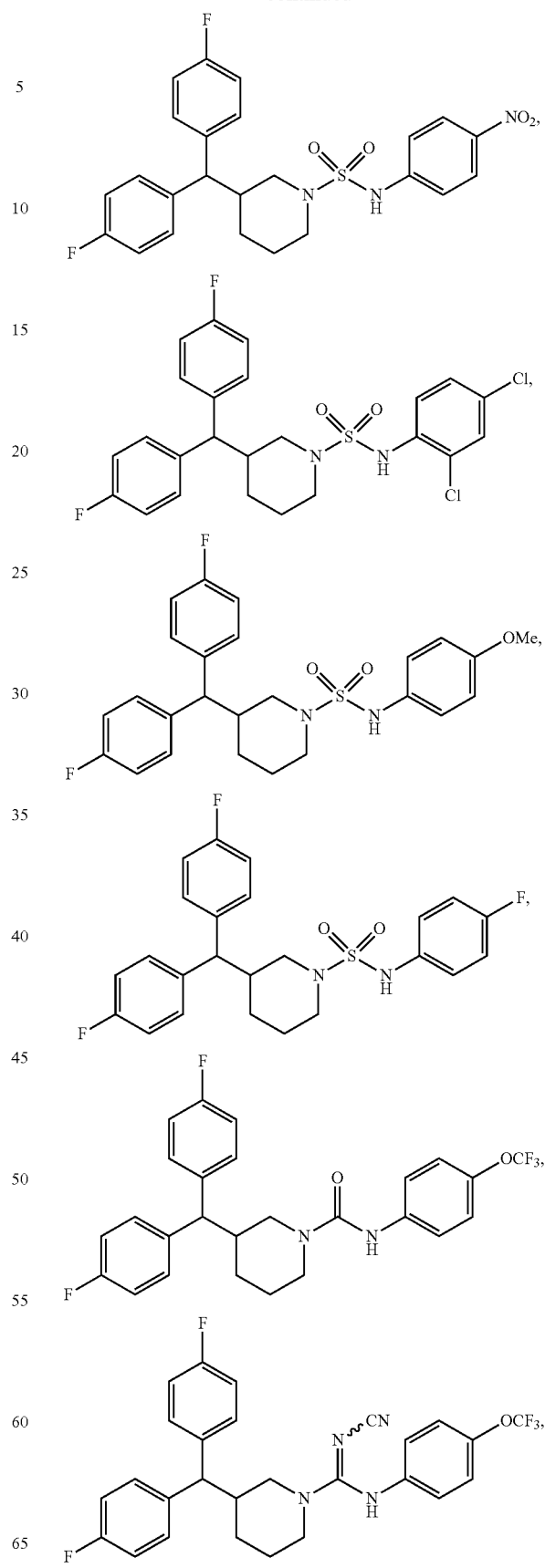

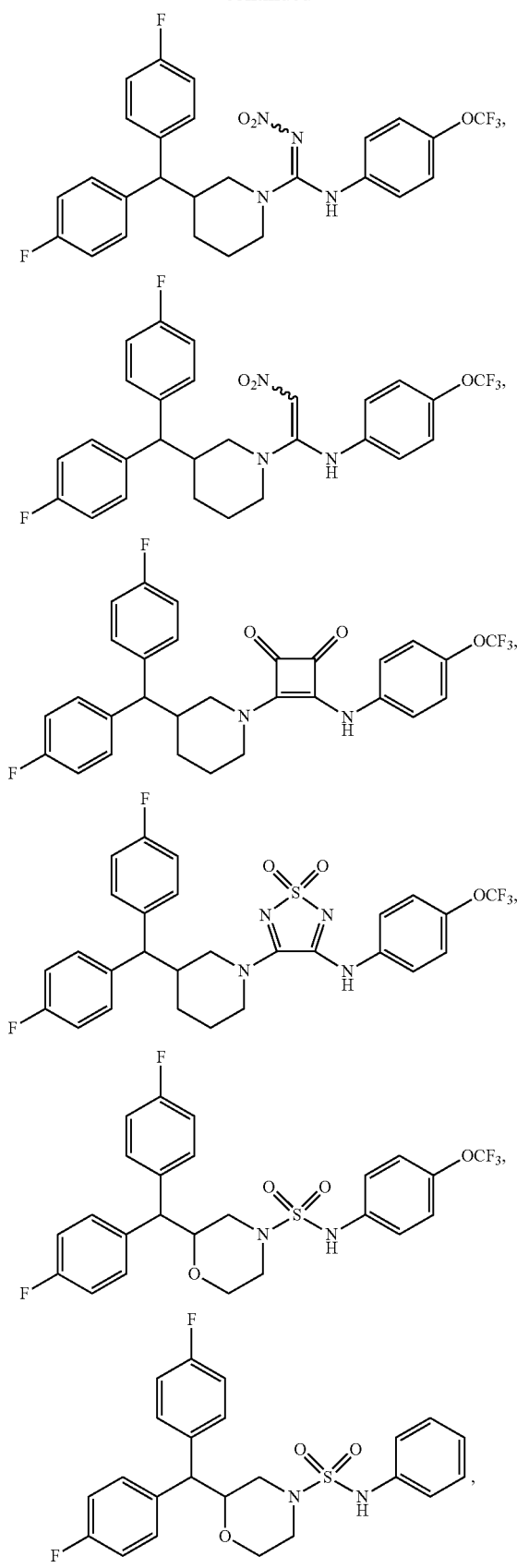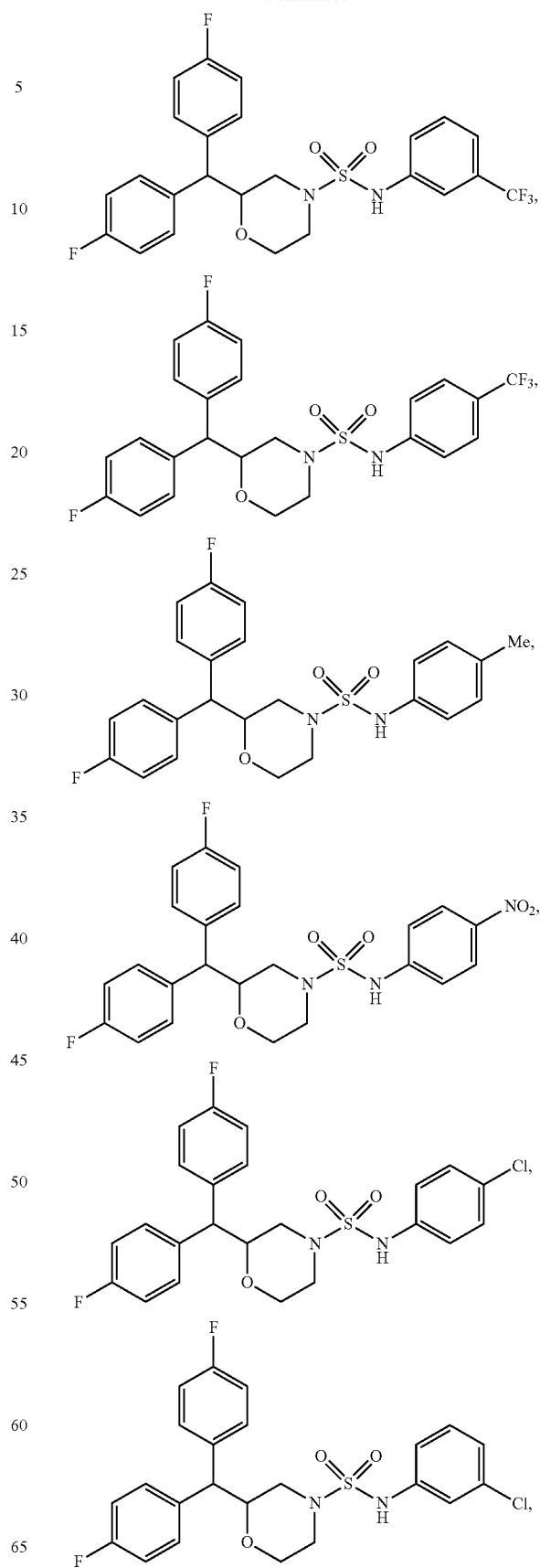

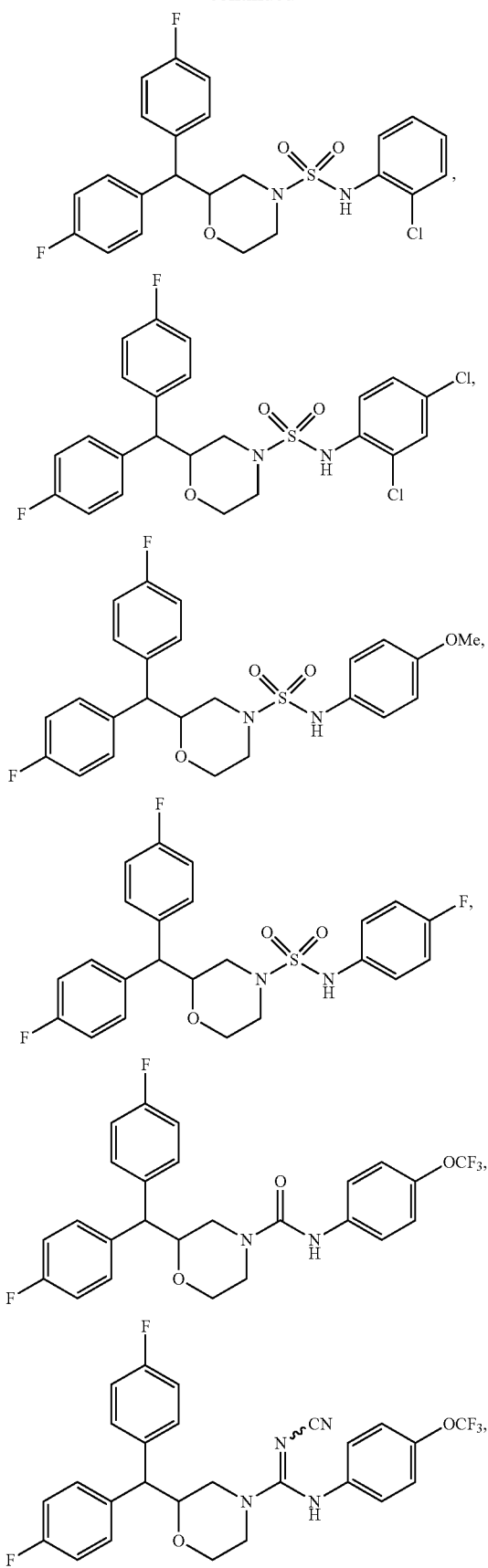

149
-continued
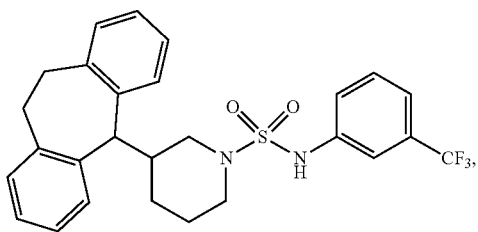
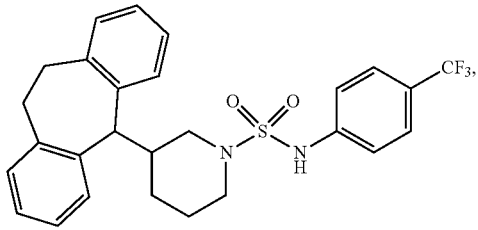
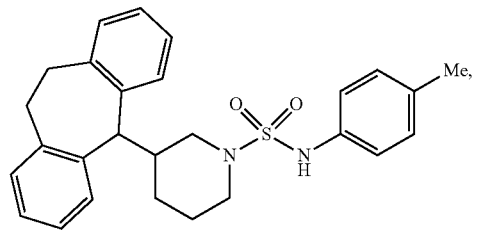
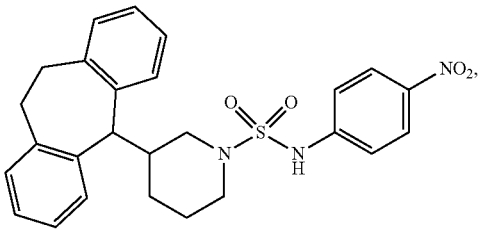
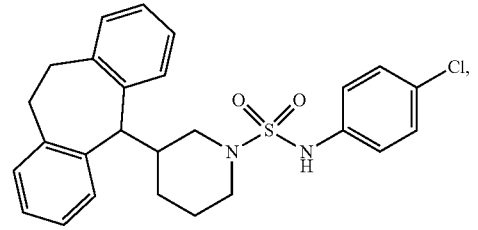
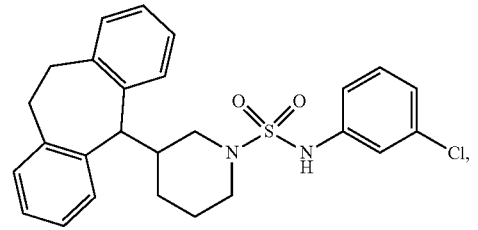
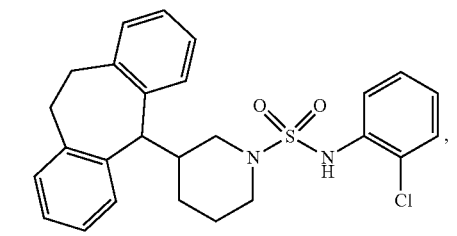
150
-continued
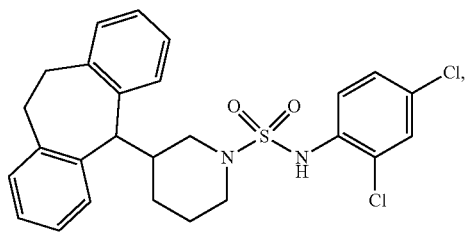
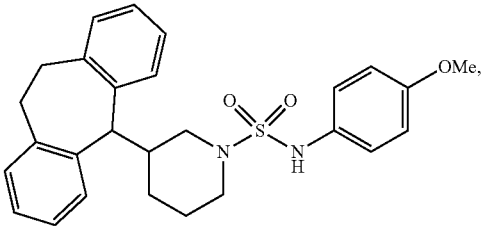
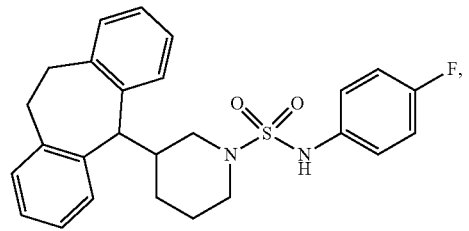
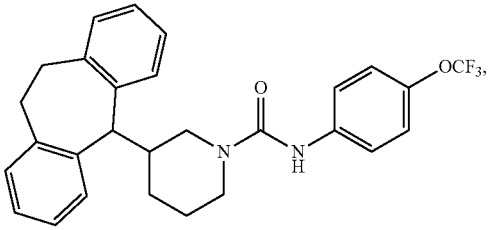
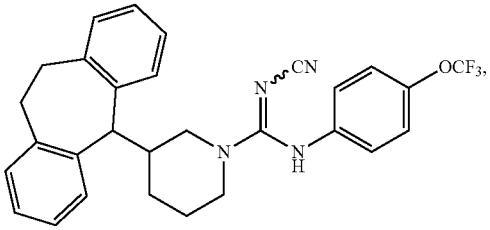
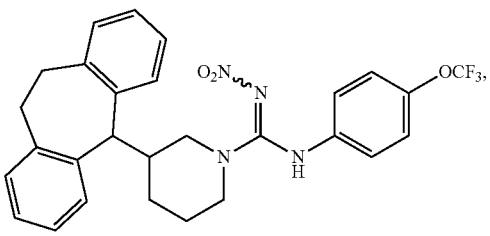
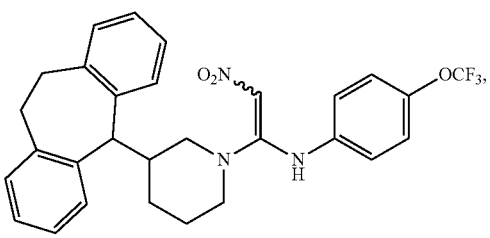

151
-continued
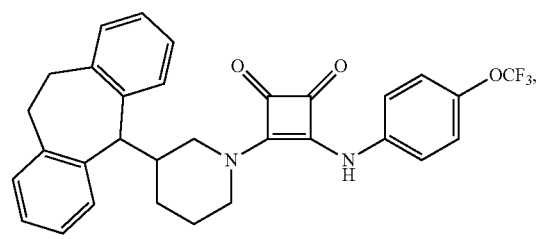
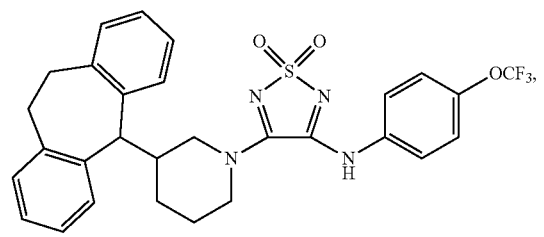
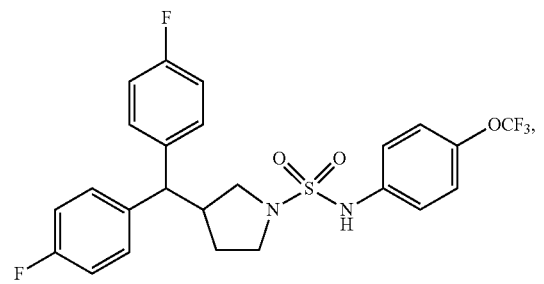
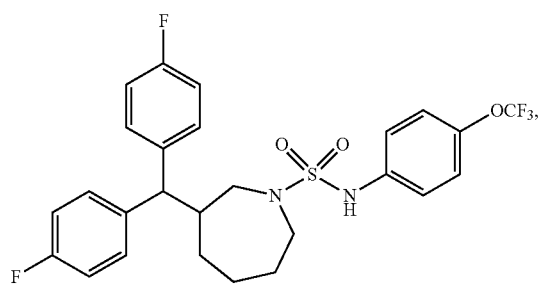
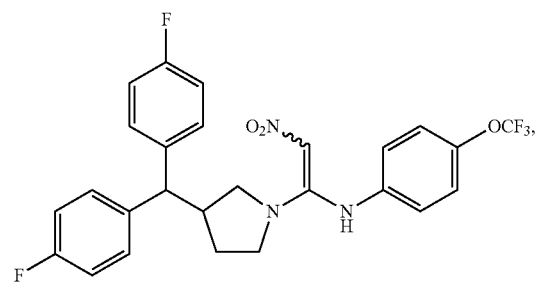
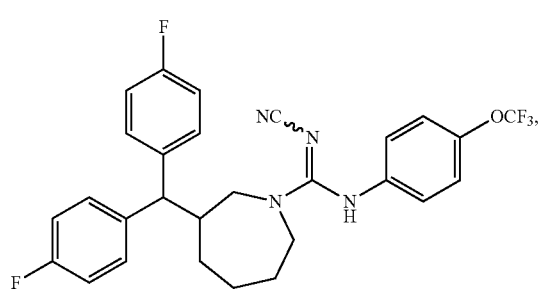
152
-continued
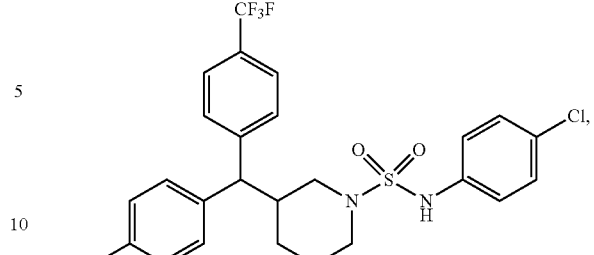
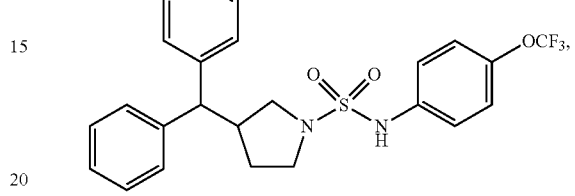
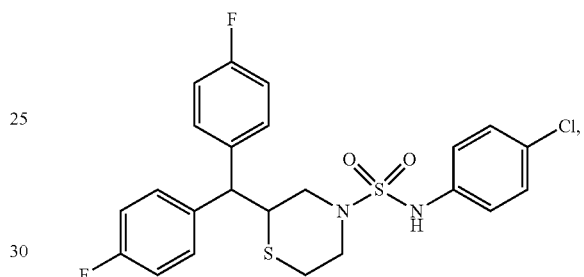
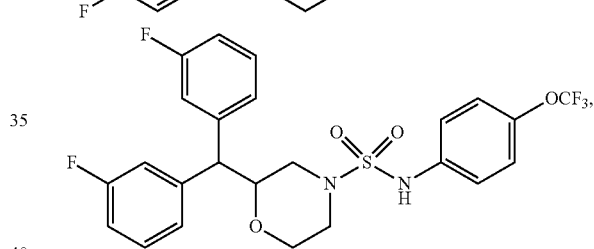
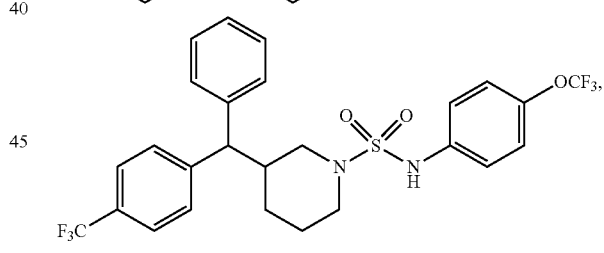
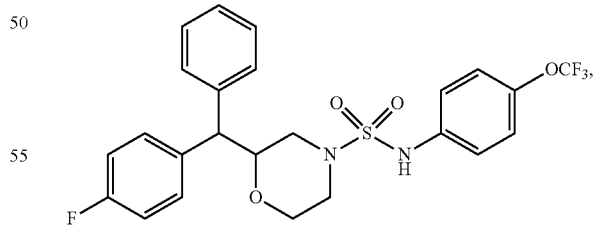
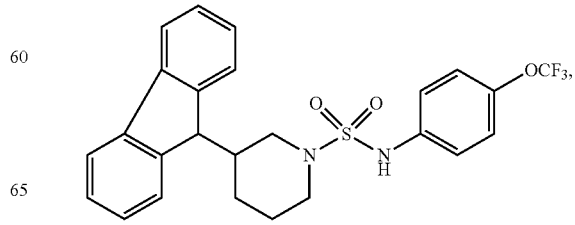

153
-continued
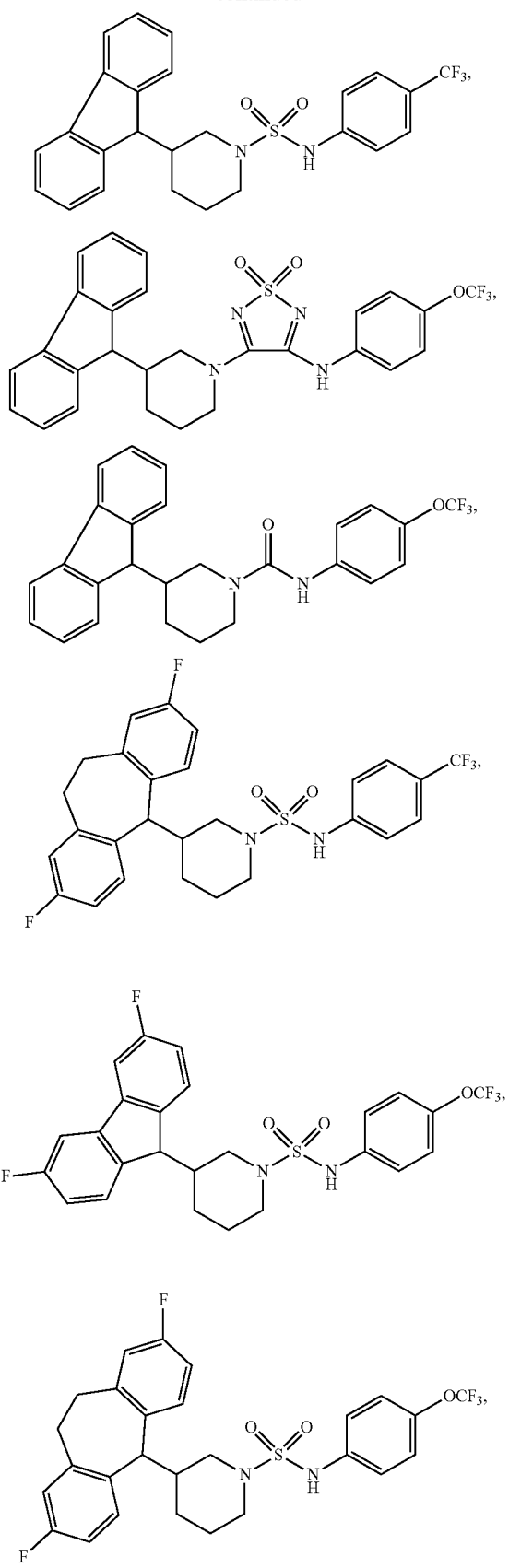
154
-continued
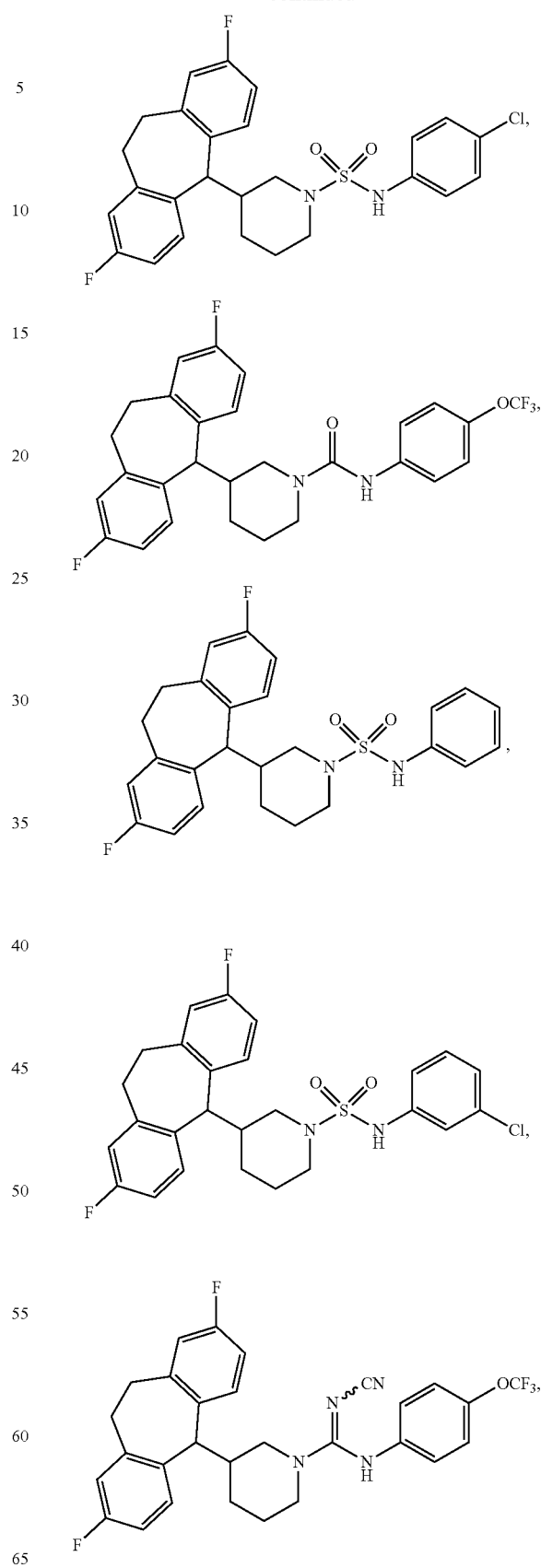

155
-continued
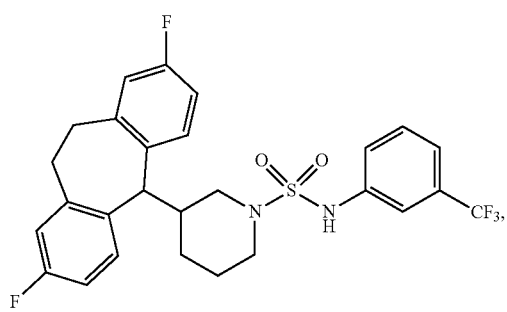
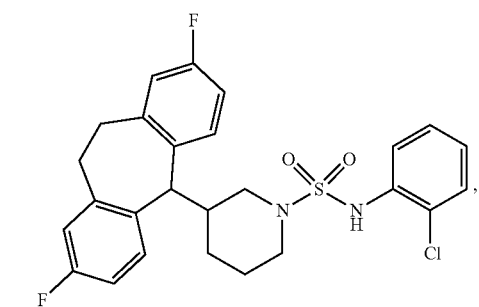
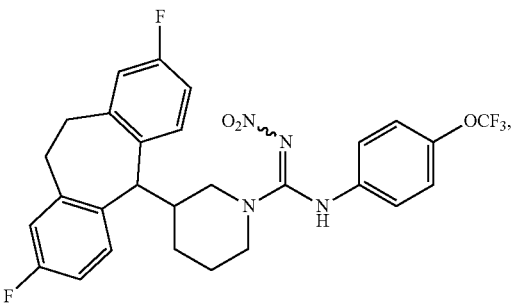
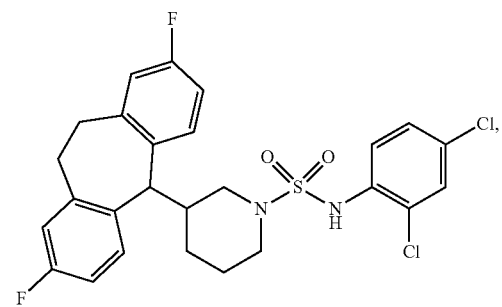
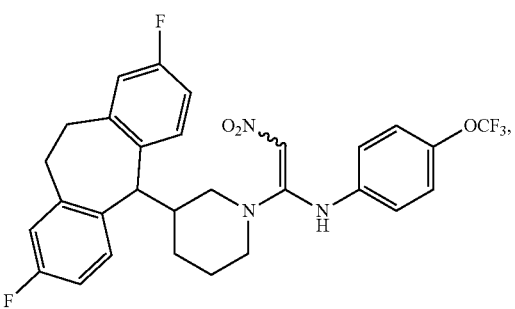
156
-continued
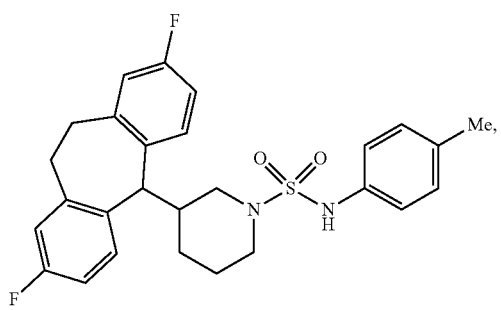
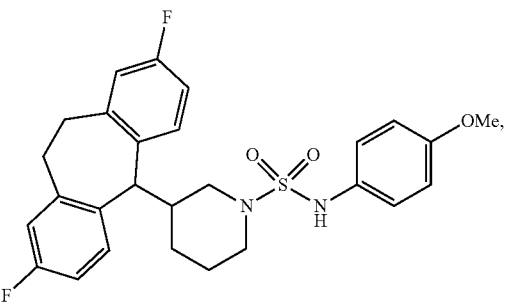
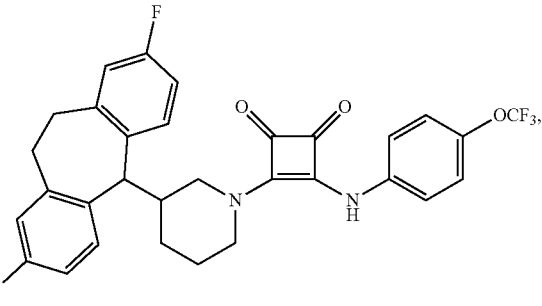
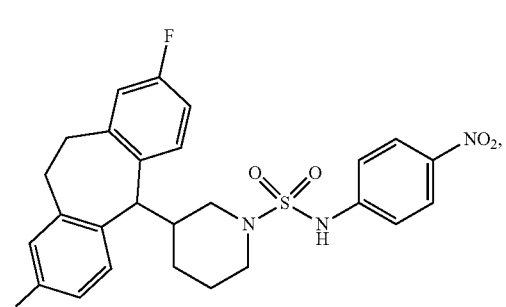
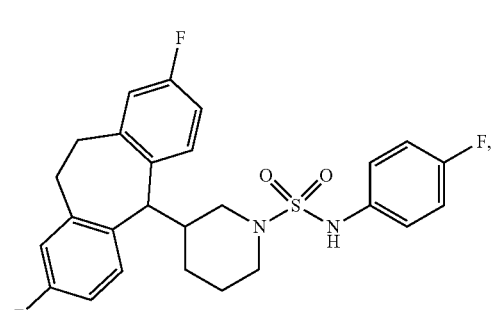

157
-continued
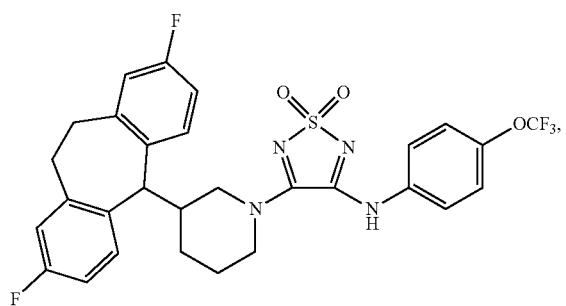
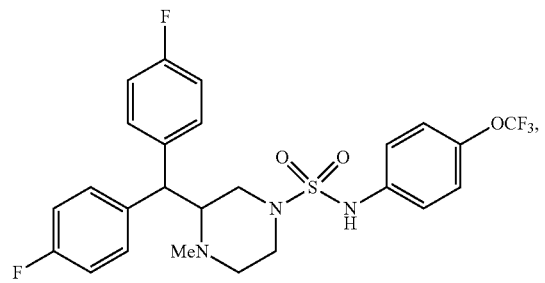
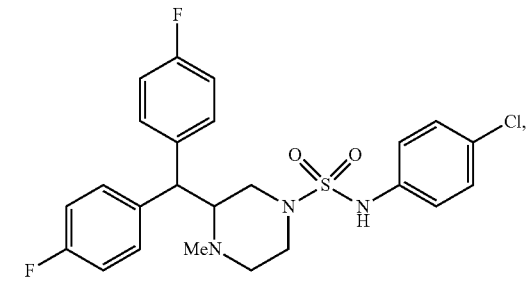
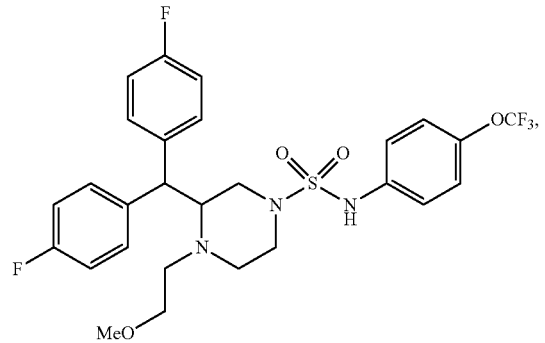
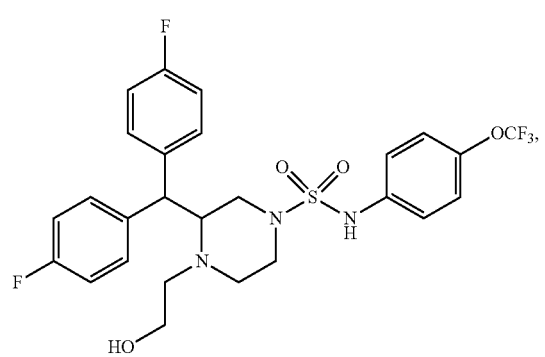
158
-continued
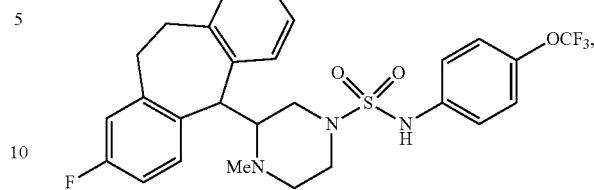
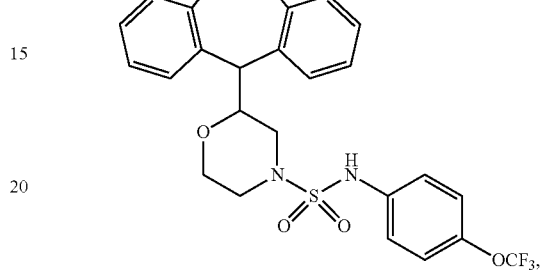
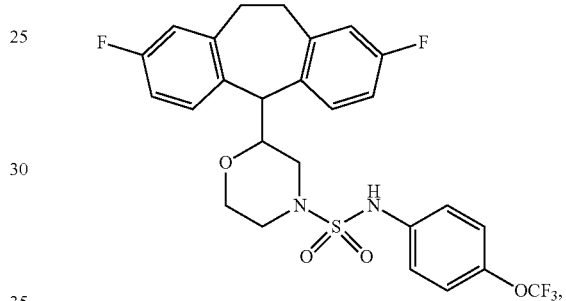
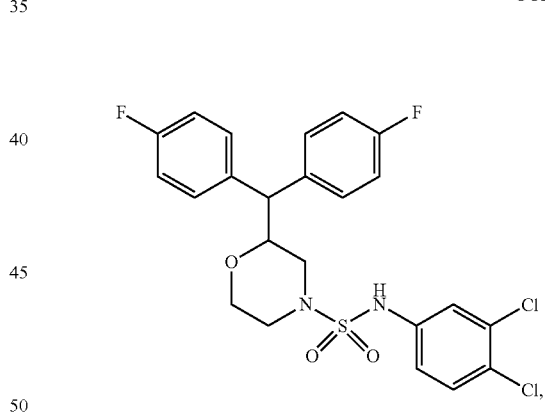
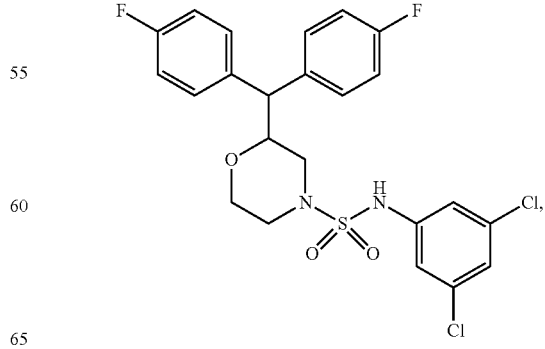

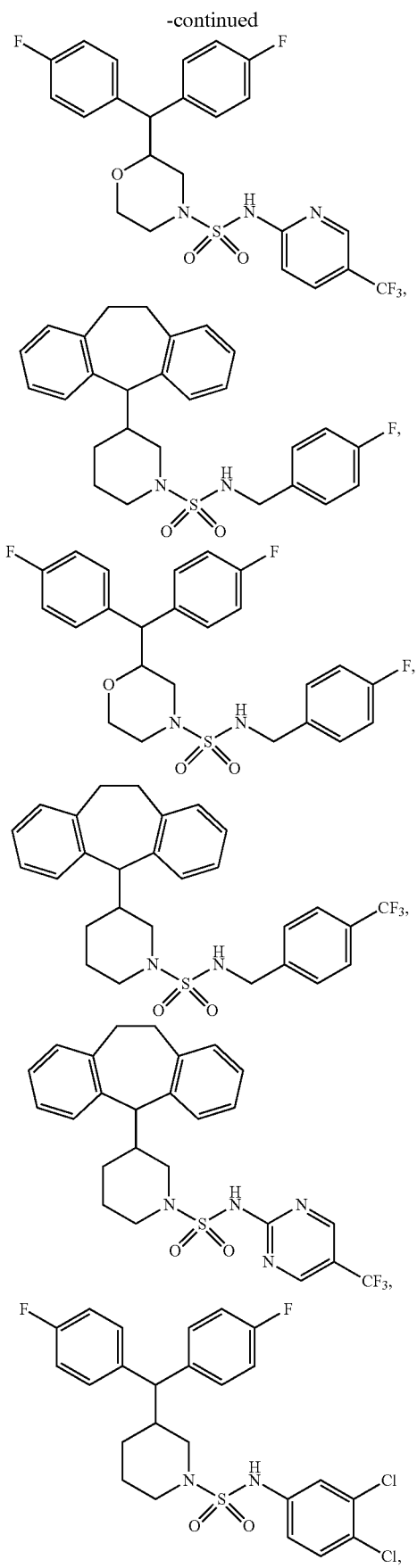

-continued

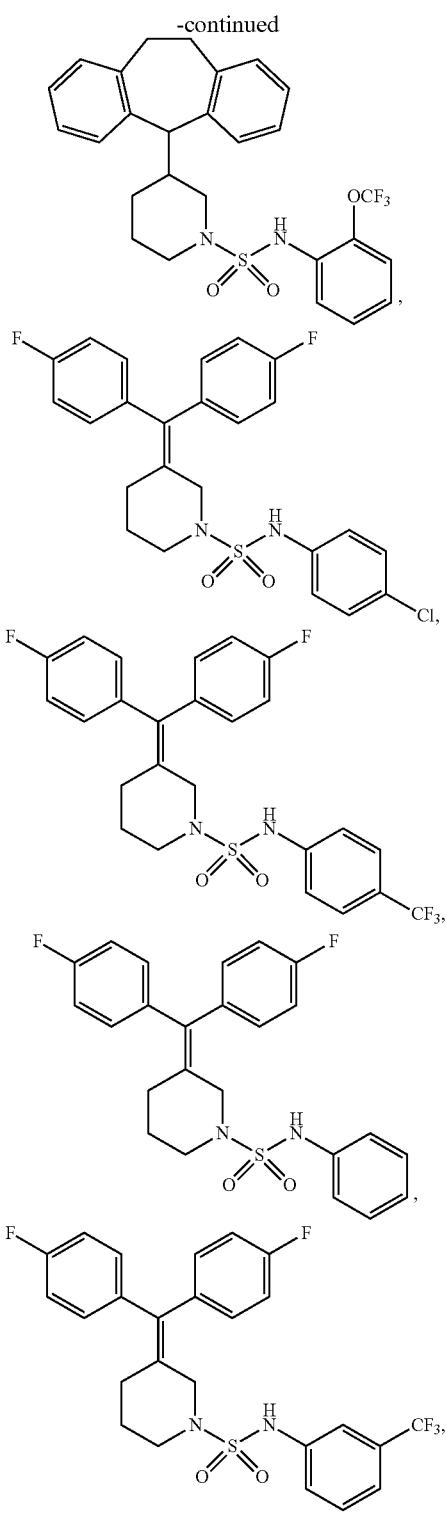

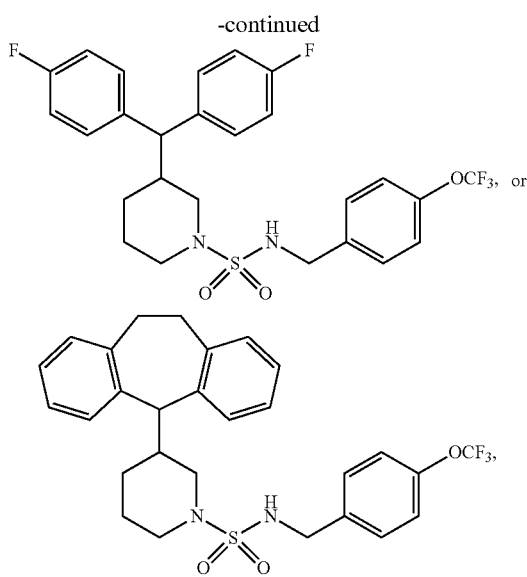

or a pharmaceutically acceptable salt thereof.

3. A composition, comprising the compound of claim 1.

4. A pharmaceutical composition, comprising the compound of claim 1, and a pharmaceutically acceptable excipient.

5. A composition, comprising the compound of claim 2.

6. A pharmaceutical composition, comprising the compound of claim 2, and a pharmaceutically acceptable excipient.

7. A compound, selected from:

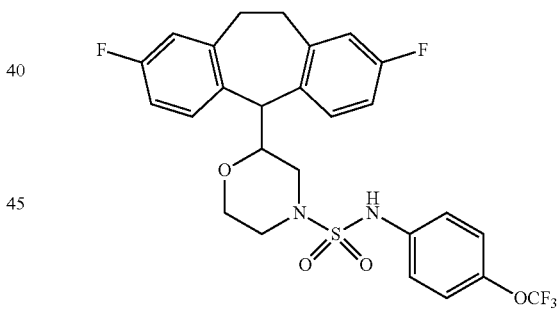

or a pharmaceutically acceptable salt thereof.

8. A composition comprising the compound of claim 7.

9. A pharmaceutical composition, comprising the compound of claim 7, and a pharmaceutically acceptable excipient.

* * * * *

UNITED STATES PATENT AND TRADEMARK OFFICE
CERTIFICATE OF CORRECTION

PATENT NO. : 12,398,103 B2
APPLICATION NO. : 17/912404
DATED : August 26, 2025
INVENTOR(S) : Michael Ohlmeyer Page 1 of 1

It is certified that error appears in the above-identified patent and that said Letters Patent is hereby corrected as shown below:

In the Claims

In Claim 1, Column 141, Line 66, please replace "–C(O) OR$^1$" with -- –C(O)OR$^1$--.
In Claim 1, Column 142, Line 7, please replace "(O) OR$^5$" with --(O)OR$^5$--.
In Claim 1, Column 142, Line 8, please replace "–C(O) OR$^3$" with -- –C(O)OR$^3$--.

In Claim 2, Column 142, Lines 55-65, please replace " 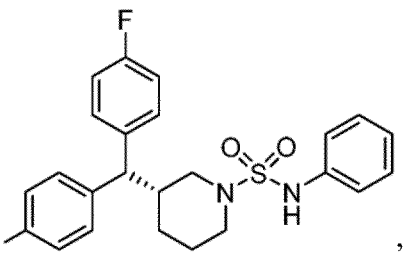 " with 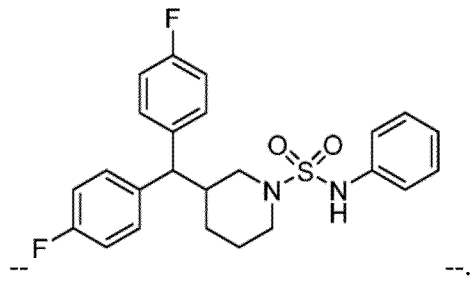 --.

Signed and Sealed this
Thirtieth Day of December, 2025

John A. Squires
*Director of the United States Patent and Trademark Office*